(12) United States Patent
Tran et al.

(10) Patent No.: US 10,200,834 B2
(45) Date of Patent: *Feb. 5, 2019

(54) SMART DEVICE

(71) Applicant: Bao Tran, Saratoga, CA (US)

(72) Inventors: Bao Tran, Saratoga, CA (US); Ha Tran, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,718

(22) Filed: Nov. 22, 2017

(65) Prior Publication Data

US 2018/0133583 A1 May 17, 2018

Related U.S. Application Data

(63) Continuation of application No. 15/144,773, filed on May 2, 2016, now Pat. No. 9,610,476, and a
(Continued)

(51) Int. Cl.
*G06F 19/00* (2018.01)
*H04W 4/38* (2018.01)
(Continued)

(52) U.S. Cl.
CPC ............. *H04W 4/38* (2018.02); *A42B 3/0433* (2013.01); *A61B 5/11* (2013.01); *A61B 5/6804* (2013.01); *A63B 24/0006* (2013.01); *A63B 24/0021* (2013.01); *A63B 24/0062* (2013.01); *A63B 24/0075* (2013.01); *A63B 43/004* (2013.01); *A63B 60/46* (2015.10); *A63B 69/36* (2013.01); *A63B 69/38* (2013.01); *A63B 71/06* (2013.01); *A63B 71/145* (2013.01); *A63F 11/00* (2013.01); *A63F 13/211* (2014.09); *B33Y 10/00* (2014.12); *G01L 5/0052* (2013.01); *G06F 1/163* (2013.01); *G06F 3/00* (2013.01); *G06F 3/017* (2013.01); *G06K 9/00342* (2013.01); *G06K 9/00355* (2013.01); *G06K 9/00671* (2013.01); *G06K 19/025* (2013.01); *G06K 19/07762* (2013.01); *G06Q 40/08* (2013.01); *G09B 19/003* (2013.01); *G09B 19/0038* (2013.01); *G16H 20/30* (2018.01); *G16H 30/20* (2018.01); *G16H 40/63* (2018.01); *G16H 40/67* (2018.01); *H04N 5/2253* (2013.01); *H04N 7/18* (2013.01); *H04Q 9/00* (2013.01); *H04W 84/18* (2013.01); *A61B 5/0022* (2013.01); *A61B 5/01* (2013.01); *A61B 5/024* (2013.01); *A61B 5/0402* (2013.01); *A61B 5/053* (2013.01); *A61B 5/055* (2013.01); *A61B 5/0533* (2013.01); *A61B 5/4872* (2013.01); *A61B 5/6806* (2013.01); *A61B 5/6895* (2013.01); *A61B 2503/10* (2013.01);
(Continued)

(58) Field of Classification Search
USPC ...................................................... 463/16–42
See application file for complete search history.

(56) References Cited

U.S. PATENT DOCUMENTS

| 6,720,984 B1 * | 4/2004 | Jorgensen | ............... G06F 3/015 |
| | | | 600/300 |
| 8,747,336 B2 * | 6/2014 | Tran | .................... G06F 19/3418 |
| | | | 600/300 |

(Continued)

*Primary Examiner* — Masud Ahmed
(74) *Attorney, Agent, or Firm* — Tran & Associates

(57) ABSTRACT

An Internet of Thing (IoT) device includes a body and sensors including a camera and an accelerometer; a processor; and a wireless transceiver coupled to the processor.

20 Claims, 21 Drawing Sheets

US 10,200,834 B2
Page 2

Related U.S. Application Data continuation-in-part of application No. 15/612,808, filed on Jun. 2, 2017, now Pat. No. 10,022,614.

(51) Int. Cl.

| | | |
|---|---|---|
| A63B 71/14 | (2006.01) | |
| A63B 69/36 | (2006.01) | |
| A61B 5/11 | (2006.01) | |
| A61B 5/00 | (2006.01) | |
| G06F 3/00 | (2006.01) | |
| G06K 9/00 | (2006.01) | |
| G09B 19/00 | (2006.01) | |
| G06F 1/16 | (2006.01) | |
| B33Y 10/00 | (2015.01) | |
| G01L 5/00 | (2006.01) | |
| H04W 84/18 | (2009.01) | |
| A63B 60/46 | (2015.01) | |
| A63B 24/00 | (2006.01) | |
| A63B 69/38 | (2006.01) | |
| A42B 3/04 | (2006.01) | |
| A63B 71/06 | (2006.01) | |
| H04Q 9/00 | (2006.01) | |
| G16H 30/20 | (2018.01) | |
| A63B 43/00 | (2006.01) | |
| G06F 3/01 | (2006.01) | |
| H04N 5/225 | (2006.01) | |
| H04N 7/18 | (2006.01) | |
| A63F 13/211 | (2014.01) | |
| A63F 11/00 | (2006.01) | |
| G16H 20/30 | (2018.01) | |
| G16H 40/63 | (2018.01) | |
| G16H 40/67 | (2018.01) | |
| G06K 19/02 | (2006.01) | |
| G06K 19/077 | (2006.01) | |
| G06Q 40/08 | (2012.01) | |
| G16H 50/20 | (2018.01) | |
| A63B 71/12 | (2006.01) | |
| A63B 69/00 | (2006.01) | |
| A63B 69/02 | (2006.01) | |
| A63B 69/06 | (2006.01) | |
| A63B 69/16 | (2006.01) | |
| A63B 71/08 | (2006.01) | |
| A63B 71/10 | (2006.01) | |
| A63B 21/072 | (2006.01) | |
| H04B 1/04 | (2006.01) | |
| H04L 29/08 | (2006.01) | |
| H04W 88/02 | (2009.01) | |
| A61B 5/01 | (2006.01) | |
| A61B 5/024 | (2006.01) | |
| A61B 5/0402 | (2006.01) | |
| A61B 5/053 | (2006.01) | |
| A61B 5/055 | (2006.01) | |

(52) U.S. Cl.
CPC ..... *A61B 2562/0219* (2013.01); *A63B 21/072* (2013.01); *A63B 21/0724* (2013.01); *A63B 21/0726* (2013.01); *A63B 69/0002* (2013.01); *A63B 69/0026* (2013.01); *A63B 69/0028* (2013.01); *A63B 69/0048* (2013.01); *A63B 69/0071* (2013.01); *A63B 69/02* (2013.01); *A63B 69/06* (2013.01); *A63B 69/16* (2013.01); *A63B 69/3632* (2013.01); *A63B 71/085* (2013.01); *A63B 71/10* (2013.01); *A63B 71/1216* (2013.01); *A63B 71/1291* (2013.01); *A63B 71/141* (2013.01); *A63B 2071/125* (2013.01); *A63B 2071/1233* (2013.01); *A63B 2071/1283* (2013.01); *A63B 2207/02* (2013.01); *A63B 2208/0204* (2013.01); *A63B 2220/12* (2013.01); *A63B 2220/13* (2013.01); *A63B 2220/16* (2013.01); *A63B 2220/20* (2013.01); *A63B 2220/24* (2013.01); *A63B 2220/30* (2013.01); *A63B 2220/40* (2013.01); *A63B 2220/51* (2013.01); *A63B 2220/53* (2013.01); *A63B 2220/56* (2013.01); *A63B 2220/72* (2013.01); *A63B 2220/74* (2013.01); *A63B 2220/75* (2013.01); *A63B 2220/76* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/30* (2013.01); *A63B 2225/50* (2013.01); *A63B 2225/54* (2013.01); *A63B 2230/04* (2013.01); *A63B 2230/06* (2013.01); *A63B 2230/50* (2013.01); *A63B 2230/60* (2013.01); *A63B 2230/70* (2013.01); *A63B 2243/007* (2013.01); *A63B 2243/0025* (2013.01); *A63B 2243/0037* (2013.01); *A63B 2243/0054* (2013.01); *A63B 2243/0066* (2013.01); *A63B 2243/0095* (2013.01); *A63B 2244/102* (2013.01); *A63B 2244/18* (2013.01); *A63B 2244/19* (2013.01); *A63B 2244/20* (2013.01); *A63B 2244/203* (2013.01); *G16H 50/20* (2018.01); *H04B 1/04* (2013.01); *H04L 67/10* (2013.01); *H04Q 2209/40* (2013.01); *H04W 88/02* (2013.01)

(56) References Cited

U.S. PATENT DOCUMENTS

| | | | |
|---|---|---|---|
| 2002/0065121 A1* | 5/2002 | Fukunaga | A63F 13/08 463/8 |
| 2006/0160616 A1* | 7/2006 | Kato | A63F 13/10 463/30 |
| 2010/0144414 A1* | 6/2010 | Edis | A63B 24/0006 463/8 |
| 2012/0144554 A1* | 6/2012 | Thellmann | A63B 21/4033 2/161.1 |
| 2013/0066448 A1* | 3/2013 | Alonso | H04Q 9/00 700/91 |
| 2015/0283450 A1* | 10/2015 | McRoberts | G09B 19/0038 473/470 |
| 2015/0360080 A1* | 12/2015 | Hadaschik | G01P 7/00 73/865.4 |
| 2016/0055422 A1* | 2/2016 | Li | G05B 15/02 706/12 |

* cited by examiner

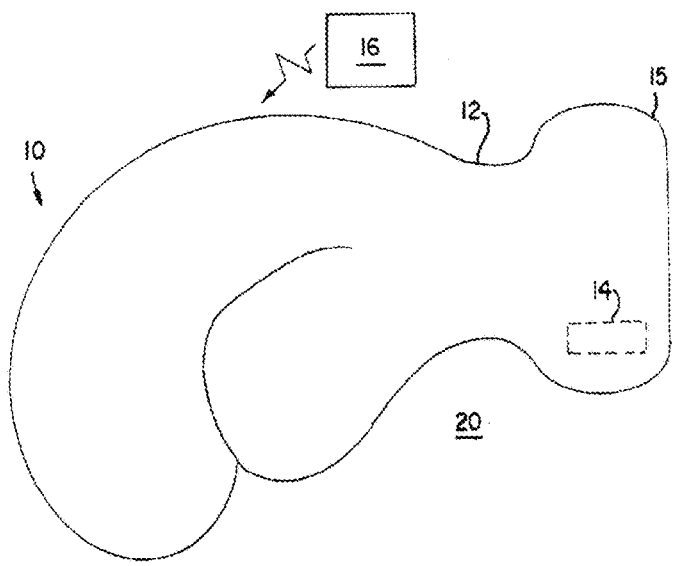
FIG. 7  FIG. 8
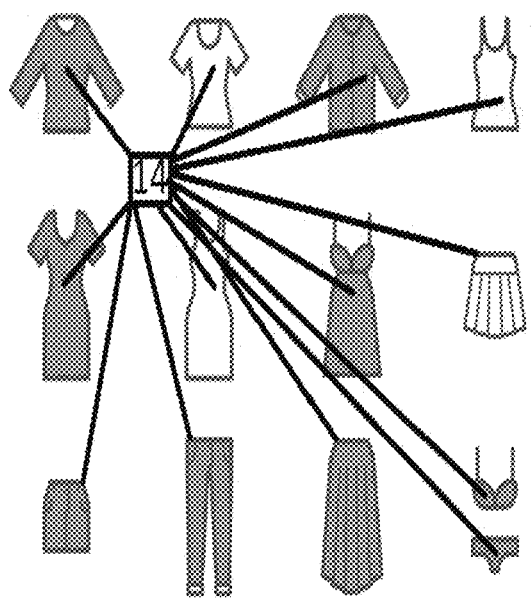
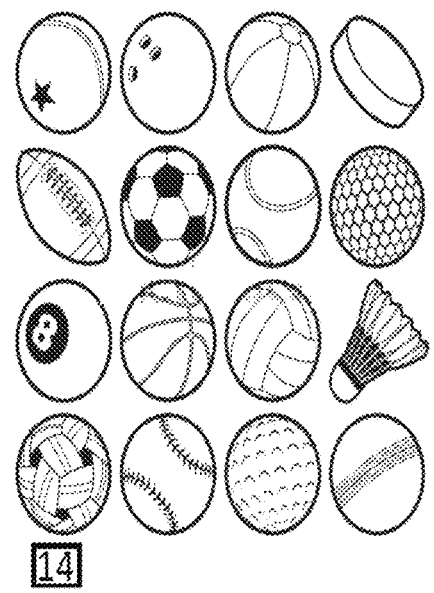
FIG. 9  FIG. 10

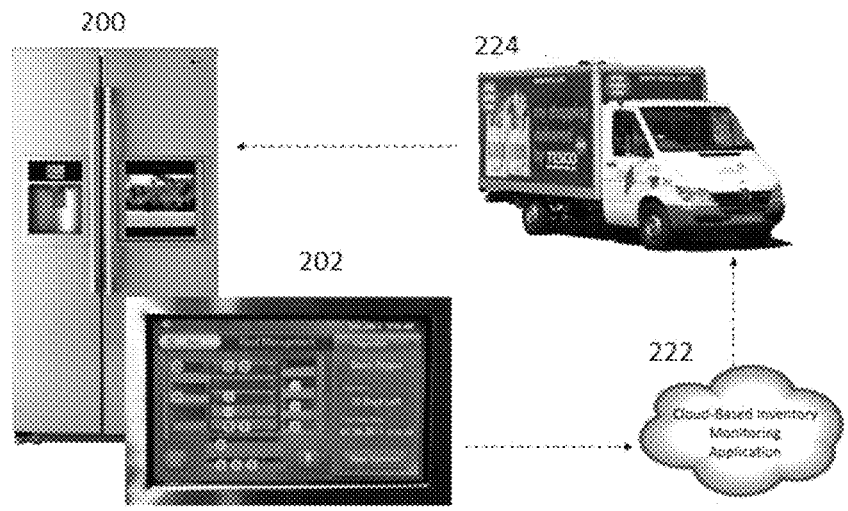

FIG. 14A

| |
|---|
| Refrigerators in a local area provide real-time demand estimate (240) |
| Farmers predict cycle's harvest (242) |
| Refrigerator generates forecast of weekly demands (244) |
| System matches harvest cycle to each refrigerator requirement (246) |
| System automatically emails orders to the farmers and producers, who harvest or prepare accordingly (248). |
| Goods are delivered from farmers or vendors to a local staging area or warehouse and then packaged for delivery (250) |
| Owners either pickup from the local staging area or a ride-sharing service can pick up and deliver in the same day (252) |
| Refrigerator inventory is updated (254) |

FIG. 14B

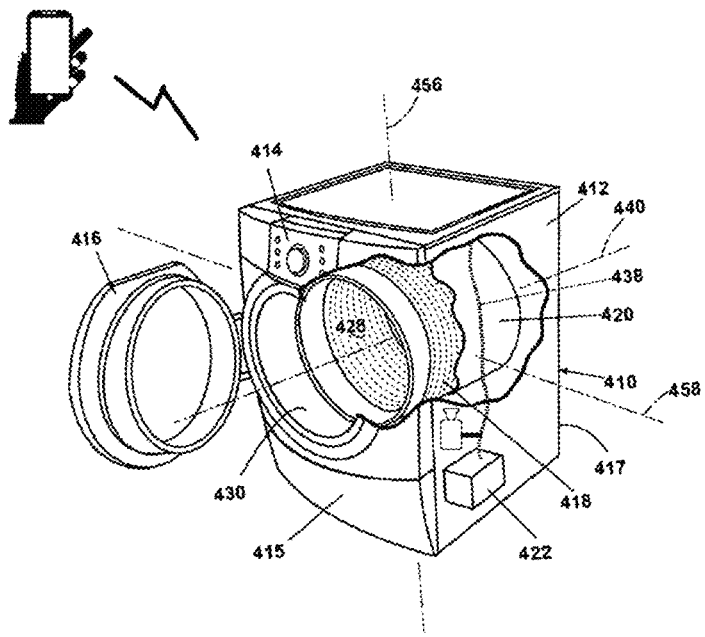

FIG. 14C

SMART DEVICE

BACKGROUND

The present invention relates to the Internet of Things (IoT).

SUMMARY

In one aspect, an Internet of Thing (IoT) device includes a body and sensors including a camera and an accelerometer; a processor; and a wireless transceiver coupled to the processor.

Implementations/applications of the above aspect may include one or more of the following. The ability to network embedded devices with limited CPU, memory and power resources means that IoT finds applications in nearly every field. Such systems could be in charge of collecting information in settings ranging from natural ecosystems to buildings and factories, thereby finding applications in fields of environmental sensing and urban planning IoT systems could also be responsible for performing actions, not just sensing things. Intelligent shopping systems, for example, could monitor specific users' purchasing habits in a store by tracking their specific mobile phones. These users could then be provided with special offers on their favorite products, or even location of items that they need, which their fridge has automatically conveyed to the phone. Additional examples of sensing and actuating are reflected in applications that deal with heat, water, electricity and energy management, as well as cruise-assisting transportation systems. Other applications that the Internet of things can provide is enabling extended home security features and home automation.

Thus, the Internet of things creates an opportunity to measure, collect and analyze an ever-increasing variety of behavioral statistics. Cross-correlation of this data could revolutionize the targeted marketing of products and services. Big data and the IoT work in conjunction. From a media perspective, data is the key derivative of device interconnectivity, whilst being pivotal in allowing clearer accuracy in targeting. The Internet of things therefore transforms the media industry, companies and even governments, opening up a new era of economic growth and competitiveness. The wealth of data generated by this industry (i.e. big data) will allow practitioners in advertising and media to gain an elaborate layer on the present targeting mechanisms used by the industry.

Environmental monitoring applications of the IoT typically use sensors to assist in environmental protection by monitoring air or water quality, atmospheric or soil conditions, and can even include areas like monitoring the movements of wildlife and their habitats. Development of resource constrained devices connected to the Internet also means that other applications like earthquake or tsunami early-warning systems can also be used by emergency services to provide more effective aid. IoT devices in this application typically span a large geographic area and can also be mobile.

Monitoring and controlling operations of urban and rural infrastructures like bridges, railway tracks, on- and offshore-wind-farms is a key application of the IoT. The IoT infrastructure can be used for monitoring any events or changes in structural conditions that can compromise safety and increase risk. It can also be used for scheduling repair and maintenance activities in an efficient manner, by coordinating tasks between different service providers and users of these facilities. IoT devices can also be used to control critical infrastructure like bridges to provide access to ships. Usage of IoT devices for monitoring and operating infrastructure is likely to improve incident management and emergency response coordination, and quality of service, up-times and reduce costs of operation in all infrastructure related areas.

Digital control systems to automate process controls, operator tools and service information systems to optimize plant safety and security are within the purview of the IoT, but it also extends itself to asset management via predictive maintenance, statistical evaluation, and measurements to maximize reliability. Smart industrial management systems can also be integrated with the Smart Grid, thereby enabling real-time energy optimization. Measurements, automated controls, plant optimization, health and safety management, and other functions are provided by a large number of networked sensors.

The term IIoT (Industrial Internet of Things) is often encountered in the manufacturing industries, referring to the industrial subset of the IoT. IIoT in manufacturing could generate so much business value that it will eventually lead to the fourth industrial revolution, so the so-called Industry 4.0. It is estimated that in the future, successful companies will be able to increase their revenue through Internet of things by creating new business models and improve productivity, exploit analytics for innovation, and transform workforce. Integration of sensing and actuation systems, connected to the Internet, is likely to optimize energy consumption as a whole. IoT devices will be integrated into all forms of energy consuming devices (switches, power outlets, bulbs, televisions, etc.) and be able to communicate with the utility supply company in order to effectively balance power generation and energy usage. Such devices would also offer the opportunity for users to remotely control their devices, or centrally manage them via a cloud based interface, and enable advanced functions like scheduling (e.g., remotely powering on or off heating systems, controlling ovens, changing lighting conditions etc.). Besides home based energy management, the IoT is especially relevant to the Smart Grid since it provides systems to gather and act on energy and power-related information in an automated fashion with the goal to improve the efficiency, reliability, economics, and sustainability of the production and distribution of electricity. Using metering infrastructure (AMI) devices connected to the Internet backbone, electric utilities can not only collect data from end-user connections, but also manage other distribution automation devices like transformers and reclosers.

IoT devices can be used to enable remote health monitoring and emergency notification systems. These health monitoring devices can range from blood pressure and heart rate monitors to advanced devices capable of monitoring specialized implants, such as pacemakers Fitbit electronic wristbands or advanced hearing aids. Some hospitals have begun implementing "smart beds" that can detect when they are occupied and when a patient is attempting to get up. It can also adjust itself to ensure appropriate pressure and support is applied to the patient without the manual interaction of nurses. Specialized sensors can also be equipped within living spaces to monitor the health and general well-being of senior citizens, while also ensuring that proper treatment is being administered and assisting people regain lost mobility via therapy as well. Other consumer devices to encourage healthy living, such as, connected scales or wearable heart monitors, are also a possibility with the IoT. More and more end-to-end health monitoring IoT platforms are coming up for antenatal and chronic patients, helping one manage health vitals and recurring medication requirements.

BRIEF DESCRIPTION OF THE DRAWINGS

FIG. 7 shows an exemplary glove,

FIG. 8 shows an exemplary smart band,

FIG. 9 shows exemplary smart clothing,

FIG. 10 shows exemplary smart balls.

FIG. 11A shows exemplary smart rackets while

FIG. 12A-12B show exemplary protective gears, while

FIGS. 13A-13C and FIGS. 14A-14K show exemplary smart IOT appliances.

FIG. 16A-16C shows exemplary coaching system for skiing, bicycling, and weightlifting/free style exercise, respectively, while

Similar reference characters denote corresponding features consistently throughout the attached drawings.

DETAILED DESCRIPTION OF THE PREFERRED EMBODIMENTS

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

Figure 1A:
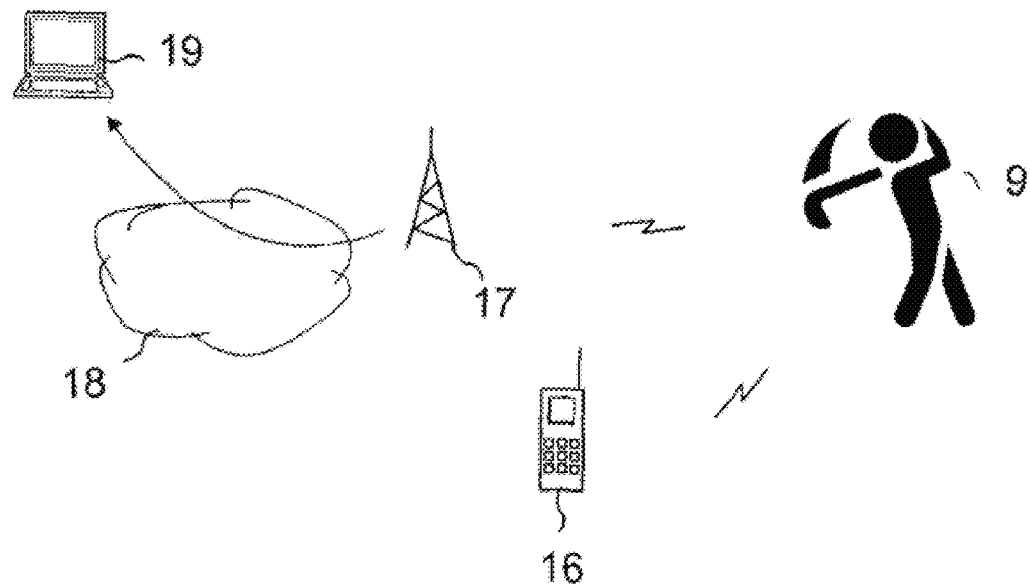
FIG. 1A illustrates an exemplary environment for communicating data from a monitoring device to external computers

FIG. 1A illustrates an exemplary environment for communicating data from a monitoring device to external computers. In FIG. 1A, the monitoring device used for a sport device 9 includes an interface with a radio transmitter for forwarding the result of the comparison to a remote device. In one example, the monitoring device may include an additional switch and user interface. The user interface may be used by the user in order to trigger transmission of the comparison of the hand or foot pattern reference data with the stroke patterns data to the remote device. Alternatively, the transmission may occur automatically each time the device has been used, or may be triggered by placing the sport device in a cradle or base. All parts of the monitoring device may be encapsulated with each other and/or may be integrated into or attached to the body of the sport device 9. Alternatively, a radio transmitter may be arranged separately from the other parts, for instance, in a battery charger, cradle or base of the sport device 9. In that example, the interface 7 may include contact terminals in the sport device 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device. In FIG. 1A, the remote device may be a mobile phone 16, PDA or computer 19, which receives the information directly from the monitoring device via a short range radio connection, as one example of a transmitter, such as a Bluetooth or a Wifi or a Zigbee connection. In one example, the user of the remote device may receive information about how thoroughly the sport device 9 has been used or the need to provide a replacement sport device. FIG. 1A also illustrates an alternate example of a transmitter, using an intermediate receiver 17 and a network 18, such as a cellular radio system. Also in this example, the radio transmitter may be located in connection with the sport device 9 or alternatively in connection, with a charger, cradle or base station of the sport device 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device. The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the sport device 9 to the remote device 19, 16.

Figure 1B:
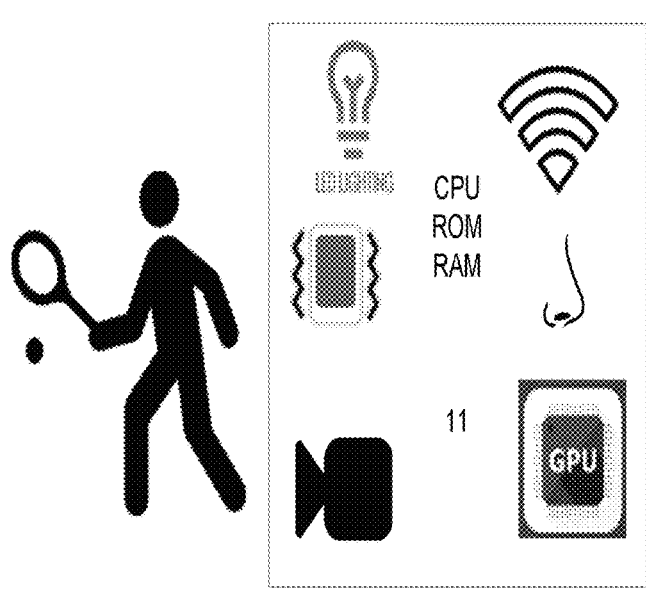
FIG. 1B is a perspective view of an exemplary IoT sport device system.

FIG. 1B shows a block diagram of the unit 9 with processor/RAM/ROM 11. The unit 9 includes a motion sensor, a multi-axis accelerometer, and a strain gage 42. The multi-axis accelerometer may be a two-axis or three-axis accelerometer. Strain gage 21 is mounted in the neck of the racket, and measures force applied to the ball, i.e., force in a z direction. Acceleration and force data are acquired by the microprocessor at a data acquisition rate (sampling rate) of from about 10 to 50 samples/second, e.g., about 20 samples/second. The acceleration data is used to infer motion, using an algorithm discussed below; it is not converted to position data. In this embodiment, because the sensors and strain gage are not in the head region, the head can be removable and replaceable, e.g., by threaded engagement with the handle (not shown), so that the sport device can continue to be used after instrument wear has occurred. Any desired type of removable head or cartridge can be used.

The unit 11 also includes a camera, which can be a 360 degree camera. Alternatively, the camera can be a 3D camera such as the Kinect camera or the Intel RealSense camera for ease of generating 3D models and for detecting distance of objects. To reduce image processing load, each camera has a high performance GPU to perform local processing, and the processed images, sound, and odor data are uploaded to a cloud storage for subsequent analysis.

The unit 11 includes an electronic nose to detect odor. The electronic nose can simply be a MEMS device acting as a particle counter. An embodiment of the electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

An electronic tongue sensor can be provided to sense quality of sweat or liquid. The tongue includes a liquid molecule sensor module, a control unit and an output unit. Body liquid is applied or swiped on to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of fog or liquid, among others.

In one embodiment for analyzing tooth structure, restorative materials within a tooth structure, and disease states of a tooth, the unit 11 includes a probe 20 which may be attached to a variety of sport probes, and instruments to afford adaptability to a variety of situations in providing diagnostic information on an object such as a naturally occurring structure, man-made materials placed or found within the structure, diseased or otherwise affected, infected or effected structure, as well as structure that has been eroded, worn by attrition, abraded, abfracted, fractured, crazed, broken or otherwise compromised through sport enthusiast use, misuse, fatigue or longevity of use. The probe 20 generates electrical outputs which are interpreted by a smart phone or computer.

In one embodiment, the probe 20 can be a vibratory transducer that sends out vibrations at known frequency and amplitude. The probe 20 also includes a receiver which can be an accelerometer, for example. The accelerometer is attached to the teeth and connected to a computer. The accelerometer digitizes the received vibrations and provides them into the phone or computer. The transducer can be a single piezoelectric transducer or an array with elements arranged to fit in a mouthpiece or an appliance to be worn over the oral arch. The transducer elements can be mounted in silicone rubber or other material suitable for damping mechanical coupling between the elements. Other materials may also be used for the array construction. For example, the transducer may be formed from one or more pieces of piezocomposite material, or any material that converts electrical energy to acoustic energy. The receiver can also be positioned to fit in the mouthpiece or appliance. One embodiment of the receiver is an accelerometer, but a suitable piezoelectric transducer can serve as the receiver as well.

The software in the computer compares these inputs to known vibration responses corresponding to striking states on a ball or sport object. The computer 30 displays a response on the computer screen for that user.

Figure 1C:
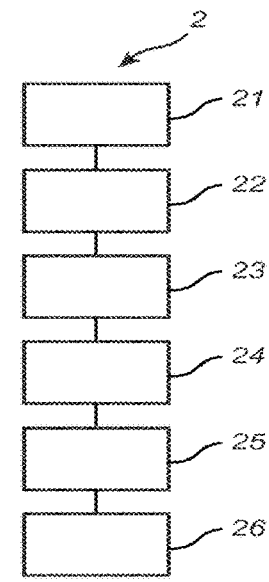
FIG. 1C is an exemplary process supported by the device according to the present invention.

FIG. 1C schematically shows a method or app 2 which may be implemented by the computing unit 11 shown in FIG. 1B. For example, the app 2 may be a computer implemented method. A computer program may be provided for executing the app 2. The app 2 includes code for:

(21) capture user motion with accelerometer or gyroscope
(22) capture VR views through camera and process using GPU
(23) capture user emotion using facial recognition or GSR
(24) model user action using kinematic model
(25) compare user action with idea action
(26) coach user on improvement to user sport techniques.

Figure 2A:
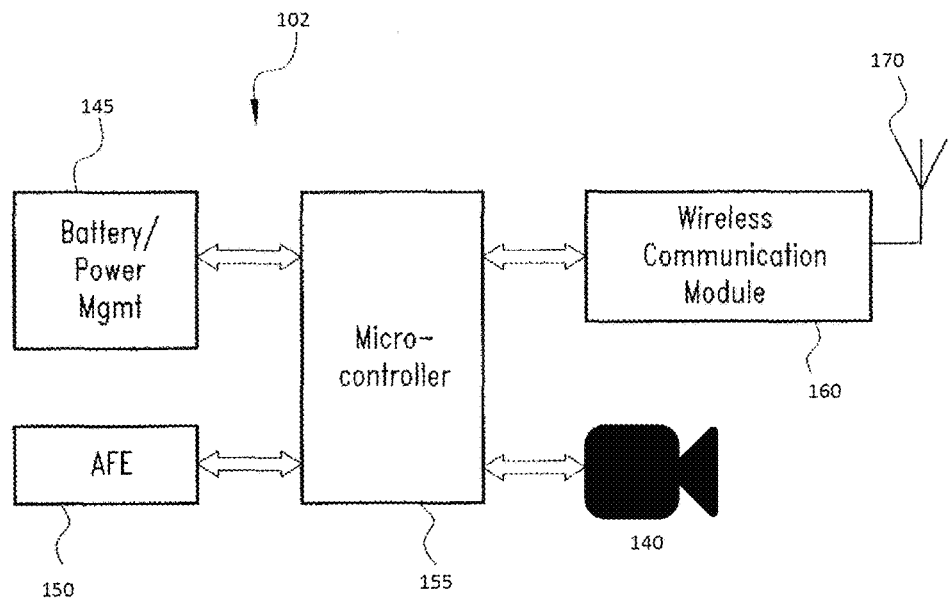
FIG. 2A is a block diagram of an electronic circuit for a smart device.

As shown in FIG. 2A, a microcontroller 155 receives and processes signals from the sensor 112-114, and converts those signals into an appropriate digital electronic format. The microcontroller 155 wirelessly transmits tension information in the appropriate digital electronic format, which may be encoded or encrypted for secure communications, corresponding to the sensed traffic and/or crime indication through a wireless communication module or transceiver 160 and antenna 170. Optionally, a camera 140 can be provided to visually detect traffic and/or crime and movement of the structure. While monitoring of the smart device 100 traffic and/or crime is continuous, transmission of tension information can be continuous, periodic or event-driven, such as when the tension enters into a warning or emergency level. Typically the indicated tension enters a warning level, then an emergency level as tension drops below the optimal range, but corresponding warning and emergency levels above the optimal range can also be used if supported by the smart device 100. The microcontroller 155 is programmed with the appropriate warning and emergency levels, as well as internal damage diagnostics and self-recovery features.

The tension information can take any form, including a simple warning/emergency indication that the tension is approaching or exceeding tension specifications, respectively. While under-tension is known to be the primary cause of structural or mechanical problems associated with devices, over-tension can also be a problem and can also be reported by the smart device 100.

The sensors can detect force, load, tension and compression forces on the device such as the device. Other data includes Acceleration; Velocity; Global absolute displacement; Local relative displacement; Rotation; Strain; Stress; Force; and Static-position video. Wind speed/direction; External temperature; weather parameters (rainfall, humidity, solar radiation, etc.); Internal or structural temperature; Mass loading (occupant count, etc.); Static tilt; Fatigue damage; Corrosion; Acoustic emission; and Moving-position video. A force is simply a push or pull to an object and can be detected by a load cell, pressure cell or strain sensor. A Load: Is simply a force applied to a structure. Ex: weight of vehicles or pedestrians, weight of wind pushing on sides. Tension & Compression are internal forces that make a member longer or shorter. Tension stretches a member and Compression pushes the member closer together. Acceleration can also be detected by Force-Balance (Servo) Piezoelectric Piezoresistive MEMS. Velocity can be measured by force-balance (servo) MEMS, or Mechanical Doppler Heated wire. A local Displacement sensor can be LVDT/Cable potentiometer Acoustic Optical/laser Temperature Electrical Optical fiber. A rotation sensor can be Gyro MEMS Gyro Tilt Electro-mechanical MEMS. A strain sensor can be a resistance gauge Vibrating wire Optical fiber Corrosion Electrical Chemical sensors. A traffic and/or crime sensor can be a microphone listening to acoustic emission, or Piezoelectric MEMS, for example, and sonar sound processing can be used to detect where crime activity is coming from.

The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

The circuit of FIG. 2A contains an analog front-end ("AFE") transducer 150 for interfacing signals from the sensor 112-114 to the microcontroller 155. The AFE 150 electrically conditions the signals coming from the sensor 112-114 prior to their conversion by the microcontroller 155 so that the signals are electrically compatible with the specified input ranges of the microcontroller 155. The microcontroller 155 can have a CPU, memory and peripheral circuitry. The microcontroller 155 is electrically coupled to a wireless communication module 160 using either a standard or proprietary communication standard. Alternatively, the microcontroller 155 can include internally any or all circuitry of the smart device 100, including the wireless communication module 160. The microcontroller 155 preferably includes power savings or power management circuitry 145 and modes to reduce power consumption significantly when the microcontroller 155 is not active or is less active. The microcontroller 155 may contain at least one Analog-to-Digital Converter (ADC) channel for interfacing to the AFE 150.

The battery/power management module 145 preferably includes the electromagnetic field (EMF) scavenging device, but can alternatively run off of previously stored electrical power from the battery alone. The battery/power management module 145 powers all the circuitry in the smart device 100, including the camera 140, AFE 150, microcontroller 155, wireless communication module 160, and antenna 170. Even though the smart device 100 is preferably powered by continuously harvesting RF energy, it is beneficial to minimize power consumption. To minimize power consumption, the various tasks performed by the circuit should be repeated no more often than necessary under the circumstances.

Stress information from the smart device 100 and other information from the microcontroller 155 is preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart device 100 themselves. In each smart device 100, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks:

1. Neighbor discovery: in this task each smart device 100 sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart device (node) so that minimum energy is consumed. 4. Data transmission: the microcontroller processes the collected color data and based on the adopted data dissemination approach, the smart device 100 will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

Figure 2B:
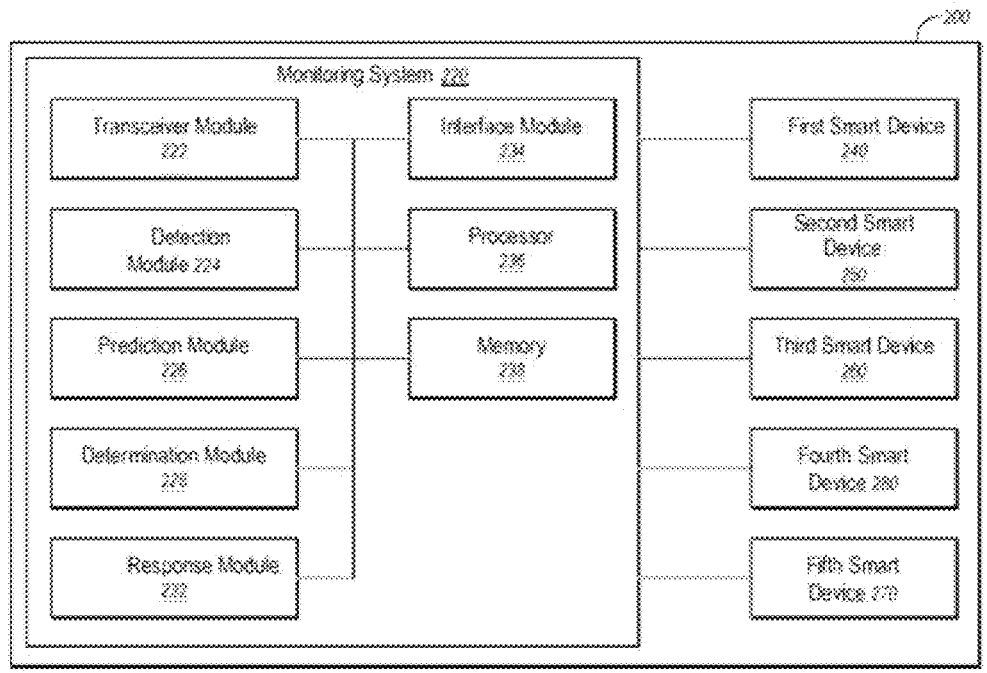
FIG. 2B is a block diagram of a big data system for predicting stress experienced by a structural unit such as a bridge, a building, or a plane, for example.

The electronic of FIG. 2A operates with a big data discovery system of FIG. 2B that determines events that may lead to failure. FIG. 2B is a block diagram of an example stress monitoring system 200 that may be process the stress detected by the smart device 100 of FIG. 1, arranged in accordance with at least some embodiments described herein. Along with the stress monitoring system 220, a first smart device such as a smart device 240, a second smart device 250, a third smart device 260, a fourth smart device 280, and additional sensors 270 may also be associated with the unit 200. The stress monitoring system 220 may include, but is not limited to, a transceiver module 222, a stress detection module 224, a stress prediction module 226, a determination module 228, a stress response module 232, an interface module 234, a processor 236, and a memory 238.

The transceiver module 222 may be configured to receive a stress report from each of the first, second, and third sport smart devices 240, 250, 260. In some embodiments, the transceiver module 222 may be configured to receive the stress reports over a wireless network. For example, the transceiver module 222 and the first, second, and third smart devices 240, 250, 260 may be connected over a wireless network using the IEEE 802.11 or IEEE 802.15 standards, for example, among potentially other standards. Alternately or additionally, the transceiver module 222 and the first, second, and third smart devices 240, 250, 260 may communicate by sending communications over conductors used to carry electricity to the first, second, and third smart devices 240, 250, 260 and to other electrical devices in the unit 200. The transceiver module 222 may send the stress reports from the first, second, and third smart devices 240, 250, 260 to the prediction module 226, the stress detection module 224, and/or the determination module 228.

The stress module 224 may be configured to detect stress on the sport object as detected by the devices 100. The signal sent by the devices 100 collectively may indicate the amount of stress being generated and/or a prediction of the amount of stress that will be generated. The stress detection module 224 may further be configured to detect a change in stress of non-smart devices associated with the unit 200.

The prediction module 226 may be configured to predict future stress based on past stress history as detected, environmental conditions, forecasted stress loads, among other factors. In some embodiments, the prediction module 226 may predict future stress by building models of usage and weight being transported. For example, the prediction module 226 may build models using machine learning based on support vector machines, artificial neural networks, or using other types of machine learning. For example, stress may correlate with the load carried by a bridge or an airplane structure. In other example, stress may correlate with temperature cycling when a structure is exposed to constant changes (such as that of an airplane).

The prediction module 226 may gather data for building the model to predict stress from multiple sources. Some of these sources may include, the first, second, and third smart devices 240, 250, 260; the stress detection module 224; networks, such as the World Wide Web; the interface module 234; among other sources. For example, the first, second, and third smart devices 240, 250, 260 may send information regarding human interactions with the first, second, and third smart devices 240, 250, 260. The human interactions with the first, second, and third smart devices 240, 250, 260 may indicate a pattern of usage for the first, second, and third smart devices 240, 250, 260 and/or other human behavior with respect to stress in the unit 200.

In some embodiments, the first, second, and third smart devices 240, 250, 260 may perform predictions for their own stress based on history and send their predicted stress in reports to the transceiver module 222. The prediction module 226 may use the stress reports along with the data of human interactions to predict stress for the system 200. Alternately or additionally, the prediction module 226 may make predictions of stress for the first, second, and third smart devices 240, 250, 260 based on data of human interactions and passed to the transceiver module 222 from the first, second, and third smart devices 240, 250, 260. A discussion of predicting stress for the first, second, and third smart devices 240, 250, 260 is provided below with respect to FIGS. 5 and 6.

The prediction module 224 may predict the stress for different amounts of time. For example, the prediction module 224 may predict stress of the system 200 for 1 hour, 2 hours, 12 hours, 1 day, or some other period. The prediction module 224 may also update a prediction at a set interval or when new data is available that changes the prediction. The prediction module 224 may send the predicted stress of the system 200 to the determination module 228. In some embodiments, the predicted stress of the system 200 may contain the entire stress of the system 200 and may incorporate or be based on stress reports from the first, second, and third smart devices 240, 250, 260. In other embodiments, the predicted stress of the system 200 may not incorporate or be based on the stress reports from the first, second, and third smart devices 240, 250, 260.

The determination module 228 may be configured to generate a unit stress report for the system 200. The determination module 228 may use the current stress of the system 200, the predicted stress of the system 200 received from the prediction module 224; stress reports from the first, second, and/or third smart devices 240, 250, 260, whether incorporated in the predicted stress of the system 200 or separate from the predicted stress of the system 200; and an amount of stress generated or the predicted amount of stress, to generate a unit stress report.

In some embodiments, one or more of the stress reports from the first, second, and/or third smart device 240, 250, 260 may contain an indication of the current operational profile and not stress. In these and other embodiments, the determination module 228 may be configured to determine the stress of a smart device for which the stress report indicates the current operational profile but not the stress. The determination module 228 may include the determined amount of stress for the smart device in the unit stress report. For example, both the first and second smart device 240, 250 may send stress report. The stress report from the first smart device 240 may indicate stress of the first smart device 240. The stress report from the second smart device 250 may indicate the current operational profile but not the stress of the second smart device 250. Based on the current operational profile of the second smart device 250, the determination module 228 may calculate the stress of the second smart device 250. The determination module 228 may then generate a unit stress report that contains the stress of both the first and second smart devices 240, 250.

In some embodiments, the stress monitoring system 220 may not include the prediction module 226. In these and other embodiments, the determination module 228 may use stress reports from the first, second, and/or third smart devices 240, 250, 260, with the received amount of stress inferred on non-smart devices, if any, to generate the unit stress report. The determination module 228 may send the unit stress report to the transceiver module 222.

In some embodiments, the processor 236 may be configured to execute computer instructions that cause the stress monitoring system 220 to perform the functions and operations described herein. The computer instructions may be loaded into the memory 238 for execution by the processor 236 and/or data generated, received, or operated on during performance of the functions and operations described herein may be at least temporarily stored in the memory 238.

Although the stress monitoring system 220 illustrates various discrete components, such as the prediction module 226 and the determination module 228, various components may be divided into additional components, combined into fewer components, or eliminated, depending on the desired implementation. In some embodiments, the unit 200 may be associated with more or less smart devices than the three smart devices 240, 250, 260 illustrated in FIG. 2.

Figure 3:
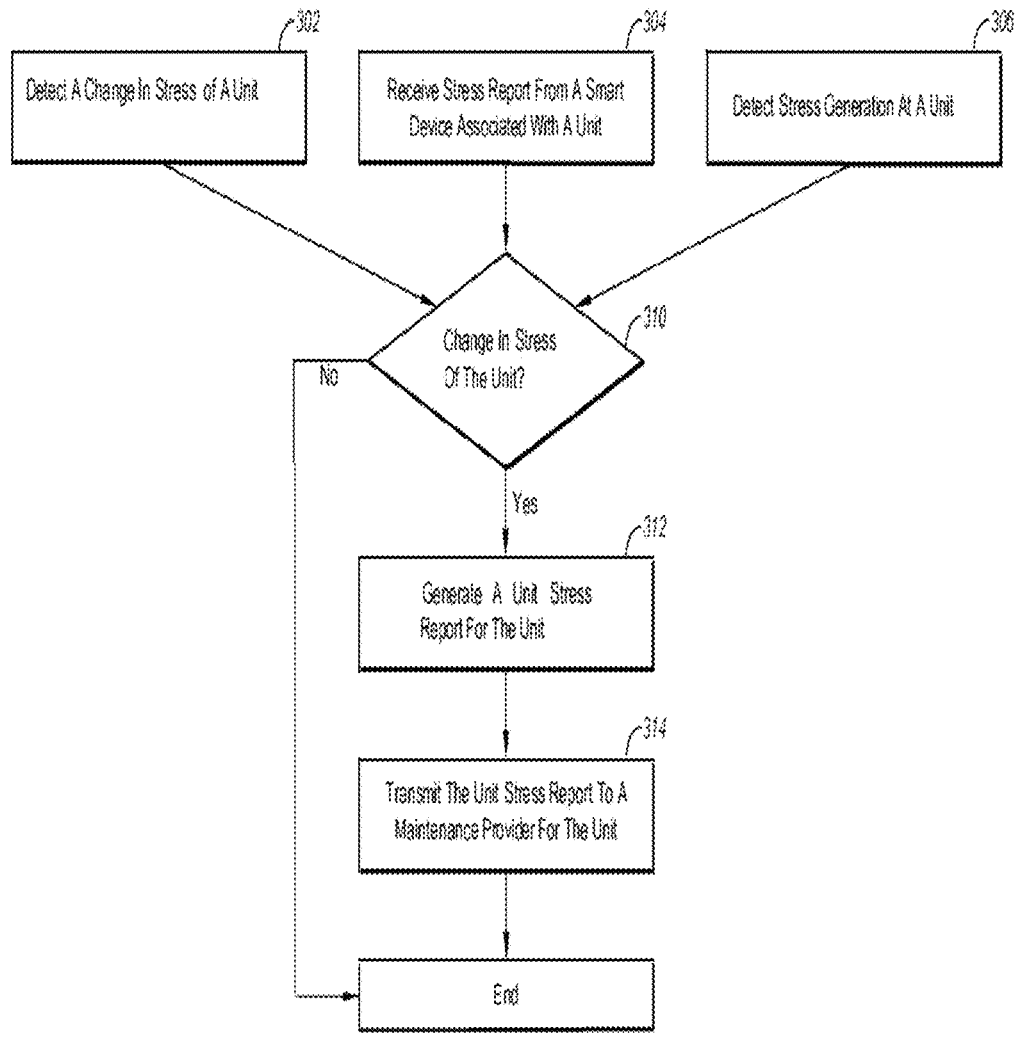
FIG. 3 is a flowchart illustrating one operation of the system of FIG. 2A-2B in detecting stress on a unit.

FIG. 3 is a flow chart of an example method 300 of monitoring stress of a sport or game unit, arranged in accordance with at least some embodiments described herein. The method 300 may be implemented, in some embodiments, by an stress monitoring system, such as the stress monitoring system 220 of FIG. 2. For instance, the processor 236 of FIG. 2B may be configured to execute computer instructions to perform operations for monitoring stress as represented by one or more of blocks 302, 304, 306, 310, 312, and/or 314 of the method 300. Although illustrated as discrete blocks, various blocks may be divided into additional blocks, combined into fewer blocks, or eliminated, depending on the desired implementation.

The method 300 may begin at one or more of blocks 302, 304, and/or 306. The blocks 302, 304, and/or 306 may occur at the same time or at different times and may or may not depend on one another. Furthermore, one or more of the block 302, 304, 306 may occur during the method 300. For example, the method 300 may complete when blocks 304, 310, and 312 occurs and without the occurrence of block 302 and 306.

In block 302, a change in stress of a device (device or beam) associated with a unit may be detected. A non-smart device may by any device that receives stress and does not generate an stress report indicating its stress, for example a legacy racket without IoT electronics. A change in the stress of a non-smart device may be detected using an stress detection module and/or usage meter associated with the unit, such as the stress detection module 224 and/or the smart device 100. For example, non-smart device stress can be estimated by the load the unit carries, the temperature cycling experienced by the unit, for example.

After a change in stress of the non-smart device is detected, the method 300 proceeds to block 310. In block 304, an stress report from a smart device such as the smart device 100 associated with the unit may be received. A smart device may be a device that detects stress and generates and transmits an stress report indicating the stress on the smart device. The stress report may indicate predicted future stress of the smart device. In some embodiments, an stress report may be received at set intervals from the smart device regardless of a change in the stress report. Alternately or additionally, a stress report may be received after a change in the stress of the smart device results in a change to the stress report. After a stress report is received from the smart device, the method 300 proceeds to block 310.

In block 306, stress experienced at the unit may be detected. Stress at the unit may be detected using a stress detection module, such as the stress detection module 224 of FIG. 2B. After detecting stress at the unit, the method proceeds to block 310. At block 310, it is determined if a change in the stress occurred. For example, if an increase in stress occurs at the same time and at the same amount as an increase in the stress of a non-smart device, a change in the stress may not occur. If a change in the stress occurs, the method 300 proceeds to block 312. If no change occurs, the method 300 ends.

At block 312, a unit stress report is generated for the unit. In some embodiments, the unit stress report may indicate the current stress of the unit. Alternately or additionally, the unit stress report may indicate a current and predicted future stress of the unit. At block 314, the unit stress report is transmitted to a maintenance provider. In some embodiments, the unit stress report may be transmitted when the unit stress report indicates a change in stress for the unit that is greater than a predetermined threshold. If the unit stress report indicates a change in stress for the unit that is less than the predetermined threshold, the unit stress report may not be transmitted to the provider of maintenance services.

Figure 5:
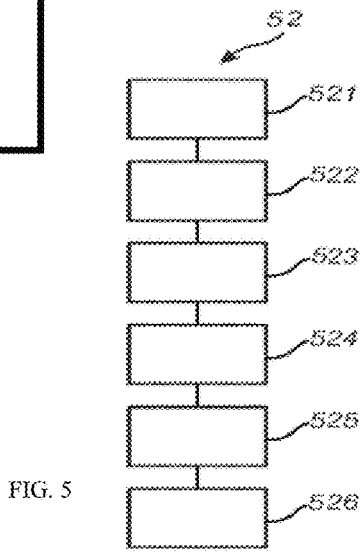
FIG. 5 shows an exemplary process for augmented and/or virtual reality for viewers participating in a game.

FIG. 5 shows in more details the computer 30 and the interface to the probe 20. An amplifier 90 amplifies vibratory output from a transducer 92. A pick up unit having an accelerometer (or an array) 96 receives reflected vibrations from user arm or leg 94, among others. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the athlete.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the arm or leg and down is root into the soft tissues and out into the bones or jaws. The accelerometer or detector will be placed on the bone of interest. It will receive the vibrations from the emitter. The effect of the vibrations on the muscle of interest will generate a pattern of frequency vibrations. Those vibrations will be digitally converted and analyzed against known dental states in the software of the computer. As the data is collected various linear samplings and comparisons will be made against the database. Software will make these comparisons as the data is received from the teeth.

FIG. 5 schematically shows a method or app 52 to perform collaborative VR/AR gaming. The app 52 includes code for:

(51) capture 360 degree view of the live event
(52) detect head position of the viewer
(53) adjust viewing angle on screen based on head position and user posture
(54) render view to simulate action based on user control rather than what the professional is doing
(55) augment view with a simulated object that is powered by viewer action as detected by sensors on viewer body
(56) compare professional result with simulated result and show result to a crowd of enthusiasts for social discussion.

Figure 4:
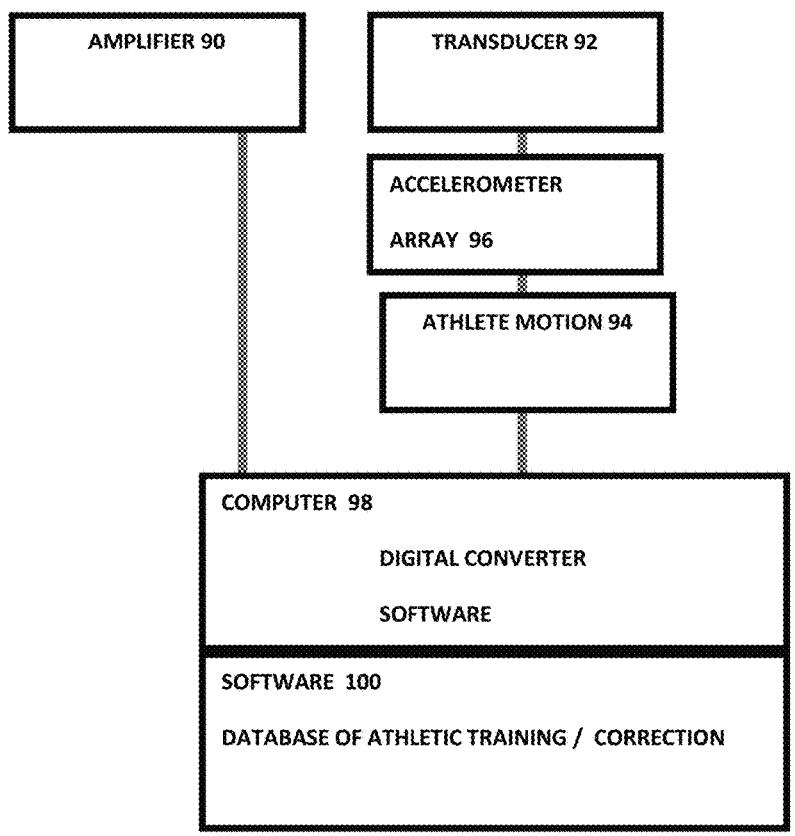
FIG. 4 shows an exemplary sports diagnosis and trainer system for augmented and/or virtual reality.
Figure 6:
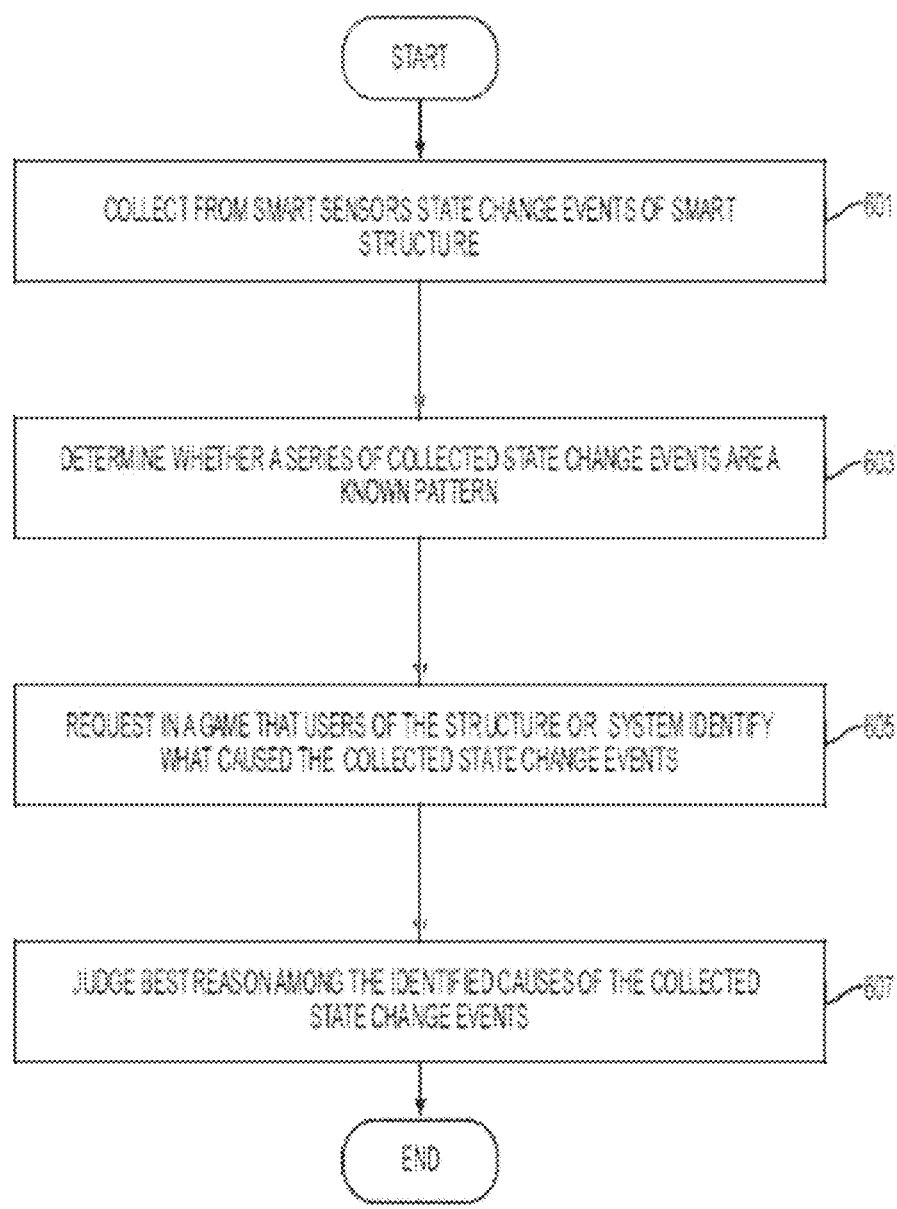
FIG. 6 shows an exemplary process to identify reasons for sensor data changes using a gaming process.

FIG. 6 is a flowchart of a method of an embodiment of the present disclosure. Referring to FIG. 6, a smart system may collect from smart devices state change events of a smart system in operation 601. That is, the smart system of FIG. 4 collects information on each of the group of devices, the smart devices, the smart appliances, the security devices, the lighting devices, the energy devices, and the like. The state change events indicate when there is a change in the state of the device or the surrounding environment. The state change events are stored by the smart system. In operation 603, the system may determine whether a series of the collected state change events are a known pattern. That is, the gateway determines whether there are events which have been correlated or identified in the past. If the collected state change events have been identified in the past, it may be necessary to determine that the smart systems trusts the identification the collected state change events. The trust factor of the identification of the collected state change events may be determined by the number of users who have identified the collected state change events or the number of time collected state change events have been repeated and identified. In operation 605, when the series of the collected state change events is an unknown pattern, request users of the smart system to identify what caused the collected state change events request. That is, the system transmits to a gamification application (hereinafter app) on the user's mobile device a request to identify the collected state change events. The gamification app displays the information and request the user enter information identifying the collected state change events. Each of the mobile devices transmits this information back to the system to the gamification module. In operation 605, the system transmits the each user's identified collected state change events to the other user's of the smart home system and they each vote on the best identification of the collected state change events. Thus, the identified collected change state events that have been repeatedly identified over a period of weeks increases, the trustworthiness of the identification increases. Likewise, if every user of the smart system makes the same identification of the collected change state events, the identified collected change state events may be considered trustworthy at point. Such a determination of a threshold for when the identified collected change state events are considered trustworthy and therefore need not be repeated, is made by a system administrator. However, it will be understood that such a trustworthiness of this type only gives higher confidence of this particular dataset at that point in time. As such further repetition is required, since the sensor data may have noise, the more datasets to be identified to the pattern, the more robust the trustworthiness will be. Until the robustness reaches a threshold, then the system can confirm this is a known trustworthy pattern.

The system can use gaming to help sport enthusiasts improve dental care or maintain teeth hygiene. This may involve use of virtual tools, corresponding to such tools used in normal dental hygiene: sport device, tooth picks, dental floss, gum massaging aids, etc. In this embodiment, the game may, for example, have the object of fighting tooth or gum decay, damage or infection which may be caused by carries or other infectious agents. The user is presented with a library of tools and has to select a tool to treat a certain developing virtual condition, e.g. carries or a gum infection. The game rules determine a certain continuous progress of infection which if not properly "treated" by the user will cause decay of one or more teeth, gum infection, potential bleeding, loss of teeth, etc. In step 13, the user may score points depending on his ability to choose the right tools to treat a particular condition or in avoiding a condition from developing. Next, it is determined whether the condition of the teeth is satisfactory. If yes, the process terminates. If no, then the user is prompted whether he wishes to select another tool. If no, the process terminates. If yes, the process restarts. Here again, the game, in addition to being amusing and providing an insight of the user into his own teeth, may be educational, particularly for children, on teeth oral hygiene methods and on the importance of maintaining oral hygiene.

In accordance with another embodiment of the invention the game may involve use of a variety of virtual imaginary tools such as virtual guns, wands, etc. in order to fight infectious agents of the teeth or gums.

Smart Sport Glove

FIG. 7 shows an exemplary glove which can be thin to provide touch sensitivity or thick to provide shock protection for boxers. A body 12 of the boxing glove 10 includes an impact measuring device 14 is embedded within the glove 12 in an area protected from direct impact. Such an area includes the cuff 15 of the glove 12 or that portion of the glove 12 adjacent a user's palm, or adjacent an inside surface of a user's fingers. Placement of the impact measuring device 14 into the lining of the glove in such an area allows for the force of a blow to be measured without presenting a hazard to the recipient of the blow. Under the embodiment, an impact measuring device 14 would be included in the right glove 12 for a right handed fighter, or the left glove 12 for a left handed fighter. For fighters that are equally effective with both hands, or to improve monitoring accuracy, an impact measuring device 14 would be included in both gloves 12. The impact measuring system 20. The impact measuring system 20 includes an impact measuring device 14 and impact display unit 16. The impact measuring device 14 is linked to the impact display 28 via a radio frequency (rf) link 32. Under the embodiment, the impact measuring device 14 includes at least one 3-axis accelerometer. A thin version of the glove can be worn to detect a golf stroke or a tennis stroke with legacy clubs or rackets that lacks IoT intelligence.

Smart Sport Band

FIG. 8 shows an exemplary stick on wearable monitoring device for sports and fitness applications. The wireless sensor electronics 14 is mounted on a band-aid in the example of FIG. 8. The band-aid can be removed upon completion of the sports event. The central patch can be recycled, and the adhesive portion can be disposed. While the embodiment is shown as a band-aid, the inventors contemplate that any suitable bands, straps, attachments can be used in lieu of the band-aid to attach the sensors to the body. For example, in Virtual Reality (VR) sports applications, sensors including gyroscopes and cameras can be positioned on various body portions to capture motion as well as eye tracking, mouth tracking, speech recognition, among others.

One embodiment uses Samsung's Bio-Processor which is an all-in-one health solution chip. By integrating not only Analog Front Ends (AFE), but also microcontroller unit (MCU), power management integrated circuit (PMIC), digital signal processor (DSP), and eFlash memory, it is able to process the bio-signals it measures without the need of external processing parts. Even with its integrated design, the Bio-Processor is particularly innovative thanks to its incredibly small size. When compared to the total area of the discrete parts, the Bio-Processor is only about one fourth of the total combined size, which is ideal for small wearable devices, offering a bounty of options when designing new devices. The Bio-Processor has five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively.

One embodiment provides a flexible and stretchable electronic patch that monitors impact or other events whereby a flexible substrate is geometrically patterned to allow the substrate to undergo substantial stretching and flexing while large regions of the substrate material experiences local strains much lower than the macroscopic applied strain. The geometric patterning of the substrate facilitates continuous low strain domains (LSDs) throughout the substrate—where low strain domains are defined as regions that experience strain levels (magnitude) lower than the macroscopic applied strain. Conventional electronic components can be mounted to the LSDs, and conventional metal traces can be routed through the LSDs, dramatically reducing the stresses transmitted to the components and traces by the substrate during stretching and flexing, and therefore reducing the potential for component debonding, trace cracking, and circuit failure. The geometrically patterned strain relief features (SRFs) are dispersed either regularly or irregularly throughout the substrate. The geometrically patterned SRF regions form "hinge-like" domains. During macroscopic deformation, the SRFs rotate, translate, open, close, or otherwise change shape, causing the "hinge-like" regions to deform, and the remaining larger LSD substrate regions to primarily rotate and translate. The SRFs are designed such that the "hinge-like" regions also exhibit relatively small strain compared to the macroscopic applied strain and thus enable conductive traces, such as copper or gold, to run through the hinges and maintain function during stretching, flexing and twisting of the patch. The substrate can be multilayered to enable running conductive traces, ground layers, vias, and/or components on/in multiple layers through the thickness of the overall substrate. The geometric patterning can be designed to enable different stretching, flexing and twisting, providing uniaxial, biaxial, and multi-axial stretchability or flexibility, and the ability to conform to a variety of surface curvatures. The geometrically patterned substrate offers a means of packaging complex multi-layered electronics designs for monitoring impact (and other) events onto a stretchable and flexible substrate enabling the device to dynamically stretch, bend, twist, and conform to arbitrary shapes. The stretchable, flexible geometrically structure electronics can be fabricated using the same technologies for conventional flexible circuit boards where the stretch-enabling patterning can be imparted at different stages in the fabrication process and can also be fabricated using emerging materials and fabrication methods. The Stretchable bandaid has the stretchable, flexible substrate described above with multiple LSDs for placement of electronic components (e.g., accelerometers, gyroscopes, pressure temperature, gas and fluid sensors, microprocessors, transceivers, GPS, clocks, actuators, vias, and batteries (or other energy source)) and multiple patterned hinge-like regions bridging the LSDs which enable the routing of conducting interconnecting traces. The SEHIM patch can take the form factor of a bandaid or bandage or other such wearable form factor. The geometric patterning provides stretch, flex and twist to conform to a body and stretch, flex and twist to move or deform with a body. The bandaid detects impact accelerations, using a 3-axis accelerometer and processes the raw acceleration data in the microprocessor. The processed data is stored in the microprocessor and later (or potentially in real time) transmitted via the Bluetooth to a smart phone, tablet or computer. This embodiment encompasses wireless communication but wired communication may be desirable in some applications and can be accommodated by this invention. The bandaid can be stretched, bent and twisted with the traces and components at low strains to maintain electrical function. In all cases there was effectively no strain on the components and solder joints. The bandaid can also possess an adhesive backing for direct adhesion to the head, body or object. The band can also be coated to provide both added comfort and protection against moisture, water, and other environmental factors. The band can also contain other sensors including gyroscopes, temperature and pressure sensors, moisture sensors, clocks, chemical and/or biological sensors, etc.

Smart Clothing

FIG. 9 shows an exemplary shirt based embodiment where sensors can be positioned anywhere on the shirt and when worn, can capture position, video, and vital signs. One embodiment uses Samsung's Bio-Processor to process the bio-signals it measures without the need of external processing parts with five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. Features of the smart clothe can include:

1. A smart clothing, comprising:
    a shirt, underwear, pant or sock;
    a band to be secured to the a shirt, underwear, pant or sock;
    a processor in the band and coupled to a wireless transceiver;
    an EKG amplifier coupled to the band;
    a sensor disposed in the band; and
    an accelerometer disposed within the band to detect acceleration of the band.

2. The clothing of claim 1, comprising a plurality of bands forming a mesh network and communicating episodically to conserve power.
3. The clothing of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).
4. The clothing of claim 1 comprised for sensing and/or monitoring impact events where the sensors are accelerometers, gyroscopes, and/or pressure sensors.
5. The clothing of claim 1 comprised for sensing and/or monitoring and/or controlling ongoing events where the sensors monitor temperature, temperature gradients, motion, position, environmental or chemical levels, or other such information.
6. The clothing of claim 1 comprised for sensing events or other information including mounting multiple distributed sensors for obtaining spatial and/or temporal distribution in the data and/or multiple sensors sensing different information and data.
7. The clothing of claim 1 including wired or wireless communication, such as a Bluetooth module or a wi-fi module or other transmission module, transmitting and/or receiving information to/from another device.
8. The clothing of claim 1 with power and energy sources including batteries, wired or wireless rechargeable batteries, photovoltaics, thermoelectrics, or energy harvesters.
9. The clothing of claim 1 with an adhesive backing for directly adhering to a head, a body, or an object.
10. The clothing of claim 1 contained in an adhesive or a sleeve for adhering or attaching to a head, a body, or an object.
11. The clothing of claim 1 coated with a coating for protection against the elements (water, moisture, dirt, other) and/or for increased comfort to the wearer.
12. The clothing of claim 1, comprising a geometrically patterned substrate that contains regions of low strain domains (LSDs) bridged by hingeable strain relief features (SRFs) which also contain low strain regions and enable the stretching, flexing and twisting of the patch while maintaining continuous low strain regions for mounting electronic components and routing traces.
13. The clothing of claim 1 for attachment to or on or an object, or embedded in an object.
14. The clothing of claim 1 in the form factor of a rectangular or a square or a triangular or other polygon or circular or elliptical or other geometric shape bandage.
15. The clothing of claim 1 in the form factor that is or contains any combination of rectangles, triangles, circles, ellipses or other form factors.
16. The clothing of claim 1 with different geometric patterning of different numbers and shapes and orientations of low strain domains, different numbers and orientation of geometrically structured hinge-like domains, and different geometries of hinge-like domains.
17. The clothing of claim 1 as a programmable circuit board for arbitrary applications.
18. The clothing of claim 1 fabricated using current flex circuit manufacturing methods and materials.
19. The clothing of claim 1 comprising a cloud storage to receive sensor data.

20. The clothing of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Handle

Figure 11A:
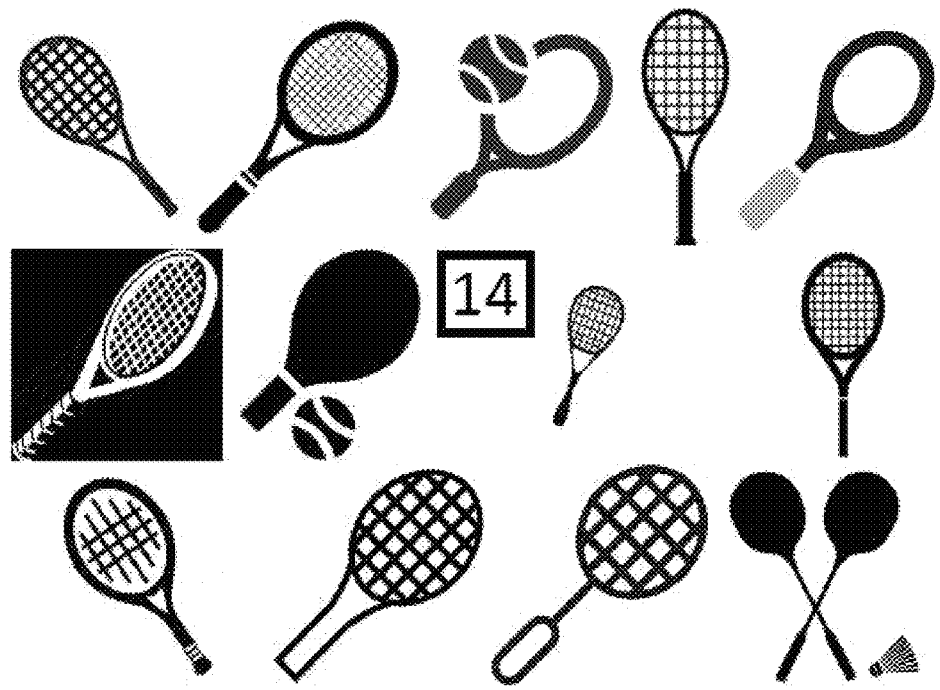
Figure 11B:
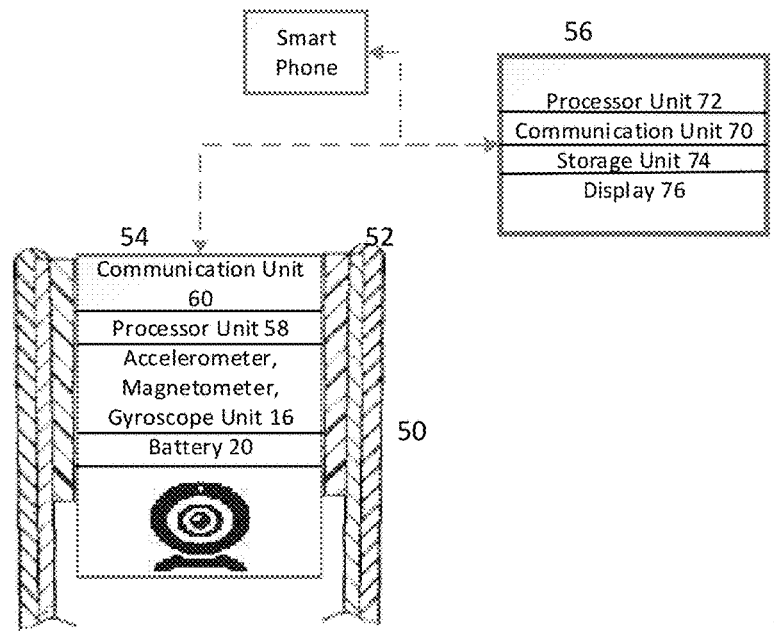
FIG. 11B shows electronics in the handle for golf clubs, rackets, or kung fu sticks.

FIGS. 11A-11B show an exemplary smart handle for sports such as tennis, badminton, table tennis, and golf, among others. The wireless sensor electronics 14 is mounted on a handle in the example of FIG. 11B. The handle can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The handle includes a swing analyzer measurement portion 54 in the grip end 52 of the handle of a golf club or a tennis/badminton racket, and a remote or handheld unit 56. The swing analyzer measurement portion 54 includes an accelerometer 16 of combination accelerometer and gyroscope or magnetometer unit, a processor unit 58 coupled to the accelerometer 16, and a battery 20 that is electrically coupled to and provides power to the accelerometer 16 and processor unit 58. A camera is included to capture videos of the swing and also the game in progress for future reference. A communications unit 60 is also housed in the grip end 52 of the golf club 50, receives power from the battery 20, and is coupled to the processor unit 58. Swing analyzer measurement portion 54, with or without the communications unit 60, may be assembled as an integral unit and inserted into a hollow portion of the handle of the golf club or tennis/racket handle 50 at the grip end 52 thereof. Processor unit 58 may be an integrated device that includes hardware and software components capable of processing acceleration measured by the accelerometer(s) 16 and converting the measured acceleration into data about the force on the shaft and position of the face of the club at impact at a set distance. If the measured force exceeds a threshold the measured force or a signal derived therefrom is transmitted via the communications unit 60 to the handheld unit 56. If not, acceleration and face position at impact of the golf club or tennis racket handle 50 is obtained again. The threshold is set so that only acceleration or force measurements arising from actual swings of the golf club 50 are transmitted to the handheld unit 56. Handheld or remote unit 56 includes an application or computer program embodied on a non-transitory computer-readable medium that performs the golf ball carrying distance estimation or prediction steps, as well as manages the training stage described above. Importantly, the handheld unit 56 receives acceleration measurement data from the golf clubs/tennis rackets equipped with a swing analyzer measurement portion 54 and the club face angle in relation to the swing plane, and manages the carrying distance estimation steps for all golf clubs equipped with the swing analyzer measurement portion 54 that are designed to communicate therewith. Handheld or remote unit 56 may be a standalone unit for use only with the golf clubs equipped with the swing analyzer measurement portion 54, and incorporating the application thereon, or may be a smartphone or similar device with the application embodied thereon or downloaded thereto and that can be used for other purposes. Handheld or remote unit 56 includes a communications unit 70 that communicates with the communications unit 60 on each golf club or tennis racket handle 50, i.e., with the communications units present on all of the golf clubs 50 equipped with swing analyzer measurement portions 54 and which have been designated to communicate therewith. Communications unit 70 may be an integral part of the handheld unit 56 as is the case when the handheld unit 56 is a smartphone. Communications unit 70 may also communicate with another device such as a Smartphone, to perform more data manipulations relating to the golf swing and/or swing results to provide more information to the user. The data and the calculation/manipulation results can be stored in the Smartphone and displayed when desired. Currently usable Smartphones are Apple iOS iPhones and Android operating system phones. Handheld or remote unit 56 also includes a processor unit 72, a storage unit 74 and a display 76. When the handheld unit 56 is a smartphone or similar device, all of the processor unit 72, storage unit 74 and display 76 may be integral components thereof. Processor unit 72 performs functions similar to those performed by the processor unit 18 described above, e.g., calculates an estimated carrying distance for the golf ball based on the acceleration measured by the accelerometer(s) 16 and transmitted via the communications units 60, 70, and the type of club provided to the application or computer program in the processor unit 72. Storage unit 74 receives and stores information about the carrying distance of each club as a function of clock or swing position, e.g., in the form of a virtual table associating the type of club, the swing or swing position and the estimated carrying distance.

Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc. Features of the smart handle can include:

Smart Protective Gear

Figure 12A:
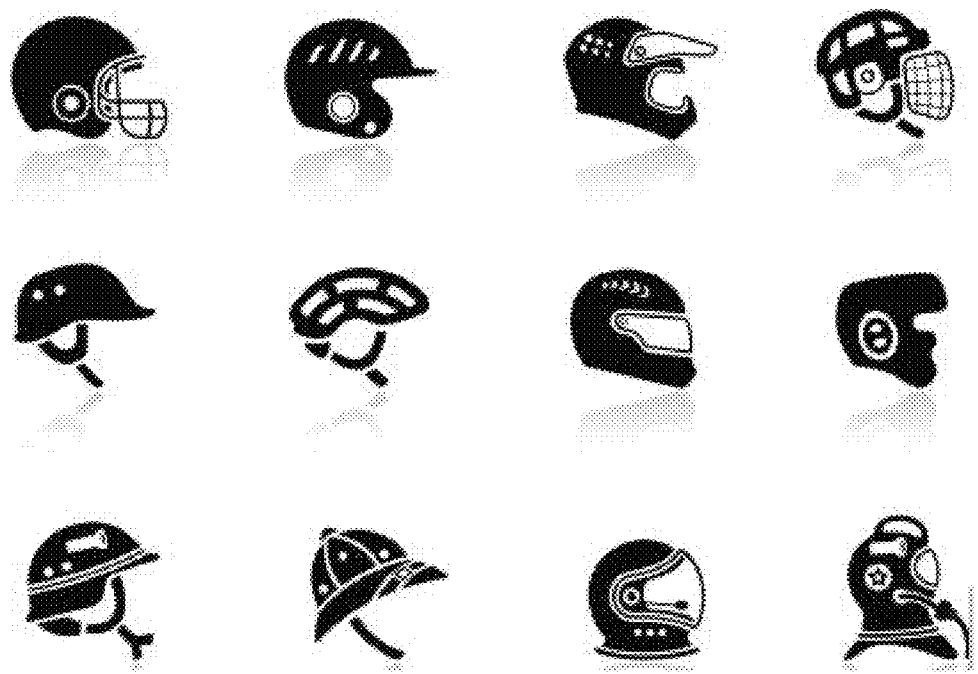
Figure 12C:
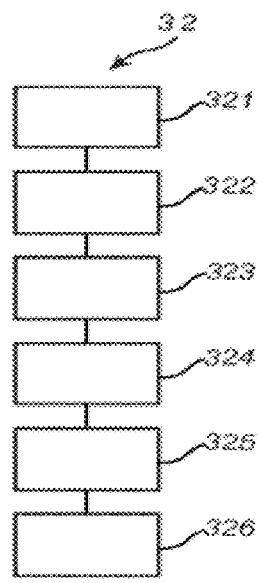
FIG. 12C shows an exemplary process to fabricate mass-customized protective gear.
Figure 12B:
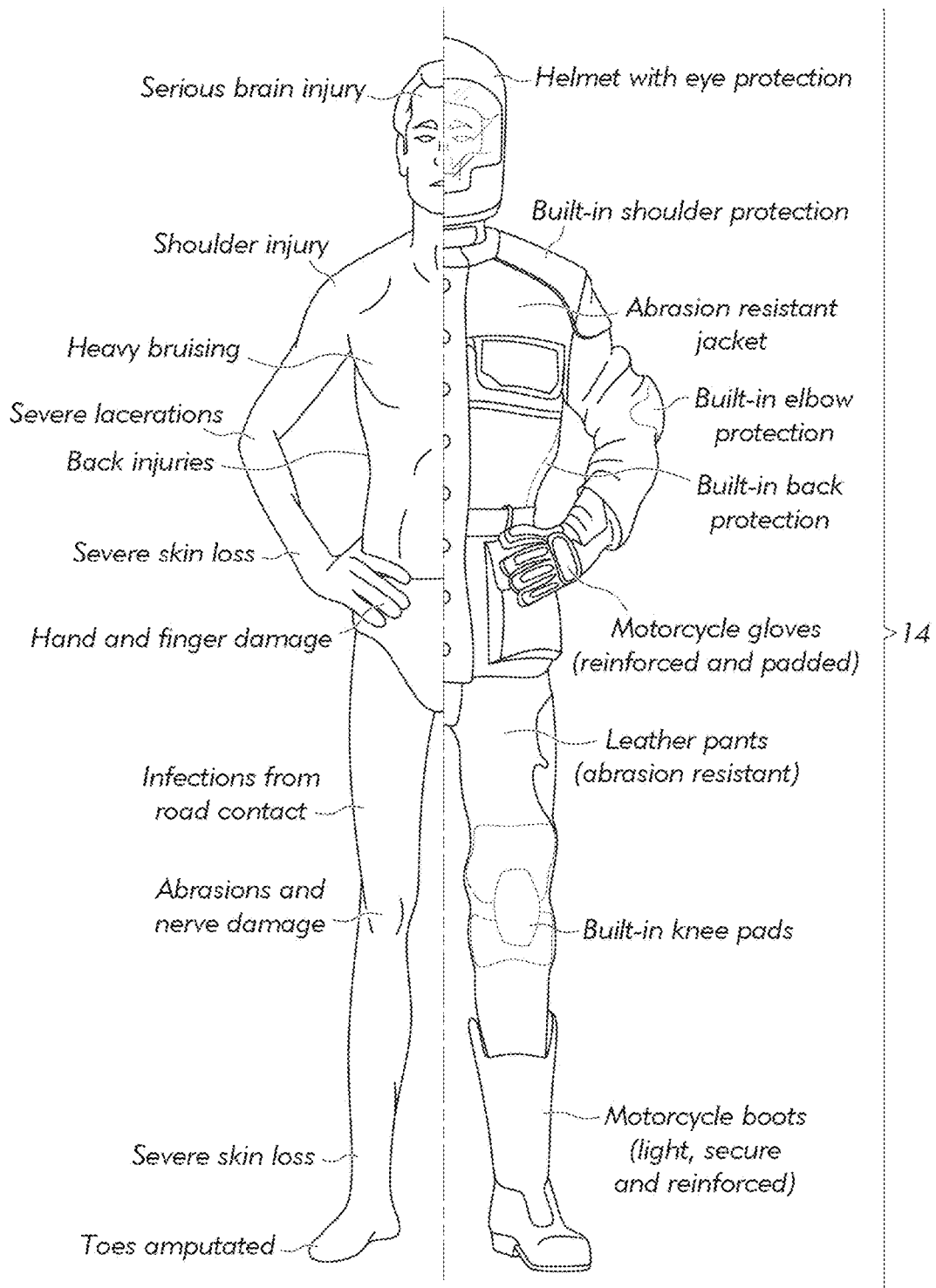

FIGS. 12A-12C illustrate smart protective gears embedded with the IoT sensors and instrumentations to report potential health issues. For soccer, the protection includes shin guards. For football, the protection includes Helmets, Chin Straps & Chin Shields, Cups & Athletic Supporters, Elbow Sleeves & Arm Pads, Back Plates & Rib Protection, Facemasks, Girdles, Helmet Visors, Shoulder Pads, Hip & Tail Pads, Mouthguards, Neck Rolls. For motorcycling, the protection includes helmet, should pads, jacket with back protection, padded gloves, leather pants, knee pads, and boots. For rock climbing, the protection includes shoes, carabiners, webbing, harnesses, among others.

The wireless sensor electronics 14 is mounted on the helmet or shoulder pad in the example of FIG. 12A or 12C. The electronics 14 can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The protection gear includes an impact sensor such as an accelerometer to indicate if concussion has occurred. Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc.

Impact sensors, or accelerometers, measure in real time the force and even the number of impacts that players sustain. Data collected is sent wirelessly via Bluetooth to a dedicated monitor on the sidelines, while the impact prompts a visual light or audio alert to signal players, coaches, officials, and the training or medical staff of the team. One such sensor example is the ADXL377 from Analog Devices, a small, thin and low-power 3-axis accelerometer that measures acceleration from motion, shock, or vibration. It features a full-scale range of ±200 g, which would encompass the full range of impact acceleration in sports, which typically does not exceed 150 g's. Specifically designed for concussion and head-trauma detection, at 3 mm×3 mm×1.45 mm, the device is small enough to be designed into a helmet. Sensitivity, listed at 6.5 mV/g with −3 dB bandwidth at 1.6 kHz, is sufficiently high for the application. When a post-impact player is removed from a game and not allowed to return until cleared by a concussion-savvy healthcare professional, most will recover quickly. If the injury is undetected, however, and an athlete continues playing, concussion recovery often takes much longer. In addition, the industry is finding that long-term problems from delayed or unidentified injury can include: Early dementia, Depression, Rapid brain aging, and Death. The cumulative effects of repetitive head impacts (RHI) increases the risk of long-term neuro-degenerative diseases, such as Parkinson's disease, Alzheimer's, Mild Cognitive Impairment, and ALS or Lou Gehrig's disease. The sensors' most important role is to alert to dangerous concussions. Yet, the act of real-time monitoring brings these players to the attention of their coaches not only to monitor serious impacts but, based on the data provided by the sensors, also help to modify a player's technique so that they are not, for example, keeping their head low where they can sustain injury to the front and top of the skull. In the NFL there also has been an aggressive crackdown against hits to the head and neck—a response to the ongoing concussion crisis—resulting in immediate penalty to players using their helmets as a "weapon". Customized mouthguards also have sensors therein. A customized mouthguard has tested to be 99 percent accurate in predicting serious brain injury after near-concussive force, according to an Academy of General Dentistry study2. Teeth absorb and scatter infrared light, which shows how much force is taking place at the moment of impact.

Features of the smart protective gear can include:
1. A smart protection gear, comprising:
   a wearable surface;
   a processor in the band and coupled to a wireless transceiver;
   a camera coupled to the surface;
   a sensor disposed in the surface; and
   an accelerometer disposed within the band to detect acceleration of the surface.

2. The protection gear of claim 1, comprising a plurality of smart protection gears forming a mesh network and communicating episodically to conserve power.
3. The protection gear of claim 1 where the electronic components, sensors, and interconnects of the protection gear monitor, record, process and/or transmit events of interest (such as accelerometers and gyroscopes for impact events, temperature sensors for temperature and/or temperature gradients, pressure sensors, moisture sensors, chemical sensors).
4. The protection gear of claim 1 comprised for sensing and/or monitoring impact events where the sensors are accelerometers, gyroscopes, and/or pressure sensors.
5. The protection gear of claim 1 comprised for sensing and/or monitoring and/or controlling ongoing events where the sensors monitor temperature, temperature gradients, motion, position, environmental or chemical levels, or other such information.
6. The protection gear of claim 1 comprised for sensing events or other information including mounting multiple distributed sensors for obtaining spatial and/or temporal distribution in the data and/or multiple sensors sensing different information and data.
7. The protection gear of claim 1 including wired or wireless communication, such as a Bluetooth module or a wi-fi module or other transmission module, transmitting and/or receiving information to/from another device.
8. The protection gear of claim 1 with power and energy sources including batteries, wired or wireless rechargeable batteries, photovoltaics, thermoelectrics, or energy harvesters.
9. The protection gear of claim 1 with an adhesive backing for directly adhering to a head, a body, or an object.
10. The protection gear of claim 1 contained in an adhesive or a sleeve for adhering or attaching to a head, a body, or an object.
11. The protection gear of claim 1 coated with a coating for protection against the elements (water, moisture, dirt, other) and/or for increased comfort to the wearer.
12. The protection gear of claim 1, comprising a geometrically patterned substrate that contains regions of low strain domains (LSDs) bridged by hingeable strain relief features (SRFs) which also contain low strain regions and enable the stretching, flexing and twisting of the protection gear while maintaining continuous low strain regions for mounting electronic components and routing traces.
13. The protection gear of claim 1 for attachment to or on or an object, or embedded in an object.
14. The protection gear of claim 1 in the form factor of a rectangular or a square or a triangular or other polygon or circular or elliptical or other geometric shape bandage.
15. The protection gear of claim 1 in the form factor that is or contains any combination of rectangles, triangles, circles, ellipses or other form factors.
16. The protection gear of claim 1 with different geometric patterning of different numbers and shapes and orientations of low strain domains, different numbers and orientation of geometrically structured hinge-like domains, and different geometries of hinge-like domains.
17. The protection gear of claim 1 as a programmable circuit board for arbitrary applications.
18. The protection gear of claim 1 fabricated using current flex circuit manufacturing methods and materials.

19. The protection gear of claim 1 comprising a cloud storage to receive sensor data.

20. The protection gear of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are conductive inks.

Custom Gear

In one aspect, the protective gear is custom formed to the athlete's body. This is done in FIG. 12C as follows:
321) perform 3D scan of person and create 3D model
322) form positive mold from the 3D model
323) place mold into 2 phase 3D printer to form a negative
324) put composite material into mold and form composite protection gear
325) embed IoT electronics into one or more locations into the composite protection gear
326) link IoT electronics with mobile devices and cloud based storage and process impact data and warn user if impact is unsafe.

The protection gear or footwear can be custom produced at the request of a customer, who can specify the nature of the customization for one or more pairs of helmet, protective gear, or footwear. Each helmet of the footwear may have a different design, message or message portion designed into it and rendered using the bed of pins described below to make the custom helmet or shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

Shock Protection

In one embodiment, the sole is not completely filled with material, but is formed as a lattice structure. The system generates triangulated surfaces for export to additive manufacturing (AM) processes. Implementing a process that coverts a CAD object into an image, known as voxelisation, the company uses an image-based method which allows designers to generate implicitly defined periodic lattice structures suitable for additive manufacturing applications and finite element analysis (FEA). The system generates robust lattice structures can overcome the problems faced with hollowing out a part to reduce weight and optimize designs prior to 3D printing. Cellular lattice structures can be used to replace the volume of CAD and image-based parts, reducing weight whilst maintaining optimal performance. In this way, the shoes can be light weight yet strong and provide shock impact absorption during running for the wearer.

Topology optimization can be used to drive the material layout including the lattice regions. From this new topology optimization implementation, the system can identify void regions in the design space, where the material can be removed, regions where solid material is needed, and regions where lattice structure is required. This allows the system to generate the optimal hybrid or blended solid-lattice design based on desired functionality of the part.

Lattice structures can be considered as porous structures. In the case of topology optimization, the semi-dense elements are like the porous media. To refine the design, a second-phase involves a detailed sizing optimization where the end diameters of each lattice cell member are optimized. This allows for further weight reduction while meeting design requirements, such as buckling, stress, and displacement.

A piezo material can be actuated to generate a vibration that cancels incoming shock on the wearer. In one embodiment, the system tracks the shock such as the foot contact patterns and generates an anti-vibration signal to cancel the shock generated when the foot contacts the ground. In this embodiment, a processor receives foot ground contact using an accelerometer. The stride pattern is determined, and the next foot ground contact is detected, and the piezo material is actuated with a counter signal to cancel the expected shock. This is similar to the noise cancellation, except the vibration/shock is canceled.

In one hybrid embodiment, the shoes incorporate passive and active isolation elements. The passive component consists of springs which support the load weight and provide isolation over a broad spectrum. These springs provide a basic level of isolation in the lower frequencies and excellent isolation in the higher frequencies (above 200 Hz). They also support the load while allowing for travel of the actuators in the active component. The performance of the springs is augmented and corrected by an active isolation component. The active isolation component consists of vibration sensors, control electronics, and actuators. The vibration sensors are piezo accelerometers. A plurality of sensors in each isolation system are positioned in different orientations to sense in all six degrees of freedom. The piezo accelerometers convert kinetic vibration energy into electrical signals which are transmitted to the control electronics. The electronics reconcile and process the signals from the various sensors using a processor. The electronics then send a cancellation signal to the actuators. The actuators generate vibrations that are equal to the incoming vibrations but out of phase in relation to the incoming vibrations. This results in cancellation of the incoming vibrational noise, leaving the wearer undisturbed. This process occurs within 5-20 milliseconds of a vibration entering the system.

Smart Kitchen

Figure 13A:

FIG. 13A shows an exemplary kitchen system that communicates with the Internet and interoperates with each other to provide the best home experience for consumers. The system includes Internet enabled cooking products such as ranges, dishwashers, disposers and compactors, water filters, hoods and vents, grills, food processors, blenders, refrigerators, slow cookers and multi-cookers, stand mixers, coffee makers, waffle bakers, toasters, microwave ovens, and countertop ovens, among others. These appliances communicate over a wireless network such as WiFi, Zigbee, or Bluetooth, for example.

Cameras and sensors can be used in these exemplary IOT appliances to provide intelligence. In one embodiment, an acoustic sensor listens to the sound of popping and when that slows down it reduces or stops heat energy being applied to the item being cook. The appliances can have "Doneness" sensors that are supposed to determine when your food is done. One sensor is a humidity sensor that is based on the generation of moisture vapor from the food, and the humidity sensor then shuts off the microwave one a certain level of humidity is reached inside the cooking cavity. Another type is a temperature sensor that is actually a temperature probe that plugs into the receptacle in the wall of the oven and manually pushed into the food to measure the temperature. The user then sets a finish temperature, let's say 160° F. for meat or poultry, and when the temperature is reached the oven shut off. The camera can determine the color of the item being cooked, and when a particular color is reached, the camera can change the temperature of the oven for optimum flavor/taste, among others. The camera can be used in the dish washers to detect difficult spots to be washed and aim additional cleaning power to the difficult spots. The camera can also inspect the food or clothing and move the food or clothing to provide better cooking or cleaning power for the specific item's configuration, for example.

An electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result. The nose can be used in ovens to detect proper cooking targets to adjust and/or shut off temperature in the oven. The nose can be used in refrigeration chambers to detect malodors indicating rotting food that needs removal. Similarly, the nose can be used in disposers and compactors to detect malodors indicating rotting food that needs removal. In the garage, a CO sensor can be used to detect harmful air. The nose can detect baking/cooking activities in the oven and automatically adjust the speed of the fan in the hood/vent to remove food smell from the house. The nose can be used in the ovens, slow cookers, grills, countertop ovens, microwave ovens, toasters, waffle bakers, coffee makers, or even refrigerators.

An electronic tongue sensor can be provided to sense quality of food and/or water. The tongue includes a stirring module, a liquid molecule sensor module, a control unit and an output unit. The stirring module is used to pump liquid actively to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of food or liquid, among others. The tongue can be used in the ovens, slow cookers, grills, countertop ovens, microwave ovens, toasters, waffle bakers, coffee makers, food processors, blenders, mixers, or refrigerators.

A fullness sensor can be used to compact the disposers and/or signal the user to remove the full trash container, for example. The water filters can have sensors that detect end of life for the filters.

A voice sensor can be used to interface the appliance with the user. User speech is encoded into a compact digital form which is communicated with a server, loaded with a series of models honed to comprehend language. The user speech may be evaluated locally, on the appliance. A recognizer installed on the mobile device communicates with that server in the cloud to gauge whether the command can be best handled locally—such as if the user wanted a particular cooking temperature—or if it must connect to the network for further assistance. The server compares the user speech against a statistical model to estimate, based on the sounds spoken and the order of the verbal command, what letters might constitute it. (At the same time, the local recognizer compares the speech to an abridged version of that statistical model.) For both, the highest-probability estimates get the go-ahead. The user speech—now understood as a series of vowels and consonants—is then run through a language model, which estimates the words that the speech is comprised of Given a sufficient level of confidence, the computer then creates a candidate list of interpretations for what the sequence of words in the user speech might mean. Thus, if the user asks for wines that may go well with a particular food being cooked, the system searches the internet for matching wines and reply.

The appliances can be remotely controlled using one or more recipes. The recipes can be manually entered, or can come from a subscription database where users pay to access content. In one embodiment, exotic food from different cultures can be downloaded and the appliance can automatically apply predetermined settings to cook food as experts would. In one embodiment with a smart blender, a prepackaged container has a plurality of chambers, each containing different materials to be blended. The recipe can specify that the chambers open in a predetermined manner, and the mixing speed can be adjusted for each material to optimize the blends to arrive at an expertly made drink.

In another embodiment for oven cooking, a prepackaged container has a plurality of chambers each containing a different ingredient to be released in a predetermined sequence and following a predetermined temperature profile. The result is a fresh food product that is significantly better than existing canned or dried food where everything is done at the factory without access to fresh ingredients.

The recipes, or other information are collected in a database on one or more servers. The server is connected to the Internet, whereupon it receives various recipes or other information from a number of computing devices or websites, which are also connected to the Internet. The received information is converted into records having a consistent record format and is stored in the database. A selection of the records picked by a user, e.g., according to a subscription, is then communicating to the blender appliance. This can be achieved by sending the selection of the records to the user's computing device which needs to also be connected to the Internet, or directly to the computing devise imbedded in the blender appliance which may also be connected to the Internet. Alternatively, the selection of the records may be stored on medium readable by the computing device imbedded in the blender, e.g., flash memory, diskettes, CDs, etc.

Once the selection of the records is loaded into or imbedded in the appliance of the invention, a choice of various criteria for organizing such a selection of records is presented on the display screen of the blender appliance, and the user, using navigational keys of the computing device imbedded in the blender appliance, chooses the criteria for sorting of the records. The records are then sorted according to the chosen criteria and the sorted records are listed on the display screen. Using the navigational keys the user chooses at least one recipe and displays it on the display screen. After viewing a chosen recipe the user may display a next or previous recipe from the sorted list of recipes using the navigational keys.

The smart appliances are able to operate with minimal human supervision. For example, if the oven detects over boiling or over cooking, the oven would automatically reduce heat to save the food being cooked. In another example, if the refrigerator detects that vegetable is rotting, the refrigerator sends a message to the owner to alert them of spoilage. The user can send an instant message to control and communicate with the appliances remotely. The user can check contents of the refrigerator, download family-pleasing recipes to the range, turn on your washer/update cycles, and command a robot vacuum to clean the living room carpet and kitchen floor. And all this can be accomplished with or without user intervention. Should problems arise with the appliance, a diagnosis helps troubleshoot issues quickly and efficiently. Other kitchen appliances include slow cookers, pasta makers, food processors, bread makers, small ovens, toaster ovens, and the like.

In one embodiment, the appliances interoperate with each other using an interoperable multivendor appliance protocol that is more than just Bluetooth/WiFi. For example, the interoperable multivendor appliance protocol allows the refrigerator to communicate with smart packages in the refrigerator and when the package is removed by the user, the cooking instructions are automatically communicated from the refrigerator to a suitable appliance, for example a blender or a microwave oven or a grill cooker.

Embodiments of the appliances provide social applications for marketing and advertising that can transform the way companies engage with customers, analyze their behavior, and optimize the impact of their interactions. Examples include location-based services, viral marketing, and mobile advertising. The IoT appliances create and implement cohesive marketing and advertising strategies across numerous and disparate channels (TV, radio, Internet, point of sale). IoE will enable companies to have a complete view of their customers (behaviors, preferences, demographic profile) and deliver individually targeted messages and offers to them on any device at the time and location where they will have the most beneficial impact. Thus, companies can react more quickly by assessing and reacting to their markets in real time; increase profits by offering pricing based on customers' situation and ability to pay; and grow revenues by bundling their offerings with other products and services based on a holistic assessment of customers' wants and needs in the comfort of their homes.

High power appliances such as ovens, washers, and refrigerators can communicate expected electrical usage back to electric utilities, and such information can improve the electric grid by automatically detecting and repairing problems, controlling electrical flows based on real-time demand, improving generator utilization, and enabling more sustainable energy sources such as wind and solar power. In one embodiment, the refrigerator precharges its cool temperature at night when energy is less expensive so that the energy consumption during the day is reduced. This is done in one embodiment by freezing salted water containers in the refrigerator side panels at night and allowing the frozen salted containers to change phase and reduce temperature as the ice thaws. Similarly, the washers can be set to run at night to reduce grid demand during the day.

A module may be further configured to handle reduced usage requests from an electricity monitoring system associated with the smart device 500. In some embodiments, the reduced usage request may direct the smart device to operate using a specific operational profile, such as a power-off, a standby, or a suspend operations profile. Alternately or additionally, the reduced usage request may contain the requested electricity reduction amount and may allow the determination module to select an operational profile to meet the requested electricity reduction. A transceiver module may be configured to send an electricity usage report to an electricity monitoring system and to receive a reduced usage request from an electricity monitoring system. The transceiver module may also be configured to send data regarding human interactions with the smart device to an electricity monitoring system for a unit with which the smart device 500 is associated. In some embodiments, the transceiver module 520 may send and receive data over a wireless network according to a given standard, such as, IEEE 802.11, IEEE 802.15, or some other standard. Alternately or additionally, the transceiver module may send and receive data over conductors used to carry electric power for a unit with which the smart device is associated.

A prediction module may be configured to predict future electricity usage of the smart device based on current and past user interactions with the smart device as collected by the interface module, predetermined electricity usage for each operational profile, operational sub-profile, and/or selected range of operations for those operational profiles and sub-profiles for the smart device, data received from an electricity monitoring system associated with the smart device, data from networks, such as the World Wide Web, and other sources of information. The data from the electricity monitoring system may include human behaviors regarding other devices that may be associated with the smart device or general human behaviors with respect to electricity usage of a unit with which the smart device is associated. The prediction module 560 may function similar to the prediction module. The prediction module may send the predicted electricity usage for the smart device to the determination module for inclusion in the electricity usage report. In some embodiments, the prediction module may predict future electricity usage by building models of electricity usage of the smart device. For example, the prediction module may build models using machine learning based on support vector machines, artificial neural networks, or other types of machine based learning using the above-described types of data.

As an example of the operation of the prediction module, the prediction module may determine a predetermined electricity usage for a selected operational profile and range of operation for the smart device. Based on past user interactions, the prediction module may predict that the user may not have the smart device perform the selected operational profile for the full range of operation. The prediction module 560 may reduce the electricity usage from the predetermined amount accordingly.

For example, the smart device may be a microwave. The user may select a cooking time of one minute. Historically, when a user selects a cooking time of one minute, the user may stop the microwave after only 15, 30, or 45 seconds. The prediction module may predict that the user will stop the microwave before the microwave operates for the full one minute and thus determine electricity usage less than the predetermined amount for one minute of cooking. As another example, the smart device may be a cable box. The user may select a show to watch that is one hour long. Historically, when a user selects a show of one hour, the user may watch the entire show; however, on Fridays between 7 and 8 o'clock, the user may only watch a show for an average of 35 minutes. On Fridays, the prediction module 560 may predict that the user will watch for 35 minutes and thus determine electricity usage less than the predetermined amount for a one-hour show. In some embodiments, the processor may be configured to execute computer instructions that cause the smart device to perform the functions and operations described herein. The computer instructions may be loaded into the memory for execution by the processor and/or data generated, received, or operated on during performance of the functions and operations described herein may be at least temporarily stored in the memory. The smart device as discussed above may provide for various advantages. For instance, a manufacturer of the smart device may not need to disclose device operations to allow an outside device, such as an electricity monitoring system, to determine electricity usage for a selected operational profile because the smart device may determine and send its electricity usage and/or predicted electricity usage. Alternately or additionally, when the smart device is upgraded or the smart device is newly associated with a unit, an electricity management system associated with the unit does not need to be upgraded or changed to determine the electricity usage of the smart device because the smart device may report its electricity usage to the electricity management system.

Although the smart device illustrates various discrete components, such as the prediction module and the determination module, various components may be divided into additional components, combined into fewer components, or eliminated, depending on the desired implementation.

A robotic system is provided to dextrously transfer cooking items to/from the appliances. The hand can be mounted on a home robot or a conveyance system to pick up cooking ingredients and to move them to a cutting board and then to an oven if heat is needed. The robot includes a plurality of cameras, and images are processed by a vision system such as OpenCV to detect objects and the handle them. The robotic hand is attached to a wrist section which is movably connected to a forearm section. The robotic hand includes five moveable fingers that closely resemble the fingers on a human hand and are capable of moving in directions having a total of twelve degrees of freedom. Each of the two dexterous fingers and the thumb have three degrees of freedom (two pitch and one yaw); each of the two grasping fingers has one degree of freedom (pitch), and the palm member has one degree of freedom (pitch). The wrist section is capable of moving palm housing 16 in directions having two degrees of freedom (pitch and yaw) relative to the forearm section which houses the motors or actuators, and the circuitry and drive electronics. The robotic hand, wrist section 12, and forearm section 14 are individually discussed in further detail below, followed by a discussion of a drive train, a lead screw assembly, the palm, a grasping finger, a dexterous finger, and the thumb. More details on the robotic hand is shown in U.S. Pat. No. 6,244,644, the content of which is incorporated by reference.

In one simple example, a user is on the way home and the system or the user directly issues a command to prepare pizza for dinner. The hand can pick an microwaveable pizza from the refrigerator frozen section ahead of time to thaw the pizza, and then move the pizza to the microwave oven, with instructions to coordinate the completion by the time the owner gets home, after appropriately considering traffic delays. Meanwhile, the dexterous hand can make salad and sprinkle a few freshly cut olives on the pizza when it is cooked.

In one embodiment, a cook top is positioned above the oven and includes a number of gas burners. Each of the burners has a grate positioned above it, and the grates define a cooking surface. Each of the burners is configured to produce a controlled flame that generates a quantity of heat, which may be used to heat cooking utensils (i.e., pots and pans) placed on the grates. The burners and grates are arranged on the cook top such that a user can simultaneously heat pots, pans, skillets, and the like. The cooker has one or more cameras that monitor the cook top surface for over boiling events or signs that the meat is overcooked (turning black/smoke) and reduces or cuts off the flame automatically. In addition, sensors 90 are used to determine when food is ready. Sensor cooking monitors the temperature and amount of steam coming from the food to judge how much water remains and how long it should continue heating. In one embodiment, a process can estimate if the interior of the meat is done by monitoring temperature at the outside of the meat, the length of time in the oven, the color of the meat, the moisture in the oven, among others. In another embodiment, gas sensors can react to specific molecules. Multiple gas sensors can be used in an array, generally referenced as an "electronic nose", so that more unique patterns can be detected in sampling readings across the multiple sensors.

A process can run the electronic nose recognition with one or more classifiers to detect the effect of time and distance on the gas sensors' ability to react to the gas molecules released in an odor. In one embodiment, the system segments the time series data into five-second frames which are used to detect potency and diffusion changes in near real time, while avoiding the delayed feedback that would be caused by a larger window. Then, each sample is normalized. The system extracts a plurality of statistical features from each sensor' values collected from the gas sensors over each five-second frame. These features can include: min, max, mean, standard deviation, sum, variance, slope, and y-intercept.

The classifier and the gas sensors enable a fuller picture of what is happening in a kitchen. In addition to the suite of other sensor technologies (e.g., audio or video, temperature, moisture), gas sensors have the added benefit of being able to provide information previously invisible to many other kitchen tracking systems, providing the ability to not only classify the type of food, but also to help with nutritional tracking. An oven has a cooking chamber into which pans, sheets, or other cookware carrying food may be placed to be heated. The oven may also have a built in camera to monitor whether the turkey has turned to a predetermined color and alters the cooking temperature. Also, the camera in the chamber 40 monitors the food being cooked to a predetermined temperature and/or meat color as specified by a recipe. The cooking chamber 40 includes a number of racks located therein. A door assembly (not shown) is hinged to the front of the housing and permits access to the cooking chamber. A gas-fired bake burner 44 with its associated cover is located below the rack. The bake burner is configured to provide heat for baking or otherwise cooking food items in the cooking chamber. A user may control the operation of the oven using a control interface located on the upper panel. The burner control device includes an electronically controlled gas valve operable to control the supply of gas to the gas burner. While the cooker/oven has been described as gas oven, the same principle applies to electric cooker/oven. Similar principles apply to slow cookers and multi-cookers, toasters, countertop ovens, microwave ovens, waffle bakers, among others.

The blenders, stand mixers and food processors all have a processor and a wireless communication module and the above described sensors. In addition, they can have rheometer sensors. A rheometer is used to measure the way in which a liquid, suspension or slurry flows in response to applied forces. It is used for those fluids which cannot be defined by a single value of viscosity and therefore require more parameters to be set and measured than is the case for a viscometer. It measures the rheology of the fluid. Rheometers that control the applied shear stress or shear strain are called rotational or shear rheometers, whereas rheometers that apply extensional stress or extensional strain are extensional rheometers. With rheometers, the blenders and other mixers can mix with precision.

The coffee makers and tea makers can have the above sensors including temperature sensors. These appliances can be set to remotely turn on, applied one or more water temperature curves over a preset time period to make coffee or tea with perfection. In addition, they can be linked to the refrigerators to dispense milk or other suitable additions.

For example, the smart tea maker can follow the following recipe: the water should be below boiling. This is because the amino acids (which produce the tea's flavour) dissolve at lower temperatures than tannin. Tea made with water at 100° c. will be more astringent and less sweet. The process stops the kettle before it reaches the rolling boil—white and green teas are best at about 70° c., black and oolong teas use water around 85° c. For herbal infusions use 100° c. water, and 90° c. for Chamomile. The tea can be left in the hot water for a predetermined period and then it is ready for consumption.

Figure 13B:
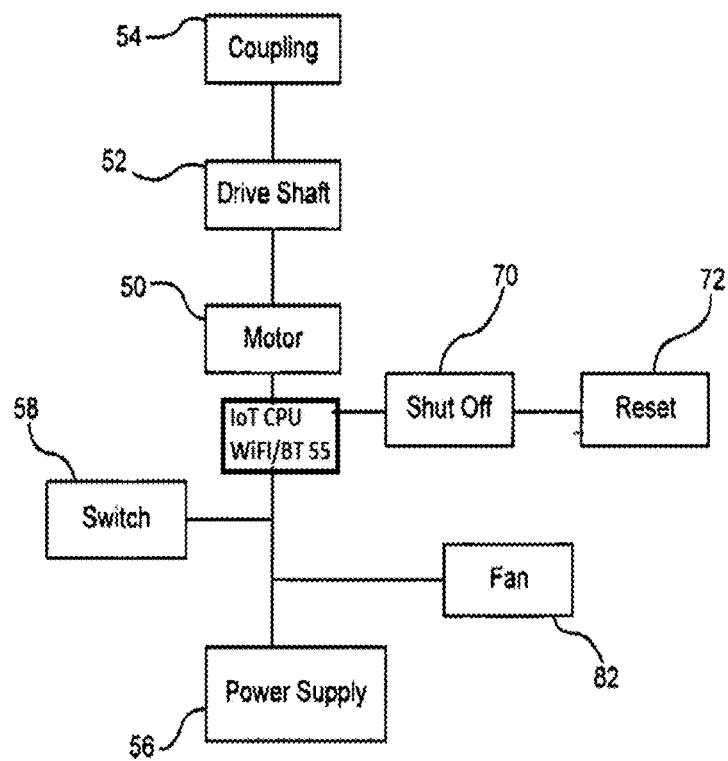

FIG. 13B shows one exemplary motorized appliance such as a blender that is IoT enabled with WiFi and/or Bluetooth. Appliance body houses a motor 50, a drive shaft 52, and a coupling 54, as depicted in FIG. 3B. While the embodiments shown include a motor of overly sufficient power (to quickly blend materials), it is contemplated that any motor can be utilized. Motor 50 is engaged with shaft 52 so that motor 50 causes rotation of shaft 52. Shaft 52 is connected with coupling 54, thus causing rotation of coupling 54. Motor 50 is controlled by an Internet-Of-Thing (IOT) microprocessor 55 using suitable pulse width modulation (PWM) as known in the art. The IoT processor 55 can be a TI CC3200 Wi-Fi wireless microcontroller (MCU) that is Wi-Fi CERTIFIED™ at the chip level by the Wi-Fi Alliance™ with USB interface to PC for CCS/IAR using FTDI USB drivers and flash update over the USB. A power supply 56 is also provided for powering motor 50. In certain embodiments, power supply 56 is a plug and cord for use with a standard wall socket. However, it is contemplated that motor 50 can be powered by several different types of power supplies. For example, power supply 56 can be a lithium or other rechargeable battery. Additionally, standard batteries such as AA or AAA batteries can be utilized. To reduce overheating from running the motors, the system provides fans and cooling structures aimed at preventing excess heat from building up and becoming a fire hazard, while still allowing for sufficient power blasting of the motor. The Appliance may include a switch 58 for selectively providing power to motor 50. The switch can located within threaded opening 20, and is actuated by forcing container 14 towards blender base. However, it is contemplated that other switches can be used, for example, standard on-off switch as are known to those of ordinary skill in the art.

Figure 13C:
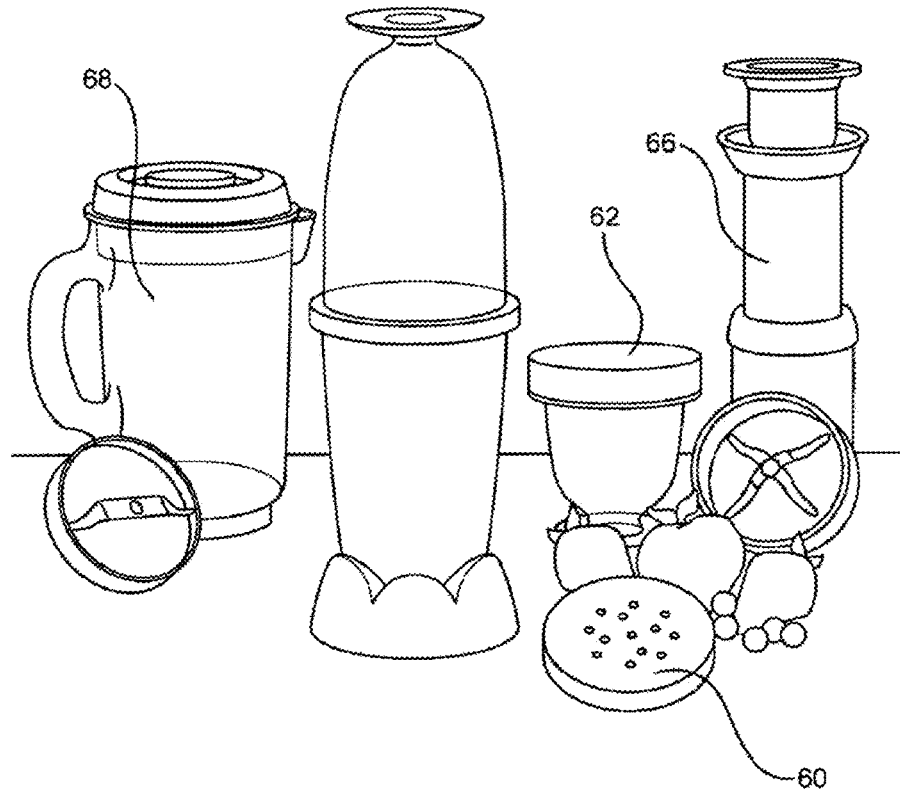

It is contemplated that a smart container can be used in conjunction with various caps/lids. For example, as shown in FIG. 13C, a shaker top 60, a storage lid 62, and a drinking rim 64 are provided. Shaker top 60 is a cap with a plurality of holes useful for dispelling grated cheese and the like from container. Storage lid 62 is a cap that substantially seals container 14 useful for storing used materials in a refrigerator. Both of these caps engage threaded opening 20 so as to remain fixed to container 14. Drinking rim 64 also engages threaded opening 20, so as to cover the threads. Drinking rim 64 is useful for drinking directly from container. It is also contemplated that blender base 12 can be used with other attachments than the standard containers. For example, as is also shown in FIG. 3B, it is contemplated to use blender base with a juicer attachment 66 or a standard blender pitcher 68. However, there exist other possibilities of attachments. The blender of FIGS. 3A-3B may or may not have a graphical display. In one embodiment, the blender is remotely controlled using a smart phone or table or remote computer. In another embodiment, the blender is has a large display that can display recipes. A touch screen can be provided so that the user can interact over the Internet using the blender display, for example. Alternatively, the blender can interact with control app on a smart phone acting as a user interface.

A smart cap or a smart container can be provided using the system of FIG. 2A, for example. One embodiment embeds electronics providing intelligence directly in a smart container. Other embodiments convert conventional containers into smart devices using smart cap. While monitoring of the smart cap 100 is continuous, transmission of content information can be continuous, periodic or event-driven. The microcontroller 155 is programmed with the appropriate warning and usage levels, as well as internal damage diagnostics and self-recovery features. The content information can take any form, including a simple warning/emergency indication that the content quality or age is approaching or exceeding specifications, respectively. The sensor includes a camera and image processor to detect if unusual films are forming on the surface of the food. The sensor can include the electronic nose and/or the electronic tongue sensor detailed above to detect unusual odor or rotting condition. Other sensors include time-temperature sensors that track the history of the container, microbial growth sensors, leakage sensors, shock sensors, and pathogen/contaminant sensors. In one embodiment to detect pathogens, a sensor detects quality of food by adsorption of volatile biomarkers on selected materials coated on the sensor. When the volatile compounds interact with the coating materials, the change can be sensed by infrared light directed towards the sensor, and a refractive index change causes wavelength shift of the infrared light reflected by the sensor. The wavelength shift is used to extract information on the volatile compound and their concentrations inside the container or package. In another embodiment, biosensors can be used that include, enzyme, antibody or antigen based biosensors; gene based sensors and whole cell sensor. Enzyme-based biosensors are based on electrochemical transduction systems with glucose oxidase sensors for example. Conjugated polymer based biosensors can be used that rely on indirect detection of the target analyte, usually a fluorescently labelled compound for biomolecular macromolecules such as proteins. Fluorescent sensors using boronic acid as a ligand, in a non-enzymatic approach for the detection of saccharides have found applications in microbial detection, as polysaccharides are a component of the bacterial cell membrane.

Adsorption sensors can be used. Many substances can adsorb enzymes and other biological materials on their surfaces for example alumina, charcoal, clay, cellulose, kaolin, silica gel, glass, collagen, carbon pellets and advanced material such as carbon nanotubes (CNTs). A simple procedure is when microbial cells are immobilized by simple absorption by placing the cells on a porous cellulose membrane. Generating pastes such as when enzymes or tissue are mixed with graphite powder and liquid paraffin. Entrapment sensors provide physical enclosure of biomolecule in a small space. Inert membranes have been used to provide close contact between the biomaterial and transducer. Types of membranes used include cellulose acetate (dialysis membrane); polycarbonate (Nucleopore), synthetic non-permselective material; Collagen, a natural protein; PTFE: polytetrafluoroethylene (trade name Teflon) and is a synthetic polymer selectively permeable to gases. Nafion, (a Dupont material), which is biocompatible and shown to be stable in cell culture and the human body. Polymeric gels can be used and prepared in a solution containing the biomaterial. Chemical polymers such as calcium alginate, carrageenan, polyacrylamide, and sol-gel (Sol-gel, is a glassy silica produced by polymerization of silicate monomers). Bonding and cross linking: a number of bonding mechanisms have been used including covalent bonding. A covalent bond exists between two atoms if they share electrons between them. The Biotin-Avidin bond is one of the strongest known non-covalent bonds. Avidin is a terameric protein that forms a highly specific binding site for Biotin. Sulphur compounds are known for their reactivity to metals and this absorb readily to the noble metals. Thiolised DNA can be attached to gold via different methods. Transducing element: the transducing element must produce a measurable signal that is proportionate to the concentration of the analyte/bioreceptor. Transducers can be divided into optical, electrochemical and mass based.

Optical transducers can be subdivided into light absorption, fluorescence/phosphorescence, reflectance, refractive index, bio/chemiluminiscence. In reflectance three widely used methods are Surface Plasmon resonance (SPR), total internal reflection fluorescence (TIFR) and attenuated total reflectance (ATR). Fiber optic biosensors can be used in food matrixes to detect pathogens. Electrochemical transduction methods can be subdivided based on the measured parameter: amperometric (current), potentiometric (potential), impedimetric (impedance) and conductometric. Mass sensitive biosensors are suitable for very sensitive detection, in which the transduction is based on detecting a small changes in mass. The two main types of mass based sensors are (1) bulk wave (BW) or quartz crystal microbalance (QCM) and (2) surface acoustic wave (SAW). The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

Food quality and other information from the microcontroller 155 are preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart cap/container themselves. In each smart container/smart cap, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks: 1. Neighbor discovery: in this task each smart container or cap sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart container (node) so that minimum energy is consumed. 4. Data transmission: the microcontroller processes the collected color data and based on the adopted data dissemination approach, the smart cap will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

One embodiment of a smart container includes sensors and wireless communication. Upon receiving a query over a wireless network, the container can transmit the remaining volume, the expiration date, and origin of the content. The expiration date and origin of the content can be set at the factory, and the travel history of the container can be added by the warehouse and the retailer. The bottles can have a level sensor and a quality sensor to provide remaining volume and quality. Upon a radio frequency (RF) query by a processor, each container would respond with identifying information, along with remaining amount and a quality rating, among others.

In a smart liquid container embodiment, a level sensor and a content quality sensor can be embedded therein. For example, the level sensor can determine remaining milk or juice in the container and respond to a query. A MEMS based resistivity sensor can be placed in the container to detect if, for example, milk has gone sour. Alternatively, an electronic nose can be used to determine if the content is bad. In another variation, the lid of the container can include a camera to look for mildew, among others. For moveable containers, In one embodiment, a container for storing vegetable includes a camera with image processing software to detect if mildew is present and if so an alert is generated. For leafy vegetables, the camera can detect if the leaves are wilting and also generate an alert. If frost is captured by the camera, the container can send a request to reduce the vegetable bin temperature.

FIG. 14A shows an exemplary smart refrigerator 200 that stores the smart containers therein. In one embodiment, the refrigerator includes a real window or a virtual window view of the interior of the refrigerator. The virtual view is done with a camera that shows the content inside the refrigerator on a display 202 that is on a refrigerator exterior. This allows users to inspect the content of the refrigerator without opening the refrigerator.

In a smart refrigerator embodiment, the smart containers can self identify upon query, so a user can ask containers with a particular expiration date range to blink an LED associated with the smart container. One embodiment uses a natural language interface coupled with speech recognition. Various implementations can be used with Apple Siri, Android Voice, or Amazon Echo. For example, Amazon Echo is a hands-free speaker controlled by voice. Echo connects to the Alexa Voice Service to play music, provide information, news, sports scores, weather, among others. Echo has seven microphones and beam forming technology so it can hear voice commands from across the room—even while music is playing. When a user wishes to use voice command, the user can say the wake word such as "Refrigerator", "Oven" or "Alexa" (for Amazon Echo) and then a command. The appliance would provide context to improve understanding of the command. For example, a speech enabled refrigerator can parse the verbal command "Refrigerator, identify expiring items" and issue a command to all containers inside the refrigerator that meet the expiration limit. The refrigerator can display the result on a display outside the refrigerator. The refrigerator can also display an interior cam view of the frig, annotated with the location of matching items responsive to a verbal query. The refrigerator can also identify low inventory and suggests or adds to a shopping list.

One embodiment provides automatic inventory refill requests to a supermarket, Walmart, or Costco. In this embodiment, the refrigerator broadcasts a self-identification request to all containers inside the refrigerator. The containers reply with the ID and remaining quantity. Based on historical usage and user input on desired food, the refrigerator generates a refill order to a remote computer such as cloud based inventory monitoring application 222.

FIG. 14B shows an exemplary process for on-line refrigerator inventory replenishment. The process is as follows:

Refrigerators in a local area provide real-time demand estimate (240)

Farmers predict cycle's harvest (242)

Refrigerator generates forecast of weekly demands (244)

System matches harvest cycle to each refrigerator requirement (246)

System automatically emails orders to the farmers and producers, who harvest or prepare accordingly (248).

Goods are delivered from farmers or vendors to a local staging area or warehouse and then packaged for delivery (250)

Owners either pickup from the local staging area or a ride-sharing service can pick up and deliver in the same day (252)

Refrigerator inventory is updated (254)

In one embodiment, local suppliers such as farmers input predictions for that cycle's harvest and the inventory is updated constantly during each order cycle to account for changes in the field. The refrigerators automatically log on choose pickup locations, and shop from traditional grocery categories. Periodically, the system automatically emails orders to the farmers and producers, who harvest or prepare according. Independently contracted drivers deliver the goods from vendors to the local warehouse. Foods are wrapped in compostable protective materials, and refrigerated items are insulated in inflated cool sleeves with biodegradable ice packs. Everything is placed in insulated containers for easier stacking, and each step is tracked for accountability.

Referring to FIG. 14C, a smart washer embodiment is shown with a cabinet 412 with a front portion 415 and a rear portion 417. The front portion 145 has an opening 430 closeable by a door 416. The clothes washer described herein shares many features of a well-known clothes washer, and will not be described in detail except as necessary for a complete understanding of the invention. The cabinet 412 encloses a perforate rotatable basket 418 within a stationary imperforate tub 420. Clothing can be thrown into the washer through the door 416. The cabinet 412 also mounts a control panel 414 having control elements, such as switches, dials, buttons, and the like, operably coupled with a solid-state microprocessor-based controller 422 with an accelerometer and a camera for controlling the operation of the clothes washer. The controller 422 also interacts with a display panel 456 to provide additional user interface with the user. The controller 422 can also communicate with a smart phone to receive instructions from the user, or can interact with the internet through a WiFi or Zigbee connection, among others. The camera captures images of the clothing being washed and the processor/controller performs imaging functions that identify color, size of load, evenness of the load, and washing instructions imprinted on the clothing.

In one embodiment, prior to washing, a camera robot arm 438 snakes around the clothing items and performs text recognition of the washing instructions imprinted on washing labels. One embodiment of the robotic snake arm is a flexible robotic limb which can function as a robotic snake, here called a robo-snake. These improvements are particularly pertinent to miniaturization applications such as catheters or positioners for microsurgery, micro-assembly, micro-manipulation, or micro-exploration. This invention features improvements in a prior-art flexible robotic arm of Rennex, U.S. Pat. No. 5,386,741, the content of which is incorporated by reference. The flexible arm has a series of expansible base units which were interconnected by six independently controlled length actuators. This interconnection was accomplished with universal joints. This structure was very versatile is terms of its motion. Each stage could extend, tilt, twist, and expand or contract radially. The combination of stages could position its working end along a tortuous path, and it could self-propel itself along a grid, a tunnel, or a blood vessel. It could also grip objects or position tools or imaging devices. Other features included optimal simplicity of control, ease of construction, lightness, and stiffness. The camera or an ultrasonic cleaner such as an ultrasonic toothbrush can be mounted at one end of the robotic snake.

With the camera, the robot arm 438 also identifies color, and classifies the item such as shirt, pant, blanket, among others. The processor 422 then segregates the items using the robot arm if possible, and otherwise warns the user to manually separate the items to optimize the washing operation.

IN one embodiment, the camera efficiently, reliably and accurately senses load size, the existence and magnitude of any imbalance condition, and sense other obstructions that may adversely affect washing performance and provides such information to the processor 422 to actuate the motors to avoid imbalance conditions. The processor 422 determines the mass of the vibrating system, including the basket 18, the tub 20, the axle 50, and the like, are readily determined. The mass of the total clothes load can be determined in a well-known manner, such as by evaluating the motor speed, current, or watts draw during motor start up at a preselected time during the operation of the clothes washer. Some methods require that the basket angular velocity pass through the critical speed. Using the well-known relationship between centrifugal force caused by imbalance $$F = mR\omega^2$$

where

F=centrifugal force caused by imbalance;

m=mass of imbalance;

R=radial location of the imbalance to rotating axis; and

ω=angular velocity.

The moment M acting on the forward bearing can be calculated as

M=Fd, where d=longitudinal distance between imbalance load and forward bearing, and M=moment acting on forward bearing.

The X-directional acceleration is directly proportional to the moment, M. When using an accelerometer according to the disclosed embodiment, the magnitude of the voltage signal from the accelerometer is proportional to the moment. The processor 422 can adjust the motor power using fuzzy logic to prevent the imbalance condition.

At times, the clothes washer may be supported upon a soft floor. At 140 RPM a soft floor will cause increased vibration and potentially unacceptable vibration and cabinet hits at higher speeds. The accelerometer-based system can detect these increased vibrations and adjust the spin cycle accordingly. Similarly, improper installation of the clothes washer may result in the clothes washer being supported on only three legs. This can also lead to increased vibration and cabinet hits, which the accelerometer can detect at the 140 RPM speed, and the spin cycle can be adjusted accordingly.

The accelerometer-based system can also accommodate a load consisting of a single bath towel or similar small, but readily imbalanced, load. Furthermore, in response to a load imbalance detected at a particular speed, prior art technologies reduce the spin speed to the prior stage spin speed, which may be a 200 RPM decrease. With the accelerometer-based system described herein, the spin speed is reduced 50 RPM, thereby providing more effective extraction of liquid notwithstanding the imbalance of the load.

One embodiment detects severe stains on the clothing, and performs spot cleaning prior to general washing by stretching the fabrics (in some cases over a hard surface) to increase their ability to attract cavitation bubble implosions and applying an ultrasonic applicator such as an ultrasonic toothbrush to the stain areas. In the case of stretching the fabric over a hard surface, the surface would actually act as the "receiver" of ultrasonic cavitation bubble implosions. The fabric is in the intense cavitation zone adjacent to the hard surface.

The user can interact with the washer using the mobile phone. For example, the user can accept the system's segregation recommendation or override the recommendation. The user can remotely guide the washing machine to operate immediately or run overnight to save electricity costs for regions with time-based differential electricity pricing. Substantially the same structure exists in a dryer embodiment, but with a heater to dry the clothing rather than a water pump. In the dryer embodiment, the processor can cause the snaking robot to read drying instruction label text or icons.

Figure 14D:
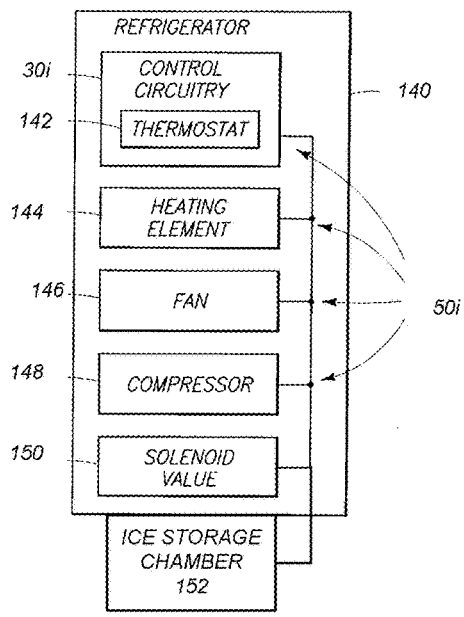

FIGS. 14D-G show exemplary embodiments of refrigerator, water heater, clothes washer, and dish washer. FIG. 14D shows an exemplary refrigerator. The illustrated refrigerator 140 includes control circuitry 30 *i* (embodying a thermostat 142), a heating element 144, a fan 146, a compressor 148, and a solenoid valve 150 in the depicted embodiment. Control circuitry 30 *i*, heater 144, fan 146, and compressor 148 comprise exemplary loads 50 *i* in the depicted example. The refrigerator 140 also include an ice energy storage chamber 152. The embodiment uses ice storage to store coolth and used when the DR period is active. First exemplary power management operations of control circuitry 30 *i* include adjustment of a temperature set point of thermostat 142. It may be desired in at least one embodiment to set a relatively short duration of any temperature adjustment during power arrangement operations. Another possible power management operation provides temporary disablement of defrost operations of heating element 144 (e.g., coupled with unillustrated coils of refrigerator 140), or adjusting a time of the defrost operations controlled by control circuitry 30 *i*. In another arrangement, heating element 144 may be used to provide anti-sweat operations (e.g., appropriately positioned adjacent an exterior portion of an unillustrated cabinet of refrigerator 140—for example adjacent to a door) and power management operations may include temporary disablement of the anti-sweat operations or otherwise adjusting such operations to occur at another moment in time wherein power management operations are not being implemented. Additional exemplary power management operations include disablement of interior air circulation operations implemented by fan 146 and/or controlling operations of compressor 148 (e.g., including temporarily disabling or reducing the speed of compressor 148). Additional aspects include implementing a hot gas bypass operation of compressor 148 using solenoid valve 150 and as described in further detail above in one example. One other embodiment provides a multi-stage refrigerator 140 having a plurality of cooling stages and a power management operation includes controlling the refrigerator 140 to operate at less than the available number of cooling stages thereby reducing the amount of energy consumed by the appliance.

In one implementation, the refrigerator ice energy storage chamber provides a predetermined cold energy for a refrigerated volume for the predicted DR period; and a fan to circulate cold air from the ice energy storage chamber inside the refrigerated volume during the predicted DR period. The refrigerator can include a phase change material (such as water, salted water, parafin, among others) coupled to the refrigerated volume to maintain the refrigerated volume at a predetermined temperature during the predicted DR period. The controller modulates compressor operation to reduce power consumption during the predicted DR period. The controller precharges the refrigerator prior to the predicted DR period. The controller precharges the refrigerator based on weather or warning from an authority. The refrigerator can include ice storage to store coolth when power is available and used during the DR period. The fact that water is a pure substance and that making ice does not involve a chemical reaction is one reason that ice storage is a relatively trouble free system.

The phase change materials include alkanes, paraffin waxes and salt hydrates. These materials undergo a reversible solid to liquid phase change at various transition temperatures. 'Solid-state' phase change materials are those that change from amorphous to crystalline phases while remaining 'solid.' Both paraffin wax and salt hydrates typically require encapsulation to contain the liquid phase, which adds to final cost of this PCM. Salt hydrates are inorganic materials. Inorganic compounds have twice the volumetric latent energy storage compared to organic compounds. The organic compounds however, have the advantages of melting congruently and are non-corrosive. Salt hydrates will melt incongruently causing phase separation. There are two categories of solid-state phase change materials: layered perovskites and plastic crystals. The transition temperature of solid-state phase change materials in a pure form runs on the higher side for use in passive applications. By mixing these compounds in various ratios, the transition temperature can be lowered.

PCM can use paraffin waxes which are part of a family of saturated hydrocarbons. The structure is the type C n H 2n+2. Those with carbon atoms between five and fifteen are liquids at room temperatures and are not considered. Normal or straight chain and symmetrically branched chain paraffin waxes are the most stable. Typically, paraffin waxes with odd numbers of carbon atoms are more widely used because they are more available, more economical and have higher heats of fusion. Paraffin waxes are composed mainly of alkanes, approximately 75%. Alkanes and paraffin waxes are both organic compounds. Paraffin can contain several alkanes resulting in a melting range rather than a melting point. As the molecular weight increases, the melting point tends to increase as well. Using different mixtures of alkanes, specific transition temperatures for paraffin waxes can be attained. Paraffin waxes and alkanes at the transition temperature melt to a liquid and solidify upon cooling. They do not have the containment problems of salt hydrates. The properties of normal paraffin wax are very suitable for latent heat storage. They have a large heat of fusion per unit weight, they are non-corrosive, nontoxic, chemically inert and stable below 500° C. (932° F.). On melting, they have a low volume change and a low vapor pressure. Mixing different molecular weight paraffin waxes together can easily vary melting temperature. Since they are commercially available, the cost is reasonable. Prime candidates for passive applications are tetradecane, hexadecane, octadecane and eicosane. Paraffin wax has a low thermal conductivity. However, the addition of additives such as graphite could increase the thermal conductivity. A Boulder, Colo. company, Outlast Technology, distributes outerwear made of fabrics that incorporate encapsulated paraffin wax. The Outlast Technology fabric involves the microencapsulation of microscopic size droplets of paraffin wax. These encapsulated particles of wax are then incorporated into fabrics and foams that are used for lining materials.

Octadecane in its pure form has a relatively high heat of fusion with a transition temperature close to an ideal passive temperature. Its latent heat storage is more than three times greater than the NPG/PG mixture. Based on thermal storage capabilities, octadecane is the superior material, followed by the Kenwax 18.

Paraffin wax and solid-state phase change materials show the behavior of under or super cooling. This behavior occurs when the material does not solidify at the same temperature at which it melted. Solid-state phase change materials have shown more than a twenty-degree difference. The difference is not as noticeable in paraffin waxes. Other phase change materials can be used.

Figure 14E:
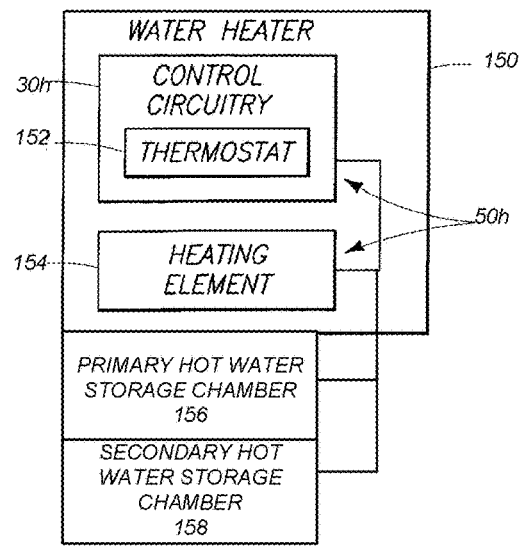

FIG. 14E shows an exemplary water heater. Water heater 150 includes control circuitry 30 h (embodying a thermostat 152 in the illustrated configuration) and a heating element 154. Heating element 154 is configured to heat water in a main reservoir 156 and an associated reservoir 158 to a desired temperature in the depicted configuration. Control circuitry 30 h and heating element 154 comprise loads 50 h of water heater 150 in one embodiment.

According to an illustrative embodiment, power management operations of system 150 and implemented by control circuitry 30 h include adjusting a set point of thermostat 152. For example, the thermostat set point may be temporarily lowered (e.g., for a period of tens of seconds, or a few minutes in some examples). In other exemplary power management operations, control circuitry 30 h may directly disable or provide other control of heating element 154 and gate pre-heated water from the back up reservoir 158 during the DR period.

According to additional exemplary aspects, a set point of any of the thermostats disclosed herein of the various appliances may be assigned to one of a plurality of possible power management set points according to a monitored condition of electrical energy of system 101. For example, a scale of set points may be used according to the condition of the electrical energy (e.g., the temperature set point may be decreased at predefined decrements (1-10 degrees for example) corresponding to the system frequency of the electrical energy deviating respective predetermined amounts (e.g., 10 mHz) from the nominal frequency. In accordance with the described example, the magnitude of adjustment of the thermostat set point increases as the deviation of the system frequency from the nominal frequency increases.

In one implementation, the water heater 150 uses the back-up heated energy storage chamber 158 to store a reserve heated water to maintained a predetermined temperature output for the water heater during the predicted DR period; and a valve to mix the reserve heated water with the water in the main water heater tank during the predicted DR period. The water heater can include a phase change material coupled to the water volume to maintain the water at a predetermined temperature during the predicted DR period. The water heater controller modulates heater operation to reduce power consumption during the predicted DR period. The controller can precharge the water heater prior to the predicted DR period or based on weather or warning from an authority.

Figure 14F:
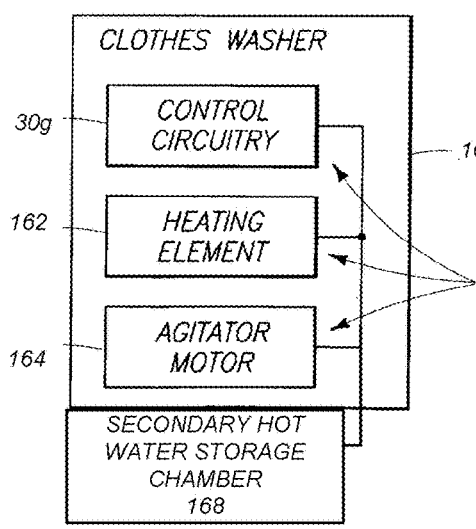

FIG. 14F shows an exemplary clothes washer. In one implementation, the washer has a digitally actuated latch to secure a washer door during the predicted DR period. If the washer is in an uninterruptible cleaning operation during the predicted DR period, the controller reduces power consumption during the predicted DR period and subsequently repeats the uninterruptible operation after the predicted DR period. Further, if the washer is in an extendible cleaning operation during the predicted DR period, the controller reduces power consumption during the predicted DR period and subsequently completes the extendible operation after the predicted DR period. The washer appliance can include a back-up heated energy storage chamber to store a reserve heated water to maintained a predetermined temperature output for the heater during the predicted DR period; and a mixer to mix the reserve heated water with cold water to maintain a predetermined washing temperature during the predicted DR period. A data input device can indicate the use of detergent additive or bleach usage, wherein the processor ignores the predicted DR period to avoid damage to items in the washer. The exemplary clothes washer 160 may include control circuitry 30 d, a heating element 162, and an agitator motor 164. Heating element 162 is configured to heat water used in an associated compartment (not shown) of clothes washer 160 configured to receive and wash clothes. Heating element 162 is also used to heat a water reservoir 168 for use during the temporary DR period so that washing operations can continue. Agitator motor 164 is configured to oscillate between different rotational directions or otherwise agitate clothes within the associated compartment during wash and/or rinse operations. Control circuitry 30 g, heating element 162 and agitator motor 164 comprise associated loads 50 g of clothes washer 160 in the depicted embodiment. In one configuration, power management operations of clothes washer 160 include reducing or ceasing the supply of electrical energy to heating element 162 to reduce internal temperatures of water in the associated compartment and/or agitator motor 164 to reduce motion of the motor 164. The reduction in power by controlling heating element 162 may be linear and accordingly the benefits may be directly proportional to the reduction in the water temperature. The reduction in power to agitator motor 164 may be proportional to a product of angular acceleration, mass and angular velocity. A slowing down of agitator motion of motor 164 could affect both a reduction in acceleration as the motor reverses its motion as well as angular velocity. In other embodiments, it may be desired to maintain agitator motor 164 in an operative mode during an implementation of power management operations with respect to heating element 162.

An exemplary clothes dryer may similarly include control circuitry, a heating element, and a tumbler motor. Heating element is configured in one embodiment to heat an associated compartment (not shown) of clothes dryer configured to receive and dry clothes. Tumbler motor is configured to spin clothes within the associated compartment during drying operations. In one configuration, power management operations of clothes dryer include reducing or ceasing the supply of electrical energy to heating element (e.g., reducing an amount of current supplied to heating element) and/or tumbler motor. It may be desired to maintain tumbler motor in an operative mode during an implementation of power management operations with respect to heating element.

Figure 14G:
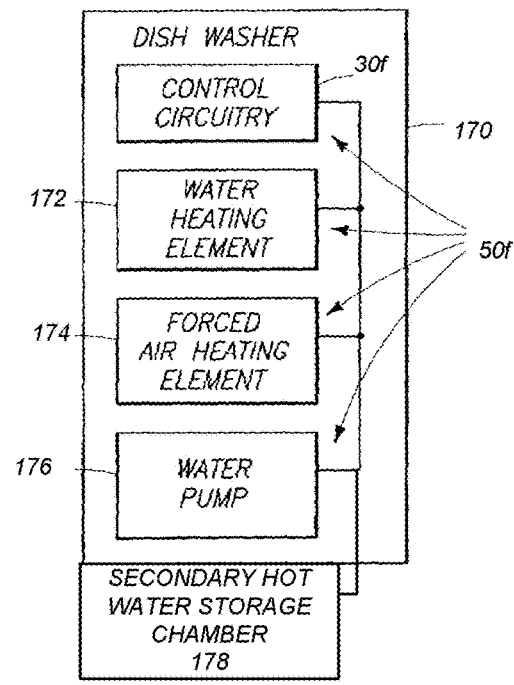

FIG. 14G shows an exemplary dish washer. Dish washer 170 includes control circuitry 30 $f$, a water heating element 172, a forced air heating element 174, and a water pump 176 in but one embodiment. Dish washer 170 may additionally include a compartment (not shown) configured to receive dishes. Water heating element 172 may adjust a temperature of water used to wash dishes using dish washer 170 in one embodiment. Heating element 172 is also used to heat a reservoir 178 to provide hot washing water during a DR period. Forced air heating element 174 adjusts a temperature of air used to dry the dishes in one implementation. Water pump 176 may spray water on the dishes during a cleaning and/or rinsing cycle to provide a dish cleaning action and/or rinsing action. Control circuitry 30 $f$, heating elements 172, 174, and water pump 176 may comprise associated loads 50 $f$ of dish washer 170.

Exemplary power management operations of dish washer 170 implemented by control circuitry 30 $f$ in one embodiment include controlling the water heater 172 to reduce a water temperature boost cycle during wash operations and/or reduce air temperature by forced air heater 174 during rinsing/drying operations. Reduction of water temperature provides corresponding linear reductions in electrical power consumption. Control circuitry 30 $f$ may also control operations of water pump 176 (e.g., reduce the operational speed of pump 176) during modes of reduced power consumption.

The IOT appliances include one or more of the following aspects:

1. A kitchen system, comprising:
   a body; a processor in the body and coupled to a wireless transceiver; a camera coupled to the body; and an accelerometer to detect acceleration;
   an oven appliance or a cooker appliance coupled to a network;
   a refrigerator appliance coupled to the network;
   a robotic arm to move one or more containers between appliances for food cooking or drink mixing; and
   a smart phone, watch, tablet, or mobile computer wirelessly coupled to one or more of the appliances to control settings on the appliance.
2. The kitchen system of claim 1, wherein the appliance comprises:
   a processor;
   one or more sensors coupled to the processor; and
   code to receive a remote control from the smart phone, watch, tablet, or mobile computer and to actuate a valve, motor, sensor, or actuator in response to the remote control.
3. The kitchen system of claim 1, wherein at least one appliance comprises a camera.
4. The kitchen system of claim 1, wherein the appliance monitors inventory and communicates a reorder request to a remote computer.
5. The kitchen system of claim 1, wherein the appliance communicates usage, fan comments, or cooking information from a brand to a user.
6. The kitchen system of claim 1, wherein the appliance complies with a request or demand from a utility to reduce power consumption for a period.
7. The kitchen system of claim 1, wherein the appliance comprises one or more sensors to sense progress of food cooking or drink mixing.
8. The kitchen system of claim 1, wherein the appliance detects a potential component failure and requests service prior to a component failure.
9. The kitchen system of claim 1, comprising a robot to move items between at least two appliances.
10. The kitchen system of claim 1, wherein each appliance comprises an Internet-of-Things (TOT) appliance.
11. The kitchen system of claim 1, comprising a 3D printer to form food into a predetermined 3D shape.
12. The kitchen system of claim 11, comprising a syringe moveable in 3D, the syringe receiving food particles and having a computer controlled plunger to dispense the food particles to form a 3D shape.
13. The kitchen system of claim 11, comprising a plurality of syringes each moveable in 3D, each syringe receiving food particles with a computer controlled plunger to dispense the food particles to form a 3D shape.
14. The kitchen system of claim 13, wherein the food particles from each syringe are mixed together.

Smart Refrigerator

1. A refrigerator, comprising:
   a body; a processor in the body and coupled to a wireless transceiver; a camera coupled to the body; and an accelerometer to detect acceleration;
   a plurality of shelves or bins that receive digitally responsive containers requiring refrigeration;
   one or more wireless charging pads or layers each positioned on a shelf to power the digitally responsive containers;
   a transceiver coupled to a network to access the Internet and to communicate with one or more appliances coupled to the network; and
   a smart phone, watch, tablet, or mobile computer wirelessly coupled to the refrigerator to control refrigerator settings or receive status of the digitally responsive containers.
2. The refrigerator of claim 1, comprising a camera to detect spoilage or position of a container.
3. The refrigerator of claim 1, wherein the container responds to a query including remaining amount and freshness.
4. The refrigerator of claim 1, comprising a camera coupled to the processor and one or more volume indicia on the container to indicate remaining content.
5. The refrigerator of claim 2, comprising mildew detection code to determine the presence of mildew in a container.

6. The refrigerator of claim 1, comprising a wireless power transmitter coupled to a container to transfer power from a layer or sheet of wireless power transmitters and wherein the layer or sheet of wireless power transmitters receive container status data.

7. The refrigerator of claim 1, comprising code to report content status, age, quality, or how to enjoy the content.

8. The refrigerator of claim 1, comprising code to contact a consumer, distributor, retailer, or manufacturer with content status.

9. The refrigerator of claim 1, comprising an electronic nose to detect an odor indicating content quality.

10. The refrigerator of claim 1, comprising code to sequence usage of the container in a first-in-first-out (FIFO) order to reduce spoilage.

11. The refrigerator of claim 1, comprising code to determine if the content is below a predetermined threshold and if so order additional supply.

12. The refrigerator of claim 1, comprising a 3D ice printer to form a predetermined 3D ice shape.

13. The refrigerator of claim 12, comprising a syringe moveable in 3D, the syringe receiving liquid and having a computer controlled plunger to sequentially dispense the liquid in a layer and to freeze the layer to form a 3D shape.

14. The refrigerator of claim 12, comprising a plurality of syringes each moveable in 3D, each syringe receiving liquid with a computer controlled plunger to dispense the liquid layer.

15. The oven of claim 14, wherein the liquid particles from each syringe are mixed together.

16. The refrigerator of claim 1, comprising code to communicate usage, fan comments, or cooking information from a brand to a user.

17. The refrigerator of claim 1, comprising code to comply with a request or demand from a utility to reduce power consumption for a period.

18. The kitchen system of claim 1, comprising a robotic arm to move the container to an appliance for food cooking or drink mixing.

19. The refrigerator of claim 1, comprising code to detect a potential component failure and requests service prior to a component failure.

20. A system, comprising:
a body; a processor in the body and coupled to a wireless transceiver; a camera coupled to the body; and an accelerometer to detect acceleration;
an oven or a cooker coupled to a network;
a refrigerator coupled to the oven or cooker appliance, comprising:
  a plurality of shelves or bins that receive digitally responsive containers requiring refrigeration;
  one or more wireless charging pads or layers each positioned on a shelf to power the digitally responsive containers;
  a transceiver coupled to a network to access the Internet and to communicate with one or more appliances coupled to the network;
a robotic arm or conveyor to move an item from the refrigerator to the oven or cooker; and
a smart phone, watch, tablet, or mobile computer wirelessly coupled to the refrigerator to control refrigerator settings or receive status of the digitally responsive containers.

Smart Container

1. A container to store content therein, comprising:
a body; a processor in the body and coupled to a wireless transceiver; a camera coupled to the body; and an accelerometer to detect acceleration;
a volume sensor for the content;
a wireless transceiver; and
a processor coupled to the wireless transceiver and the volume sensor, the processor responding to a query on remaining content and quality of the content.

2. The container of claim 1, comprising a camera coupled to the processor and one or more volume indicia on the container to indicate remaining content.

3. The container of claim 2, comprising mildew detection code to determine the presence of mildew in the container.

4. The container of claim 1, comprising rechargeable battery or super-capacitor coupled to a wireless power receiver in the container to receive power from a layer or sheet of wireless power transmitters.

5. The container of claim 4, wherein the wireless power receiver comprises an NFC receiver and wherein the layer or sheet of wireless power transmitters receive container status data.

6. The container of claim 1, comprising code to report status including content age or quality.

7. The container of claim 1, comprising code to suggest best ways to enjoy the content.

8. The container of claim 1, comprising an electronic nose to detect an odor indicating content quality.

9. The container of claim 1, comprising code to contact a consumer, distributor, retailer, or manufacturer with a status of the content.

10. The container of claim 9, comprising code to exchange information between the consumer and a distributor, retailer or manufacturer of the content.

11. The container of claim 1, comprising a sensor to detect container opening.

12. The container of claim 1, comprising an anti-fraud lid and registration code to detect product tampering or product fraud.

13. The container of claim 1, comprising a MEMS sensor to detect liquid quality, wherein the MEMS sensor detect liquid conductance or resistance and compares with a predetermined quality rating.

14. The container of claim 1, comprising code to sequence usage of the container in a first-in-first-out (FIFO) order to reduce spoilage.

15. The container of claim 1, comprising code to determine if the content is below a predetermined threshold and if so ordering additional supply.

16. The container of claim 15, comprising code to determine expiration date and signaling a user to use prior to the expiration date.

17. A system, comprising:
an appliance;
a digitally responsive container to store content therein, the container received by the appliance, the container, including:
  a volume sensor for the content;
  a wireless transceiver; and
  a processor coupled to the wireless transceiver and the volume sensor, the processor responding to a query on remaining content and quality of the content; and
a smart phone, watch, tablet, or mobile computer wirelessly coupled to one or more of the appliances to control settings on the appliance.

18. The system of claim 17, comprising a camera coupled to the processor and one or more volume indicia on the container to indicate remaining content.
19. The system of claim 17, wherein the container comprises mildew detection code to determine the presence of mildew in the container.
20. The system of claim 17, wherein the container comprises rechargeable battery or super-capacitor coupled to a wireless power receiver in the container to receive power from a layer or sheet of wireless power transmitters.

Oven/Cooker

1. An apparatus to cook food, comprising:
    a body; a processor in the body and coupled to a wireless transceiver; a camera coupled to the body; and an accelerometer to detect acceleration;
    a cooking area to receive food, the area heated by a heater;
    one or more sensors to detect food cooking parameters;
    a camera to detect food color change;
    a processor coupled to the camera and to the one or more sensors;
  a transceiver coupled to a network to access the Internet; and
    a smart phone, watch, tablet, or mobile computer to control settings or receive status of the apparatus.
2. The apparatus of claim 1, comprising a temperature sensor to sense food temperature.
3. The apparatus of claim 1, comprising a tag communicator in communication with a tag on the food to access food content or cooking instruction.
4. The apparatus of claim 1, comprising code for changing cooking modes for optimal cooking, wherein the cooking modes include temperature variations over a predetermined period.
5. The apparatus of claim 1, comprising a tag with cooking data on a package, wherein the tag configures settings based on the cooking data.
6. The apparatus of claim 5, wherein the tag comprises a bar code or an NFC code.
7. The apparatus of claim 1, wherein the camera transmits food images during cooking to a user.
8. The apparatus of claim 1, wherein the camera automatically identifies the food being cooked and switches heating settings.
9. The apparatus of claim 1, comprising a scale to measure weight, wherein the weight is used to adjust cooking.
10. The apparatus of claim 1, comprising a humidity sensor.
11. The apparatus of claim 1, comprising a microwave heat source to cook food.
12. The apparatus of claim 1, comprising a 3D printer to form food into a predetermined 3D shape.
13. The apparatus of claim 12, comprising a syringe moveable in 3D, the syringe receiving food particles and having a computer controlled plunger to dispense the food particles to form a 3D shape.
14. The apparatus of claim 12, comprising a plurality of syringes each moveable in 3D, each syringe receiving food particles with a computer controlled plunger to dispense the food particles to form a 3D shape.
15. The apparatus of claim 14, wherein the food particles from each syringe are mixed together.
16. The apparatus of claim 1, comprising a robotic assembly to move an item from a refrigerator into the cooking area.
17. The apparatus of claim 1, comprising code to detect usage and recommend heater replacement.
18. The apparatus of claim 1, wherein the cooking area comprises a microwave oven chamber, slow cooker pot, a coffee pot, a waffle baker, or a toaster chamber.
19. A system to cook food, comprising:
  a body; a processor in the body and coupled to a wireless transceiver; a camera coupled to the body; and an accelerometer to detect acceleration;
  a refrigerator;
  an cooking appliance, including:
  a cooking area to receive food;
    one or more sensors to detect food cooking parameters;
    a camera to detect food color change;
    a processor coupled to the camera and to the one or more sensors;
  a transceiver coupled to a network to access the Internet; and
  a robotic arm or conveyor to move an item from the refrigerator to the cooking appliance based on a command; and
  a smart phone, watch, tablet, or mobile computer wirelessly coupled to the refrigerator and the oven to move the item from the refrigerator to the oven and to control oven settings or receive status of the oven.
20. The system of claim 19, wherein the cooking area comprises an oven chamber, slow cooker pot, a toaster chamber, microwave chamber, slow cooker pot, coffee pot, waffle baker, or a grill surface.

Smart Clothing Washer

1. A washer, comprising
    a chamber or a body; a processor in the body and coupled to a wireless transceiver; a camera coupled to the body; and an accelerometer to detect acceleration;
    a motor coupled to the chamber to wash an item;
    a valve coupled to the chamber to control water flow into the chamber;
  a drain valve coupled to the chamber to remove water from the chamber;
    a camera to inspect items in the chamber; and
  a processor coupled to the camera, the processor miming image processing to identify a soiled region for additional cleaning.
2. The washer of claim 1, comprising code to detect stains on the item.
3. The washer of claim 1, wherein the washer comprises a clothing washer.
4. The washer of claim 1, comprising a snaking robot arm to inspect an individual item for stain or for washing instruction.
5. The washer of claim 4, comprising an ultrasonic cleaning head coupled to the snaking robot arm to preclean a soiled area.
6. The washer of claim 1, comprising code to change a washing program based on detected characteristics of a clothing item and a detergent.
7. The washer of claim 1, comprising an accelerometer to detect chamber movement and code to balance a chamber given a predetermined load during washing.
8. The washer of claim 1, comprising code to segregate clothing items according to color, size, or washing instruction.
9. The washer of claim 1, wherein the washer comprises a dishwasher.

10. The washer of claim 9, wherein the camera detects dirtiness and quantity of dishes and set the cleaning cycle therefrom.
10. The washer of claim 9, wherein the camera detects a washing load with a casserole dish or bread pan and directs additional water at the washing load.
11. The washer of claim 9, comprising a robotic arm to move items from the washer to another chamber.
12. The washer of claim 1, comprising RFID tag in each item to provide information about the item type and washing instruction.
13. The washer of claim 1, comprising code to perform diagnostics on the washer, change its status, upgrade firmware, and launch an app that communicates directly with a manufacturer's service center.
14. The washer of claim 1, comprising a voice recognizer to answer a question or to change washing parameters.
15. The washer of claim 1, comprising an actuator to transport clothing into a drying chamber.
16. The washer of claim 1, comprising an actuator to transport clothing into a dryer.
17. The washer of claim 1, wherein the dryer includes:
   a chamber;
   a motor coupled to the chamber;
   a heater to warm the chamber;
   a humidity sensor to sense humidity in the chamber; and
   a processor coupled to the humidity sensor to stop when a humidity in the chamber reaches a threshold.
18. The washer of claim 1, comprising an actuator to transport clothing into a drying chamber.
19. The washer of claim 1, comprising a plurality of detergent nozzles each having a valve and an actuator to transport clothing into a drying chamber.
20. The dryer of claim 1, comprising a smart phone, watch, tablet, or mobile computer wirelessly coupled to the dryer to control settings or receive status of items in the chamber.

Smart Clothing Dryer

1. A dryer, comprising
   a chamber or a body; a processor in the body and coupled to a wireless transceiver; a camera coupled to the body; and an accelerometer to detect acceleration;
   a motor coupled to the chamber;
   a heater to warm the chamber;
   a humidity sensor to sense humidity in the chamber; and
   a processor coupled to the humidity sensor to stop when a humidity in the chamber reaches a threshold.
2. The dryer of claim 1, comprising a camera and code to detect fabric type or image processing code to recognize drying instruction on an item.
3. The dryer of claim 1, comprising an RF unit to communicate with an RF tag on an item to access drying instruction on the item.
4. The dryer of claim 1, comprising a robotic arm to segregate items based on drying factors.
5. The dryer of claim 1, comprising a snaking robot arm to inspect an individual item for drying factors.
6. The dryer of claim 5, comprising an ultrasonic cleaning head coupled to the snaking robot arm to perform additional cleaning on a soiled area.
7. The dryer of claim 1, comprising an accelerometer to detect chamber movement and code to balance the chamber given a predetermined load during drying.
8. The dryer of claim 1, comprising code to segregate clothing items according to color, size, or drying instruction.
9. The dryer of claim 1, comprising code to change a drying program based on detected characteristics of a clothing item and a fabric softener.
10. The dryer of claim 1, comprising a sorter to separate clothing items into a predetermined drying period or temperature.
11. The dryer of claim 1, comprising a robotic arm to move items from the dryer to another chamber.
12. The dryer of claim 1, comprising RFID tag in each item to provide information about the item type and drying instruction.
13. The dryer of claim 1, comprising code to perform diagnostics on the dryer, change its status, upgrade firmware, and launch an app that communicates directly with a manufacturer's service center.
14. The dryer of claim 1, comprising a voice recognizer to answer a question or to change washing parameters.
15. The dryer of claim 1, comprising a smart phone, watch, tablet, or mobile computer wirelessly coupled to the dryer to control settings or receive status of items in the chamber.
16. The dryer of claim 1, comprising an actuator to transport clothing into a washing chamber.
17. The dryer of claim 1, comprising an actuator to transport clothing into a washer.
18. The dryer of claim 17, comprising:
   a motor coupled to the chamber to wash an item;
   a valve coupled to the chamber to control water flow into the chamber;
   a drain valve coupled to the chamber to remove water from the chamber;
   a camera to inspect items in the chamber; and
   a processor coupled to the camera, the processor running image processing to identify a soiled region for additional cleaning.

Motorized Cooking Appliance

1. An appliance, comprising:
   a body; a processor in the body and coupled to a wireless transceiver; a camera coupled to the body; and an accelerometer to detect acceleration;
   a surface with a sensor to sense characteristics of food or drink;
   a motor to mix the food or drink;
   a wireless transceiver connected to the Internet; and
   a processor coupled to the wireless transceiver and the sensor, the processor running the motor according to a suggestion on the Internet on preparing the food or drink.
2. The appliance of claim 1, comprising a camera coupled to the processor to detect condition of the food or drink.
3. A system, comprising:
   an appliance with a body; a processor in the body and coupled to a wireless transceiver; a camera coupled to the body; and an accelerometer to detect acceleration;
   a digitally responsive appliance to store content therein, the container received by the appliance, the container, including:
   a volume sensor for the content;
   a wireless transceiver; and
   a processor coupled to the wireless transceiver and the volume sensor, the processor responding to a query on remaining content and quality of the content; and
   a smart phone, watch, tablet, or mobile computer wirelessly coupled to one or more of the appliances to control settings on the appliance.

18. The system of claim 17, comprising a camera coupled to the processor and one or more volume indicia on the container to indicate remaining content.
19. The system of claim 17, wherein the container comprises mildew detection code to determine the presence of mildew in the container.
20. The system of claim 17, wherein the container comprises rechargeable battery or super-capacitor coupled to a wireless power receiver in the container to receive power from a layer or sheet of wireless power transmitters.

Voice Controlled Appliance

An IOT voice controlled assistant may be worn on the body (wearable) or may be positioned in a room (e.g., at home, work, store, etc.) to receive user input in the form of voice interactions, such as spoken requests or a conversational dialogue. Depending on the request, the voice controlled assistant may perform any number of actions. For instance, the assistant may play music or emit verbal answers to the user. The assistant may alternatively function as a communication device to facilitate network voice communications with a far end talker. As still another alternative, the user may ask a question or submit a search request to be performed by a remote cloud service. For instance, the user's voice input may be transmitted from the assistant over a network to the cloud service, where the voice input is interpreted and used to perform a function. In the event that the function creates a response, the cloud service transmits the response back over the network to the assistant, where it may be audibly emitted.

Figure 14H:
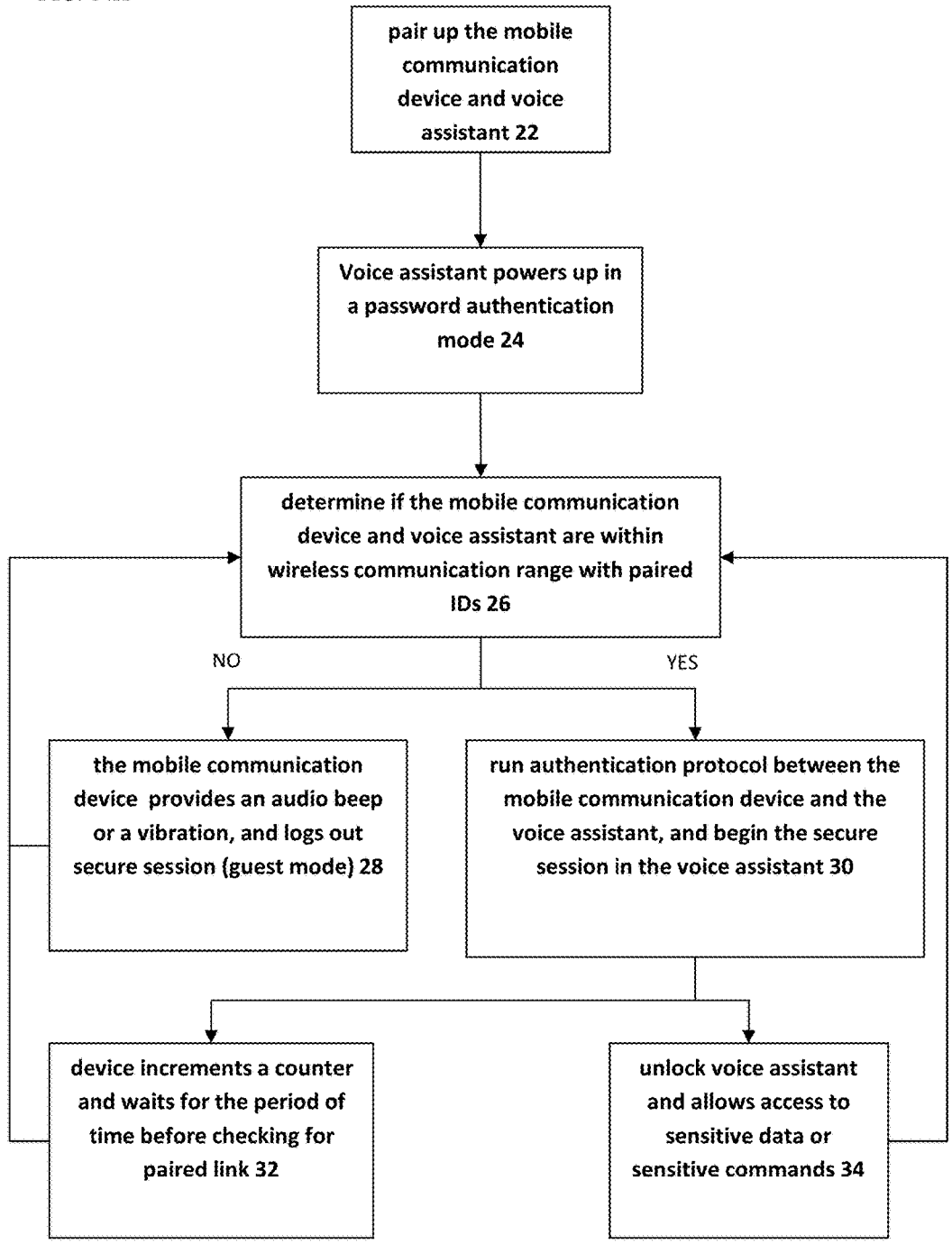

In one embodiment, the portable voice controlled assistant 104 includes a wireless transceiver such as WiFi and/or Bluetooth for sending and receiving authentication information to a computing device which can be local or cloud-based. In one embodiment, the authentication information is sent directly to the cloud and does not pass through the operating system of the local processor. Hence, the authentication process is independent of the operating system of the processor and any errors or security failures in the operating system do not affect the security of data storage device 10. In the embodiment of FIG. 14H, the system secures voice controlled assistant 104 with the use of a mobile phone as the wireless security key. The mobile phone uses a wireless transceiver such as WiFi and/or Bluetooth for sending and receiving authentication information to the voice controlled assistant. This communication is secured by encrypting the message using public key cryptography. The system has two software components: a component on the mobile phone and a component on the voice controlled assistant. The component on the voice controlled assistant is responsible for checking if a mobile phone with the wireless security key is nearby, sending challenge message to the mobile phone and receiving validation message from the mobile phone. If the wireless security key is not nearby, the software component will log out from Windows system. Otherwise, it will log in or keep the logging in state. The component on the mobile is responsible for security validation. In one implementation, the medium is Bluetooth. In the Bluetooth implementation, the typical range is about 10 m and the maximum range is about 100 m, and the system can simply default to a range of 10 m before an alarm is generated by detecting when the Bluetooth signal from the smart phone is lost. In another implementation, the wireless link is 802.11 (WiFi). In the WiFi embodiment, the distance can be much greater than 100 m, and the software can detect range by scaling the RSSI (received signal strength indicator) flag from the WiFi transceiver chip so that the RSSI value corresponds to the predetermined range. In yet a third implementation, the wireless link is a combination of 802.11 and Bluetooth. After a secure authorization has already been obtained, for instance, the process maintains a secure authorization between the mobile device and the voice controlled assistant. The process flow includes waiting until a predetermined period to elapse, reestablishing the secure channel between the wireless mobile device and the voice controlled assistant. The process determines if the authentication succeeds or fails, and denying access to the voice controlled assistant if the authentication fails.

Following the conclusion of the process flow of FIG. 14H, a secure authorization has been established between the voice controlled assistant 104 and a mobile communication device 10. This authorization must be periodically refreshed to ensure that the voice controlled assistant 104 is still within the immediate vicinity of the communication device 10. Thus, operations to the voice controlled assistant 104 are permitted until a predetermined time has elapsed. After interval, the voice controlled assistant 104 reestablishes the secure authenticated channel with the mobile device 10. If the authentication succeeds the device returns to the authenticated state and if not, the device goes to an unauthenticated state and will deny access to the voice controlled assistant 104.

Figure 14I:
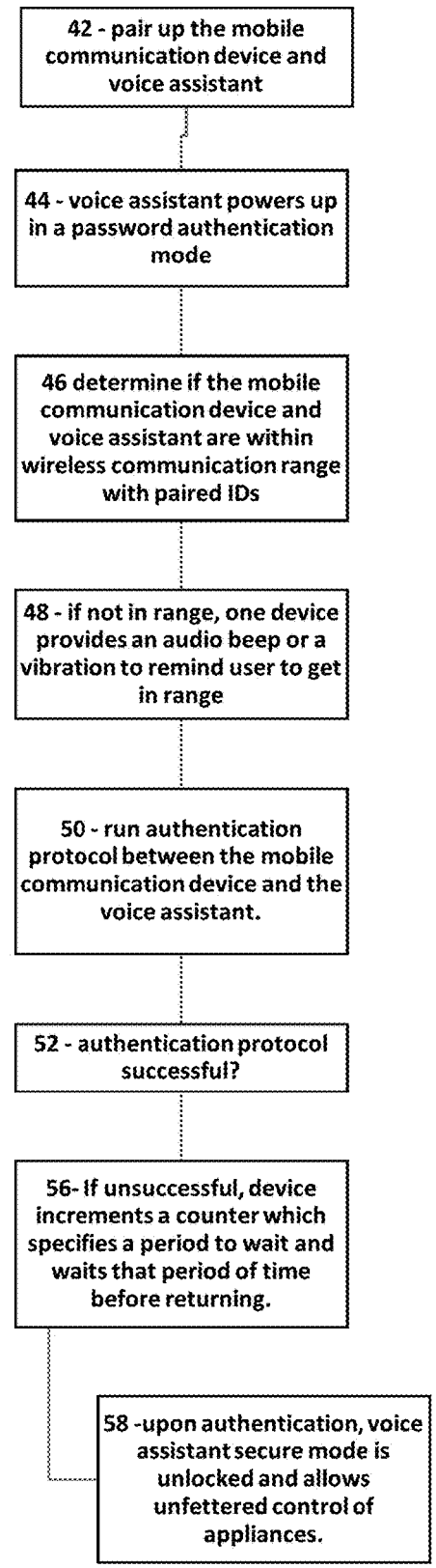

FIG. 14I is another exemplary diagram of a simplified process flow showing wireless communication between the mobile communication device 10 and a voice controlled assistant 104 to establish a secure authorization according to an embodiment of the present invention. The process flow includes step 42 to pair up the mobile communication device 10 and the voice controlled assistant 104. In the pairing operation, the process determines the unique ID (such as the processor ID of both devices 8 and 10). During operation, in step 44, the voice controlled assistant 104 powers up in a password authentication mode. In step 46, the process determines if the mobile communication device 10 and voice controlled assistant 104 are within wireless communication range and that the paired IDs match. In 48, if not in range, the mobile communication device 10 can provide an audio beep or a vibration to indicate that the user has separated from the voice controlled assistant. In step 50, the process executes an authentication protocol between the mobile communication device and the voice controlled assistant, and to begin the secure session in the voice controlled assistant. In step 52, the voice controlled assistant 104 determines if the authentication protocol has been successful, if it has the process continues to step 54 and if not it continues to step 56. In step 56, the device increments a counter which specifies a period to wait and waits that period of time before returning to step 46. Optionally, a key to decrypt data on the storage device is sent from the mobile communication device to the voice controlled assistant over the established authenticated communications channel. In step 54, the voice controlled assistant computer 8 is unlocked and allows operation of the computer. In another embodiment, the voice controlled assistant can use the key provided by the mobile device 10 to decrypt and encrypt data as required.

Figure 14J:
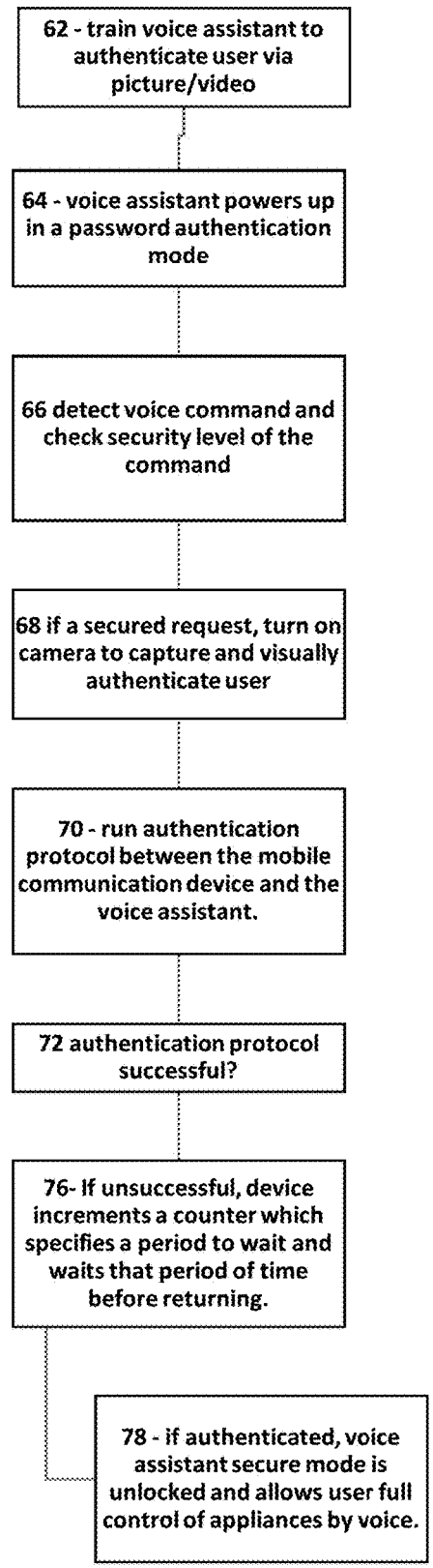

FIG. 14J shows an exemplary video based authentication. In 62, the system trains the voice assistant to authenticate user via picture/video. In 64, the voice assistant powers up in a password authentication mode and in 66 detects voice command and check security level of the command. In 68, if the system encounters a secured request (such as turn off alarm or unlock a door), the system goes into the next level of check by turning on a camera to capture and visually authenticate the user. In 70 the system runs an authentication protocol between the mobile communication device and the voice assistant. In 72 the system checks if the authentication protocol is successful. In 76, if unsuccessful, the device increments a counter which specifies a period to wait and waits that period of time before allowing another authentication. In 78, if authenticated, voice assistant secure mode is unlocked and allows user full control of appliances by voice.

In one embodiment, the communication between the mobile device 10 and the voice controlled assistant is secured. In addition to encrypting the message using public key cryptography, the message may be additionally protected by using a digital certificate. A certificate authority functions as a trusted party known to both the voice controlled assistant 104 and the cell phone 10. The certificate authority possesses both a public and private key, of which the private key is closely guarded. The public key of the mobile device 10 may be encrypted using the private key of the certificate authority. This constitutes a digital certificate that can be used to help authenticate different devices, in this case the mobile device 10 and the voice controlled assistant 104 to each other using the certificate authority. The certificate may be stored in a data storage device with the unique public and private keys of the voice controlled assistant.

In still another embodiment of the present invention, the electronics or motor within the voice controlled assistant 104 will not function without having established a secure authorization between the mobile communication device 10 and the voice controlled assistant 104. Power may be temporarily suspended to components within the voice controlled assistant, or the motor may be prevented from operating until a secure authorization was established.

In other embodiments, the system can use a wireless transmitter in the cell phone that communicates with a central processing unit (CPU) located within an electronic device, such as a computer or the voice controlled assistant itself. In this case the CPU of the voice controlled assistant controls encryption and decryption of the data on the hard disk drive. When the wearable transmitter in the cell phone is in range of the receiver in the CPU, the encrypted data is decrypted and stored unencrypted onto the hard disk drive. When the user and wearable transmitter leave the location, the CPU encrypts the unencrypted data and saves the encrypted file, and then deletes the unencrypted file.

In another embodiment, the system can restrict the voice controlled assistant power until a portable wireless transmitter is within range. By restricting power to the voice controlled assistant or components such as a disk drive, operation of the voice controlled assistant is disabled until the transmitter is in range of the device as the device is normally in a powered down state.

The user can be communicating with the remote entities via the voice controlled assistant. The assistant 104 outputs an audible questions, "What do you want to do?" This output may represent a question from a far end talker, or from a cloud service (e.g., an entertainment service). The user is shown replying to the question by stating, "Turn off all alarms and open all doors" Such command disables all security for the home and criminals can then freely take control of the home. The camera and speech system are then used to authenticate the user before disabling the security system, for example. The smart phone can be used as another authentication or confirmation before executing a supervisor level command to turn off security, for example.

Accordingly, the assistant may be implemented as an aesthetically appealing device with smooth and rounded surfaces, with some apertures for passage of sound waves, and merely having a power cord and optionally a wired interface (e.g., broadband, USB, etc.). In the illustrated implementation, the assistant 104 has a housing of an elongated cylindrical shape. Apertures or slots are formed in a base end to allow emission of sound waves. A more detailed discussion of one particular structure is provided below with reference to FIG. 3. Once plugged in, the device may automatically self-configure, or with slight aid of the user, and be ready to use. As a result, the assistant 104 may be generally produced at a low cost. In other implementations, other I/O components may be added to this basic model, such as specialty buttons, a keypad, display, and the like.

In one embodiment, the voice controlled assistant has a gateway onboard or alternatively as an add-on device coupled to the housing of the assistant. The gateway's functions are defined at the application layer. This gives the gateway greater responsibilities and capabilities than a router, which is simply concerned with addressing packets of data. The gateway can examine the contents of those data packets and block or forward them according to predefined rules set by the network administrator. The gateway also translates between disparate protocols. The gateway only has to deal with two networks—the private network and the external network linking the private network to external systems. The gateway must operate according to the standards of both networks. Because of this dual role, the gateway can act as a translator between the two networks if they operate on different networking standards. Exemplary protocols that are translated include Zigbee, Z-Wave, Bluetooth, Wifi, UWB, among others. The gateway alternatively can be implemented as a proxy server. There are two types of proxy server: forward and reverse. The reverse proxy is a gateway that accepts incoming connections on behalf of network equipment serving external clients. It receives requests on the server's behalf and communicates with the server by a separate channel, retrieving the requested information. A forward proxy server can act as a firewall, blocking all incoming connections or monitoring and filtering the responses to connections originating from within the organization. In both instances, the gateway accepts traffic from one side—either the private LAN or the external network—and fulfills the request itself, without allowing the two sides to connect directly.

In certain embodiments, as part of determining whether the voice query can be acted upon (i.e., processed), the computing device can determine a threshold level of user authentication that is required based on the query's security level (e.g., is voice-based authentication sufficient, or are additional forms of authentication required, such as face, PIN, etc.). The computing device can then prompt the user to authenticate himself/herself using the additional authentication method(s) as needed in order to proceed with query processing. Further, in some embodiments, the step of identifying/authenticating the user can be performed in parallel with the step of recognizing the voice query in order to ensure low latency operation. These and other aspects of the present disclosure are described in additional detail in the sections that follow.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

1. A device comprising:
a housing having a base to support the housing on a surface and a distal top end;
at least one microphone mounted proximal to the top end to receive audio;
a processor mounted within the housing to process a signal representation of the audio to recognize speech and reduce acoustic echoes detected in the signal representation;
at least one speaker mounted in the housing and oriented to output sound in a downward direction toward the base and away from the top end; and
a gateway coupled to the processor to communicate with home appliances, the gateway communicating with a plurality of home area network (HAN) protocols including Zigbee (IEEE 802.15.4), Bluetooth (IEEE 802.15.1) and Z-Wave, the gateway translating HAN data from one protocol to another;
a first home appliance having a first security level;
a second home appliance having a second security level.
2. The device of claim 1, further comprising a speech recognition module executable by the processor to recognize the speech in the signal representation.
3. The device of claim 1, further comprising an acoustic echo cancellation module executable by the processor to reduce the acoustic echoes detected in the signal representation.
4. The device of claim 1, comprising a mobile device with a user key in communication with the processor, wherein the processor authenticates the user key by detecting signals from mobile device.
5. The device of claim 1, wherein the device communicates with a remote server to analyze the verbal command.
6. A method comprising: receiving audio, via one or more microphones, in a device having the one or more microphones positioned at a top end; processing a signal representation of the audio to one or more of (1) recognize speech in the signal representation or (2) cancel acoustic echoes detected in the signal representation; and outputting sound via one or more speakers arranged in a base end of the device, wherein the sound is output from the one or more speakers in a downward direction toward the base end directionally opposite to the one or more microphones at the top end.
7. The method of claim 6, wherein recognizing the speech comprises processing the signal representation to parse the speech.
8. The method of claim 6, further comprising processing the signal representation to reduce double talk detected in the signal representation, in conjunction with cancelling the acoustic echoes detected in the signal representation.
9. The method of claim 6, wherein processing the signal representation comprises substantially cancelling acoustic echoes detected in the signal representation, and then parsing the speech in the signal representation.
10. A device comprising: a housing having a base to support the housing on a surface and a distal end; at least one microphone mounted at the distal end of the housing to receive audio; a processor mounted within the housing to process a signal representation of the audio to one or more of (1) recognize speech in the signal representation or (2) substantially cancel acoustic echoes detected in the signal representation; and at least one speaker arranged inside the housing and oriented to output sound in a direction away from the at least one microphone.
11. The device of claim 10, further comprising a speech recognition module executable by the processor to recognize the speech in the signal representation.
12. The device of claim 11, wherein the speech comprises specific commands.
13. The device of claim 10, further comprising an acoustic echo cancellation module executable by the processor to substantially cancel the acoustic echoes detected in the signal representation.
14. The device of claim 10, wherein the housing has one or more openings near the base to pass sound waves from the at least one speaker.
15. The device of claim 10, wherein the at least one speaker comprises a plurality of speakers that are coaxially aligned.
16. The device of claim 10, wherein the at least one speaker and the at least one microphone are coaxially aligned.
17. The device of claim 10, further comprising a sound distribution cone arranged inside of the housing to distribute the sound emitted from the at least one speaker.
18. The device of claim 17, wherein the at least one speaker and the sound distribution cone are coaxially aligned.
19. The device of claim 17, wherein the sound distribution cone directs the sound at least partially in a radial outward direction.
20. The device of claim 17, wherein the sound distribution cone directs the sound outward from the housing proximal to the base.
1. An appliance, comprising:
a body; a processor in the body and coupled to a wireless transceiver; a camera coupled to the body; and an accelerometer to detect acceleration;
a surface with a sensor to sense characteristics of food or drink;
a motor to affect the food or drink;
a wireless transceiver connected to the Internet; and
a processor coupled to the wireless transceiver and the sensor, the processor miming a voice recognizer to answer a verbal query relating to the appliance and the food or drink.
2. The container of claim 1, comprising a camera coupled to the processor and one or more volume indicia on the container to indicate remaining content.
3. The container of claim 2, comprising mildew detection code to determine the presence of mildew in the container.
4. The container of claim 1, comprising rechargeable battery or super-capacitor coupled to a wireless power receiver in the container to receive power from a layer or sheet of wireless power transmitters.
5. The container of claim 4, wherein the wireless power receiver comprises an NFC receiver and wherein the layer or sheet of wireless power transmitters receive container status data.
6. The container of claim 1, comprising code to report status including content age or quality.
7. The container of claim 1, comprising code to suggest best ways to enjoy the content.
8. The container of claim 1, comprising an electronic nose to detect an odor indicating content quality.

9. The container of claim 1, comprising code to contact a consumer, distributor, retailer, or manufacturer with a status of the content.

10. The container of claim 9, comprising code to exchange information between the consumer and a distributor, retailer or manufacturer of the content.

11. The container of claim 1, comprising a sensor to detect container opening.

12. The container of claim 1, comprising an anti-fraud lid and registration code to detect product tampering or product fraud.

13. The container of claim 1, comprising a MEMS sensor to detect liquid quality, wherein the MEMS sensor detect liquid conductance or resistance and compares with a predetermined quality rating.

14. The container of claim 1, comprising code to sequence usage of the container in a first-in-first-out (FIFO) order to reduce spoilage.

15. The container of claim 1, comprising code to determine if the content is below a predetermined threshold and if so ordering additional supply.

16. The container of claim 15, comprising code to determine expiration date and signaling a user to use prior to the expiration date.

17. A system, comprising:
an appliance;
a digitally responsive container to store content therein, the container received by the appliance, the container, including:
  a volume sensor for the content;
  a wireless transceiver; and
  a processor coupled to the wireless transceiver and the volume sensor, the processor responding to a query on remaining content and quality of the content; and
a smart phone, watch, tablet, or mobile computer wirelessly coupled to one or more of the appliances to control settings on the appliance.

18. The system of claim 17, comprising a camera coupled to the processor and one or more volume indicia on the container to indicate remaining content.

19. The system of claim 17, wherein the container comprises mildew detection code to determine the presence of mildew in the container.

20. The system of claim 17, wherein the container comprises rechargeable battery or super-capacitor coupled to a wireless power receiver in the container to receive power from a layer or sheet of wireless power transmitters.

The IOT appliances can communicate using blockchain as described in co-pending application Ser. Nos. 15/594,311 and 15/594,214 both filed on May 12, 2017, the contents of which are incorporated by reference. The IoT machines can negotiate contracts on their own (without human) and exchange items of value by presenting an open transaction on the associated funds in their respective wallets. Blockchain token ownership is immediately transferred to a new owner after authentication and verification, which are based on network ledgers within a peer-to-peer network, guaranteeing nearly instantaneous execution and settlement. A similar process is used to provide secure communications between IoT devices, which is useful for edge IoT devices. The industrial world is adding billions of new IoT devices and collectively these devices generate many petabytes of data each day. Sending all of this data to the cloud is not only very cost prohibitive but it also creates a greater security risk. Operating at the edge ensures much faster response times, reduced risks, and lower overall costs. Maintaining close proximity to the edge devices rather than sending all data to a distant centralized cloud, minimizes latency allowing for maximum performance, faster response times, and more effective maintenance and operational strategies. In addition to being highly secure, the system also significantly reduces overall bandwidth requirements and the cost of managing widely distributed networks.

In some embodiments, the described technology provides a peer-to-peer cryptographic currency trading method for initiating a market exchange of one or more Blockchain tokens in a virtual wallet for purchasing an asset (e.g., a security) at a purchase price. The system can determine, via a two-phase commit, whether the virtual wallet has a sufficient quantity of Blockchain tokens to purchase virtual assets (such as electricity only from renewable solar/wind/ . . . sources, weather data or location data) and physical asset (such as gasoline for automated vehicles) at the purchase price. In various embodiments, in response to verifying via the two-phase commit that the virtual wallet has a sufficient quantity of Blockchain tokens, the IoT machine purchases (or initiates a process in furtherance of purchasing) the asset with at least one of the Blockchain tokens. In one or more embodiments, if the described technology determines that the virtual wallet has insufficient Blockchain tokens for purchasing the asset, the purchase is terminated without exchanging Blockchain tokens.

The present system provides smart contract management with modules that automates the entire lifecycle of a legally enforceable smart contract by providing tools to author the contract so that it is both judge/arbitrator/lawyer readable and machine readable, and ensuring that all contractual obligations are met by integrating with appropriate execution systems, including traditional court system, arbitration system, or on-line enforcement system. Different from the blockchain/bitcoin contract system where payment is made in advance and released when the conditions are electronically determined to be satisfied, this embodiment creates smart contracts that are verifiable, trustworthy, yet does not require advance payments that restrict the applicability of smart contracts.

In addition to Ethereum, other blockchain or globally shared, transactional database can be used. To change something in the database, the system creates a transaction which has to be accepted by all others. One embodiment runs on an Ethereum Virtual Machine or EVM as the runtime environment for smart contracts in Ethereum. It is not only sandboxed but actually completely isolated, which means that code running inside the EVM has no access to network, filesystem or other processes. Smart contracts have limited access to other smart contracts. There are two kinds of accounts in Ethereum which share the same address space: External accounts that are controlled by public-private key pairs (i.e. humans) and contract accounts which are controlled by the code stored together with the account. The address of an external account is determined from the public key while the address of a contract is determined at the time the contract is created (it is derived from the creator address and the number of transactions sent from that address, the so-called "nonce"). Every account has a persistent key-value store mapping 256-bit words to 256-bit words called storage. Furthermore, every account has a balance in Ether (such as in "Wei") which can be modified by sending transactions that include Ether.

A transaction is a message that is sent from one account to another account (which might be the same or the special zero-account, see below). It can include binary data (its payload) and Ether. If the target account contains code, that code is executed and the payload is provided as input data. If the target account is the zero-account (the account with the address 0), the transaction creates a new contract. As already mentioned, the address of that contract is not the zero address but an address derived from the sender and its number of transactions sent (the "nonce"). The payload of such a contract creation transaction is taken to be EVM bytecode and executed. The output of this execution is permanently stored as the code of the contract. This means that in order to create a contract, you do not send the actual code of the contract, but in fact code that returns that code. Upon creation, each transaction is charged with a certain amount of gas, whose purpose is to limit the amount of work that is needed to execute the transaction and to pay for this execution. While the EVM executes the transaction, the gas is gradually depleted according to specific rules. Each account has a persistent memory area which is called storage. Storage is a key-value store that maps 256-bit words to 256-bit words. It is not possible to enumerate storage from within a contract and it is comparatively costly to read and even more so, to modify storage. A contract can neither read nor write to any storage apart from its own. The second memory area is called memory, of which a contract obtains a freshly cleared instance for each message call. Memory is linear and can be addressed at byte level, but reads are limited to a width of 256 bits, while writes can be either 8 bits or 256 bits wide. Memory is expanded by a word (256-bit), when accessing (either reading or writing) a previously untouched memory word (ie. any offset within a word). At the time of expansion, the cost in gas must be paid. The EVM is not a register machine but a stack machine, so all computations are performed on an area called the stack. It has a maximum size of 1024 elements and contains words of 256 bits. Access to the stack is limited to the top end in the following way: It is possible to copy one of the topmost 16 elements to the top of the stack or swap the topmost element with one of the 16 elements below it. All other operations take the topmost two (or one, or more, depending on the operation) elements from the stack and push the result onto the stack. Of course it is possible to move stack elements to storage or memory, but it is not possible to just access arbitrary elements deeper in the stack without first removing the top of the stack.

The instruction set of the EVM is kept minimal in order to avoid incorrect implementations which can cause consensus problems. All instructions operate on the basic data type, 256-bit words. The usual arithmetic, bit, logical and comparison operations are present. Conditional and unconditional jumps are possible. Furthermore, contracts can access relevant properties of the current block like its number and timestamp.

Contracts can call other contracts or send Ether to non-contract accounts by the means of message calls. Message calls are similar to transactions, in that they have a source, a target, data payload, Ether, gas and return data. In fact, every transaction consists of a top-level message call which in turn can create further message calls.

A contract can decide how much of its remaining gas should be sent with the inner message call and how much it wants to retain. If an out-of-gas exception happens in the inner call (or any other exception), this will be signalled by an error value put onto the stack. In this case, only the gas sent together with the call is used up. In Solidity, the calling contract causes a manual exception by default in such situations, so that exceptions "bubble up" the call stack.

As already said, the called contract (which can be the same as the caller) will receive a freshly cleared instance of memory and has access to the call payload—which will be provided in a separate area called the calldata. After it finished execution, it can return data which will be stored at a location in the caller's memory preallocated by the caller.

With a message call, named delegatecall which is identical to a message call apart from the fact that the code at the target address is executed in the context of the calling contract and msg.sender and msg.value do not change their values, a contract can dynamically load code from a different address at runtime. Storage, current address and balance still refer to the calling contract, only the code is taken from the called address.

Contracts can create other contracts using a special opcode (i.e. they do not simply call the zero address). The only difference between these create calls and normal message calls is that the payload data is executed and the result stored as code and the caller/creator receives the address of the new contract on the stack. More information on Solidity is at Introduction to Smart Contracts at http://solidity.readthedocs.io/en/develop/introduction-to-smart-contracts.html, the content of which is incorporated by reference.

The system enables the physical goods and materials to be identified and linked with their digital representation on the blockchain (e.g., serial numbers, bar codes, digital tags like RFID and NFC, genetic tags) is crucial in uniquely identifying a physical good with its digital counterpart. At Provenance we are exploring many new and existing technologies; an overview of recent technologies can be found here. Identities are recorded in production and manufacturing programs, and for simplicity and easy adoption we expect them to take the form of existing barcodes and serial numbers which are linked to blockchain identifiers using a secure hash.

User-facing applications facilitate access to the blockchain. The final owner of the product has access to secure information about the product's supply chain, without having access to identification details. The final owner of the product has access to secure information about the product's supply chain, without having access to identification details.

By design, every transaction along a supply chain on the blockchain is fully auditable. By inspecting the blockchain, smartphone applications can aggregate and display information to customers in a real-time manner; furthermore, due to the strong integrity properties of the blockchain, this information can be genuinely trusted. A user interface sheds light on the digital journey of a product can empower better purchases by giving users a true choice that they can exercise. There are substantial broad effects of bringing near-frictionless transparency to consumer purchase decisions and product identity; clearly there is likely to be an additional "virtuous" component in purchase decisions, especially among mid-level purchases where a marginal increase of 20% to the price does not affect the willingness to buy. Additional levels of guarantee over genuine articles is a high-value use case. While an initial introduction of this technology may be in the form of a discrete and removable label, easily verified through a smartphone-readable QR-code, a more progressive possibility would be a conspicuous hologramatic or RFID tag, embedded in the brand label, allowing the owner to prove the authenticity of the product at any time by accessing the data on the blockchain through the tag.

In the system, everyone has a profile accessible with a private key. Profiles can be public or private depending on use case and permissions. Some are rich with information, whilst others simply contain an anonymous ID. The system supports the registration of named participants (i.e. certifiers, auditors, producers, and manufacturers). Such participants may request registration of their digital identity which links their real-world identity with their blockchain-based digital identity, thus allowing them to interact with the blockchain using their real-world identity. Upon request, the registration authority verifies their identity and records the result in the blockchain, available for all to inspect.

These programs represent the implementation of schemas for proper recognition of a standard (e.g. no animal testing, biodynamic, fair labor). Through these programs, standards organizations provide for the creation of compliant production or manufacturing programs (see below), allowing instances or batches of goods and materials to be added to or processed on the blockchain. Such producers or manufacturers may require inspection by a certifier or auditor of their facilities and processes to be able to obtain and operate a certified program. Successful verification results in the deployment of a production or manufacturing program that is both registered with the certification program and authenticated by an auditor, and allows a producer to create the digitally tradeable equivalent of a good (i.e., a token that shadows the real-world material or product).

The physical goods and materials are identified and linked with their digital representation on the blockchain using a label (e.g., serial numbers, bar codes, digital tags like RFID and NFC, genetic tags) that uniquely identifies a physical good with its digital counterpart. Identities are recorded in production and manufacturing programs, and for simplicity and easy adoption the system can use electronic tags or barcodes and serial numbers which are linked to blockchain identifiers using a secure hash. During manufacturing, each item is associated with a tag. The tag can be a discrete and removable label, easily read through a smartphone-readable QR-code, a hologram or RFID tag, embedded in the brand label, allowing the owner to prove the authenticity of the product at any time by accessing the data on the blockchain through the tag. While a tag such as a bar code cannot store information, it can save information to a remote server that associates that tag with various blockchains. Alternatively, active memory can be formed using roll-to-roll electronic printing onto a tag and the app can store the position information and additional information to a circuit such as flexible circuit, a printed circuit, or an electronic tag with memory, and the tag can be associated with a product 3 as it moves through production and shipping processes. In one embodiment, the circuit can be "printed memory" that can collect and store information about the authenticity and condition of products. One embodiment uses a Printed Memory containing up to 36 bits of rewritable memory which can store up to 68 billion points of data. The labels are used to determine if a product is genuine and to track how it's been handled during distribution. Another embodiment uses Printed Memory with Cryptographic Security that includes a unique, encrypted printed code (such as a QR bar code) to the memory. It can only be read by authorized personnel using a reader which interfaces with a secure smartphone application. This combination of printed memory with an encrypted printed code, creates a secure anti-counterfeit solutions. This makes it possible to ensure the integrity of a product from the time it leaves the factory to the time it gets into the hands of a customer with a cost efficient, highly secure method of authenticating and verifying information about a product as it moves through various distribution channels or as it is used.

Figure 14K:
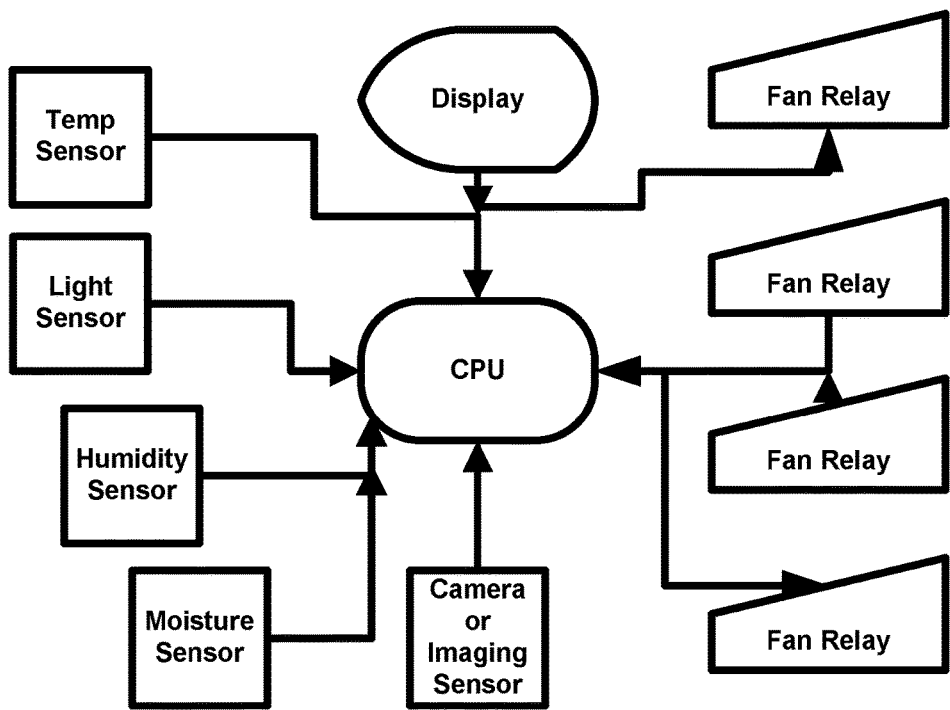

FIG. 14K shows an exemplary farming system with:
an elongated frame or body to grow plant;
a processor in the elongated body and coupled to a wireless transceiver;
a humidity sensor;
a camera coupled to the elongated body; and
a module to record the sensor data and control plant growing action.
The system can include the above with one or more of the following:
a marijuana plant or a cannabis plant.
a timer for the lights, a PH tester, a temperature sensor or a humidity sensor.
a control system to keep room temperature in a predetergreenmined range or CO2 at a predetermined level.
a controller for hydroponic growing.
a controller for lighting.
a fan to provide fresh air.
a pump to dispense cannabis nutrient.
compact fluorescent, high intensity discharge (HID), flourescent, or light emitting diode (LED) light.
a High-intensity discharge light, a High-Pressure Sodium (HPS) light, or a Metal Halide light.
a ballast to receive either HPS (yellow light) for a flowering cycle, and MH (white/blue light).
a full spectrum LED or a predetermined spectrum LED.
an exhaust fan to pull fresh air in and push warm air out of a room.
an air conditioning or temperature control unit.
charcoal carbon filters.
carbon dioxide (CO2) emitter.
one or more sensors to detect one of: temperature, humidity, pH and CO2 levels.
computer controlled light system.
computer controlled thermostat switch coupled to an exhaust fan.
code to turn lights on for 16-20 hours per 24 hour period while the plants are in vegetative growth, then switch to 12 hours of light per 24 hour period to bloom.
hygrometer/thermostat with high/low memory to save highest and lowest readings for a period of time.

Augmented Reality/Virtual Reality Sports Gaming

FIG. 15 shows an exemplary 360 degree camera on a helmet, for example, for augmenting reality of sport games. Using augmented reality, various ways may exist for a user to "participate" in a live event. Generally, augmented reality refers to a presentation of a real world environment augmented with computer-generated data (such as sound, video, graphics or other data). In some embodiments, augmented reality, implemented in conjunction with a live event, may allow a user to control a virtual object that appears to compete or otherwise interact with the participants of the live event. For example, an end user device, such as a mobile phone, tablet computer, laptop computer, or gaming console may be used to present a live video feed of an event to a user. This live video feed may be video of an event that is occurring in real-time, meaning the live event is substantially concurrently with the presentation to the user (for example, buffering, processing, and transmission of the video feed may result in a delay anywhere from less than a second to several minutes). The presentation of the live event may be augmented to contain one or more virtual objects that can be at least partially controlled by the user. For instance, if the live event is a stock car race, the user may be able to drive a virtual car displayed on the end user device to simulate driving in the live event among the actual racers. As such, the user may be able to virtually "compete" against the other drivers in the race. The virtual object, in this example a car, may be of a similar size and shape to the real cars of the video feed. The user may be able to control the virtual car to race against the real cars present in the video feed. The real cars appearing in the video feed may affect the virtual object. For example, the virtual object may not be allowed to virtually move through a real car on the augmented display, rather the user may need to drive the virtual object around the real cars. Besides racing, similar principles may be applied to other forms of live events; for example, track and field events (e.g., discus, running events, the hammer toss, pole vaulting), triathlons, motorbike events, monster truck racing, or any other form of event that a user could virtually participate in against the actual participants in the live event. In some embodiments, a user may be able to virtually replay and participate in past portions of a live event. A user that is observing a live event may desire to attempt to retry an occurrence that happened during the live event. While viewing the live event, the user may be presented with or permitted to select an occurrence that happened in the course of the live event and replay it such that the user's input affects the outcome of at least that portion of the virtualized live event. Using a baseball game as an example, with runners on first and third, two outs, and the count being two balls and two strikes, the pitcher may throw a splitter, successfully striking out the batter with a pitch in the dirt. The inning may end and the game may continue. The user may desire to replay this unsuccessful at-bat with himself controlling the batter during the commercial break. As such, via an end user device, the user may be able to indicate the portion of the game he wishes to replay (e.g., the last at-bat). Game facts from the live event may be used to virtually recreate this at-bat for the user. For instance, the virtual game loaded by the user may use game facts leading up to the at-bat the user has selected. For instance, the opposing team, the stadium, the score, the time of day, the batter, the pitcher, and the sequence of pitches thrown by the pitcher may be used to provide the user with a virtual replay of at least that portion of the baseball game that the user can affect via input (e.g., swinging and aiming the virtual bat). In replaying the selected portion of the live event, the entire event may be virtualized. As such, referring to the baseball example, the pitcher, stadium, field, fielders, batter, and ball may all be replaced by virtual objects, with one (or more) of the virtual objects, such as the batter, being controlled by the user. As such, this may resemble a video game instantiated with data from the live event. In some embodiments, a portion of the live event may involve a playback of a video feed of the live event with a virtual object that is controlled by the user being augmented. Referring again to the example of the baseball game, the pitcher, stadium, fielders, and field may be replayed from the video feed; the batter and/or ball may be virtualized. As such, the user may control the batter and swing at a virtual ball that has taken the place of the real ball present in the video feed. Besides baseball, such reenactment of a portion of a live event may be applied to various forms of sporting events, such as football, soccer, tennis, golf, hockey, basketball, cricket, racing, skiing, gymnastics, and track and field events. Other forms of live events, besides sports, may also be reenacted using such techniques.

Figure 15A:
FIG. 15A shows an exemplary virtual reality camera mounted on a gear.

FIG. 15A shows a multi-headed camera array 423 that may be at least part of a modular camera system, with each camera forming a module of the modular camera system. The camera array has a flexible structure so that it is easy to remove a particular camera module from the camera array and to add new camera modules to the camera array. The camera modules in the camera array may be configured in different geometries. For example, the camera array includes multiple camera modules arranged in a line, a cylinder, a sphere, or another geometry. Each camera module may be configured to point to a different direction so that the camera array may capture an object or a scene from multiple directions at the same time.

The camera system described herein may additionally include a set of algorithms for processing the video data captured by the camera array. The set of algorithms are stored on a non-transitory memory for converting the input across multiple camera modules into a single stream of 3D video (e.g., a single compressed stream of 3D video data). The set of algorithms may be implemented in one or more "modules". For example, the set of algorithms includes color correction algorithms for smoothing and correcting colors in the video data. In another example, the set of algorithms may be implemented in software that stitches the video data from multiple cameras into two large-format, panoramic video streams for left and right eye viewing, and encodes and compresses the video using a standard MPEG format or other suitable encoding/compression format.

The camera array 423 may be constructed using various configurations. For example, the camera modules may be configured in different geometries (e.g., a sphere, a line, a cylinder, a cone, a cube, etc.) with the corresponding lenses 113 facing in different directions. For example, the camera modules are positioned within the camera array 423 in a honeycomb pattern where each of the compartments form an aperture where a camera module may be inserted. In another example, the camera array 423 includes multiple lenses along a horizontal axis and a smaller number of lenses on a vertical axis.

In some embodiments, the camera modules in the camera array 423 are oriented around a sphere in different directions with sufficient diameter and field-of-view to capture enough view disparity to render stereoscopic images.

The camera array 423 has a flexible structure so that a particular camera module may be removed from the camera array 423 easily. In some embodiments, the camera modules are rotationally symmetrical such that a camera module may be inserted into the housing, removed, rotated 90 degrees, and reinserted into the housing. In this example, the sides of the housing may be equidistant, such as a camera module with four equidistant sides. This allows for a landscape orientation or a portrait orientation of the image frames without changing the base. In some embodiments, the lenses and the camera modules are interchangeable. New camera modules may also be added to the camera array 423. In some embodiments, the camera modules in the camera array 423 are positioned to have a sufficient field-of-view overlap so that all objects can be seen by more than one view point. In some embodiments, having the camera array 423 configured so that an object may be viewed by more than one camera may be beneficial for correcting exposure or color deficiencies in the images captured by the camera array 423. Other benefits include disparity/depth calculations, stereoscopic reconstruction, and the potential to perform multi-camera high-dynamic range (HDR) imaging using an alternating mosaic pattern of under- and over-exposure across the camera array.

In some embodiments, the camera array 423 may also include a microphone array for capturing sound from all directions. For example, the microphone array may include a Core Sound Tetramic soundfield tetrahedral microphone array following the principles of ambisonics, enabling reconstruction of sound from any arbitrary direction. In another example, the microphone array includes the Eigenmike, which advantageously includes a greater number of microphones and, as a result, can perform higher-order (i.e. more spatially accurate) ambisonics. The microphone may be mounted to the top of the camera array 423, be positioned between camera modules, or be positioned within the body of the camera array 423. The result can then be rendered as an immersive video and a user can view the video with computer annotations thereon for augmented reality purposes. In one implementation, the event may be a live event, for example, but is not limited to, a football match, a cricket match, a basketball match, a theatre, a concert, and the like. In one embodiment, the augmented reality content may include, but is not restricted to, live content associated with an event, recorded content associated with an event, a curated content, an advertising content, or a combination thereof. In another embodiment, the augmented reality content may include, but is not restricted to, information related to a service available at an event, a venue of an event, a status of a service, or a combination thereof. The system 100 may also provide the augmented reality content associated with, but is not restricted to, a venue of an event, duration of an event, a location of an event, or a combination thereof, in another implementation.

One embodiment allows combined augmented reality and virtual reality on the display. The method may include selectively allowing a transmission of light from a local environment of the user based on a visualization mode of the display object. The visualization mode may be one of an augmented reality mode, a virtual reality mode, and a combination of augmented and virtual reality modes.

In another embodiment, sensors may be placed to track eye movement as well as hand gestures and verbal commands. The method may further comprise capturing a field-of-view image of each of the user's eyes. The captured field of view image may be used to estimate a head pose of the user. The captured field-of-view image may be used to convert at least one physical object to a physically rendered virtual object, and to display the physically rendered virtual object to the user. In another embodiment, sensors may be placed to track eye movement as well as hand gestures and verbal commands. Then, a method comprises tracking a movement of a user's eyes, estimating a depth of focus of the user's eyes based on the tracked eye movement, modifying a light beam associated with a display object based on the estimated depth of focus such that the display object appears in focus, and projecting the modified light beam into the user's eyes. The diameter of the projected light beam projected to the user's eyes may be less than 0.7 mm.

For the athlete/participant who wish to enhance their gaming via augmented or virtual reality, features may include the following:

1. A method for using augmented reality, the method comprising: receiving, by a computerized device, a data stream with a 360 degree view of a live event on each participant, wherein the data stream comprises live video augmented with positions of team mates and opposing players and recommends a play routine based on live field condition and positions of other players, wherein the user can select a point of view from a selected participant.
2. The method for using augmented reality of claim 1, wherein the user plays in a virtual reality version of the live event.
3. The method for using augmented reality of claim 1, wherein the live event is a sporting event.
4. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

Figure 15B:
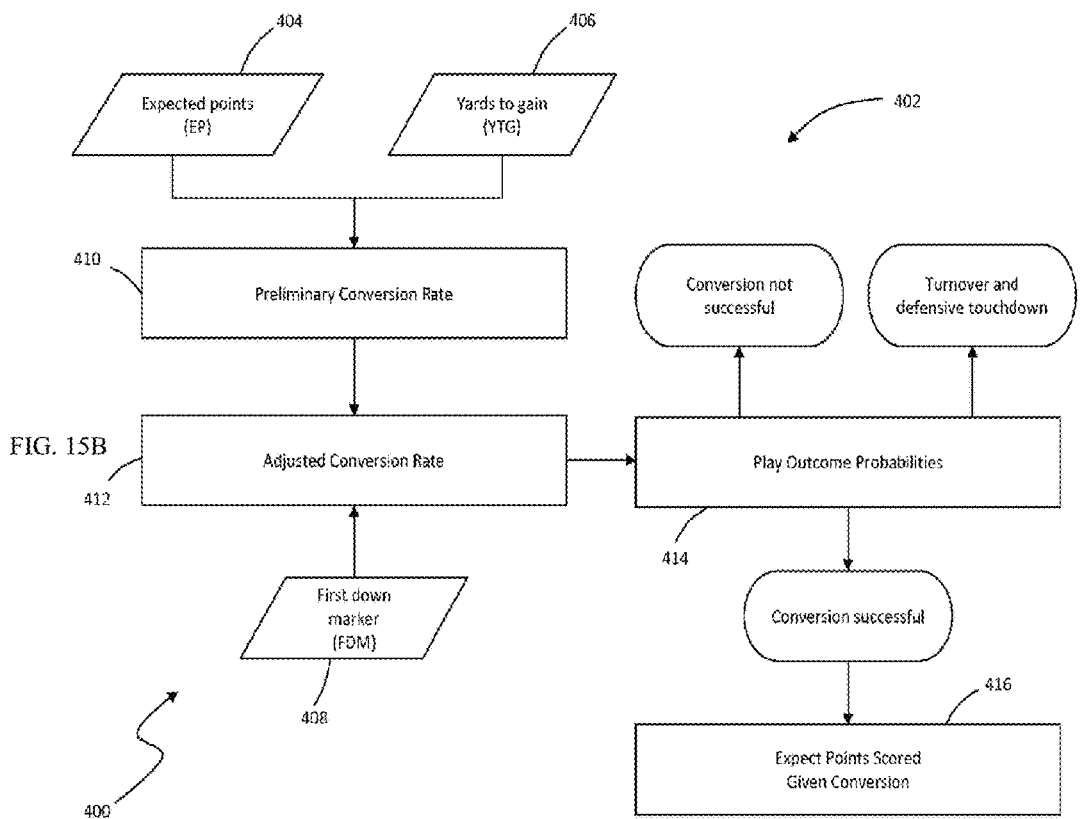
FIG. 15B shows exemplary augmented reality real-time coaching of a player such as a quarterback during fourth down.

FIG. 15 shows an exemplary recommender to aid an athlete in improving the game. For example, the process can recommend a strategy in light of the opponent's historical performance. In tennis, a player's historical weakness can be ascertained and a recommendation can be made to optimize success. In a football example, a fourth down module 400 may include a Football recommender, a Field Goal algorithm, and a Punt algorithm. The Football recommender determines the probability of each potential play outcome associated with the Go For It coaching decision. The Field Goal algorithm determines the probability of each potential play outcome associated with the Field Goal coaching decision. The Punt algorithm 1102 determines the probability of each potential play outcome associated with the Punt coaching decision. As shown in FIG. 15B, the Football recommender 402 determines the probability of each potential play outcome associated with the Go For It coaching decision on a fourth down play. The Football recommender 402 receives an expected points (EP) input from the expected points module 300 at block 404, a yards to gain (YTG) for first down input at block 406, and a first down marker (FDM) yard line input at block 408. Preliminary Conversion Rate: At block 410, the Football recommender 402 uses the team's EP value from block 404 and the YTG distance from block 406 to determine a preliminary first down conversion rate based on historical conversion data. Historical first down conversion data is shown in the form of a chart in FIG. 5, where YTG distances are presented on the x-axis and average first down conversion rates are presented on the y-axis. This historical data shows that the likelihood of a first down conversion decreases as the YTG distance increases. Individual lines or equations may be presented to account for various EP values. For simplicity, FIG. 5 shows three lines to account for scenarios in which the offense and defense are an equal match with the same EP values (NEU), the offense has the advantage (OFF AD), and the defense has the advantage (DEF AD). The historical data presented in FIG. 5 shows that stronger offenses will convert first downs versus weaker defenses (OFF AD) more often than weaker offenses will convert first downs versus stronger defenses (DEF AD). Similar lines may be provided for specific EP values (e.g., 7-66 points). By determining the first down conversion rate at each YTG distance for each offensive match-up, the Football recommender 402 is able to predict the likelihood of a first down conversion with great precision.

Inside an opponent's 20-yard line (i.e., in the Red Zone), it becomes more difficult to convert for a first down as the space on the field from which to work becomes more limited. As the FDM gets closer to the end zone and the YTG distance increases, the challenge of converting a first down gets progressively more difficult versus similar scenarios outside of the Red Zone. To account for the challenge of converting a first down in the Red Zone, the Football recommender 402 may multiply the preliminary conversion rate by a field position multiplier at block 412 based on the YTG distance from block 406 and the FDM yard line from block 408 (where 100 represents the opponent's goal line. As an example, take a team that normally has a 50% fourth down conversion rate with 2 YTG. If the team faces a fourth down play with 2 YTG outside of the Red Zone, the conversion rate may remain at 50%. However, if the team faces a fourth down play with 2 YTG in the Red Zone, such as from the opponent's 2-yard line when the FDM is on the opponent's goal line (FDM=100), the normal 50% conversion rate may be multiplied by the corresponding field position multiplier of 85.5% to arrive at a lower adjusted conversion rate of 42.7%. The process may adjust team's first down conversion rate at block 412 based on particular strengths of his team. In one embodiment, the Football recommender 402 multiplies the conversion rate by one or more additional multipliers, such as a YTG multiplier, which may be specified by the coach. As an example, a team that thrives on running the football might find that it converts short-yardage situations particularly well, because its offense is designed to consistently grind out short gains. However, the same team may have particular difficulty in converting longer-yardage situations because the offense isn't conducive to big plays. In this example, the YTG multiplier may be greater than 100% below 5 YTG to increase the conversion rate in short-yardage situations and less than 100% above 5 YTG to decrease the conversion rate in long-yardage situations. Conversely, a team with an explosive offense may be particularly effective in converting long yardages but may not have the personnel to get short yardage. In this example, the YTG multiplier may be less than 100% below 5 YTG to decrease the conversion rate in short-yardage situations and greater than 100% above 5 YTG to increase the conversion rate in long-yardage situations. The Indianapolis Colts were a great example of this during much of the Peyton Manning era. They were very dangerous in long-yardage situations due to the quality of their passing game, but due to a poor running game, they often failed to convert in short-yardage scenarios. The Football recommender 402 may calculate the probability of a turnover and defensive touchdown as a function of the EP value from block 404 and the FDM yard line from block 408. This probability may be as low as about 0.1% and as high as about 0.5%. At block 414, the Football recommender 402 assigns probabilities to each potential conversion outcome. The Football recommender 402 may determine not only the likelihood of a first down conversion at block 412, but also how likely the team is to score points if the conversion is successful at block 416. After a successful conversion, the team could get just enough yards to get the first down and still not score any points on the drive, or it could score a touchdown on the very same play or a subsequent play of the same drive. Therefore, the Football recommender 402 may take into account the potential upside of the drive should the fourth down play be successful at any field position. At block 416, the Football recommender 402 uses the team's EP value from block 404 and the FDM yard line from block 408 to determine the points scored given conversion based on historical scoring data. Historical scoring data is shown in the form of a chart in FIG. 6, where FDM yard lines are presented on the x-axis (with 0 representing the team's own goal line and 100 representing the opponent's goal line) and average points scored given conversion are presented on the y-axis. This historical data shows that the likelihood of scoring points increases as the FDM approaches the opponent's goal line. Individual lines or equations may be presented to account for various EP values. For simplicity, FIG. 6 shows three lines to account for scenarios in which the offense and defense are an equal match with the same EP values (NEU), the offense has the advantage (OFF AD), and the defense has the advantage (DEF AD). The historical data presented in FIG. 6 shows that stronger offenses will score more points versus weaker defenses (OFF AD) than weaker offenses will score versus stronger defenses (DEF AD). Similar lines may be provided for specific EP values (e.g., 7-66 points). In this manner, the augmented reality system can enhance the game.

For viewers who wish to participate via augmented or virtual reality, features may include the following:

1. A method for using augmented reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, wherein the user can select a point of view from a selected participant.
2. The method for using augmented reality of claim 1, wherein: the virtual object is presented such that the virtual object appears to compete with the live object.
3. The method for using augmented reality of claim 1, wherein the live event is a sporting event.
4. The method for using augmented reality of claim 1, further comprising: receiving, by the computerized device, data corresponding to a second virtual object from a remote computerized device; and displaying, by the computerized device, the live event augmented by the virtual object further augmented with the second virtual object.
5. The method for using augmented reality of claim 4, wherein the behavior of the second virtual object is affected by a second user.
6. The method for using augmented reality of claim 4, further comprising: modifying, by the computerized device, behavior of the virtual object in response to the second virtual object.
7. A method for using augmented reality, the method comprising: receiving, by a computerized device, data corresponding to a live event; presenting, by the computerized device, the live event up to a point in time; presenting, by the computerized device, a virtual event at least partially based on an event that occurred during the live event earlier than the point in time; receiving, by the computerized device, input linked with the virtual event, wherein the input is received from a user; and presenting, by the computerized device, an outcome of the virtual event, wherein the outcome is at least partially based on the input received from the user.
8. The method for using augmented reality of claim 7, wherein: the virtual event is presented at least starting when the live event is stopped.
9. The method of claim 7, wherein the live event is a sporting event.
10. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

11. A method for using virtual reality, the method comprising: receiving, by a computerized device, a data stream with a 360 degree view of a computer generated event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant.

12. A method for using augmented reality and virtual reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, and wherein the virtual reality is rendered by switching the display from an augmented view to a virtual reality view by fading out the augmented view on the display to show only the virtual reality view and switching back when augmented reality view is desired.

Moreoever, the viewers can collaboratively read the situation and recommend a strategy in real-time to improve viewer participation. In this manner, 1. A method for participating in a game, the method comprising: collecting from viewers of a game one or more state change events during a game; determining whether a series of the collected state change events are a known pattern; requesting, when the series of the collected state change events is an unknown pattern, viewers of the game to identify what caused the collected state change events, and judging, by the viewers, a best reason among the identified causes of the collected state change events, 2. The method of claim 1, comprising running a lottery to decide which recommendation is used for the next play in the game.

3. The method of claim 1, further comprising: compensating at least one viewer who is judged to have the best reason among the identified causes of the collected state change events.

4. The method of claim 1, further comprising: storing as the known pattern, the best reason among the identified causes of the collected state change events when one of the pattern is repeated greater than a threshold number of repeats, and the number of the viewers who agree with the corresponding best reason is greater than a threshold number of users.

5. The method of claim 4, further comprising: associating with the stored best reason a corrective action to be taken in response to a future corresponding the collected state change events.

6. The method of claim 4, further comprising: displaying to the other viewers and players, when the stored best reason is known, the occurrence of the stored best reason.

7. The method of claim 5, further comprising: transmitting the stored best reason to other viewers, 8. The method of claim 1, wherein the series of the collected state change events are at least two state change events that occur within a threshold period of time from each other.

Recognition of Exercise Pattern and Tracking of Calorie Consumption

Figure 16A:
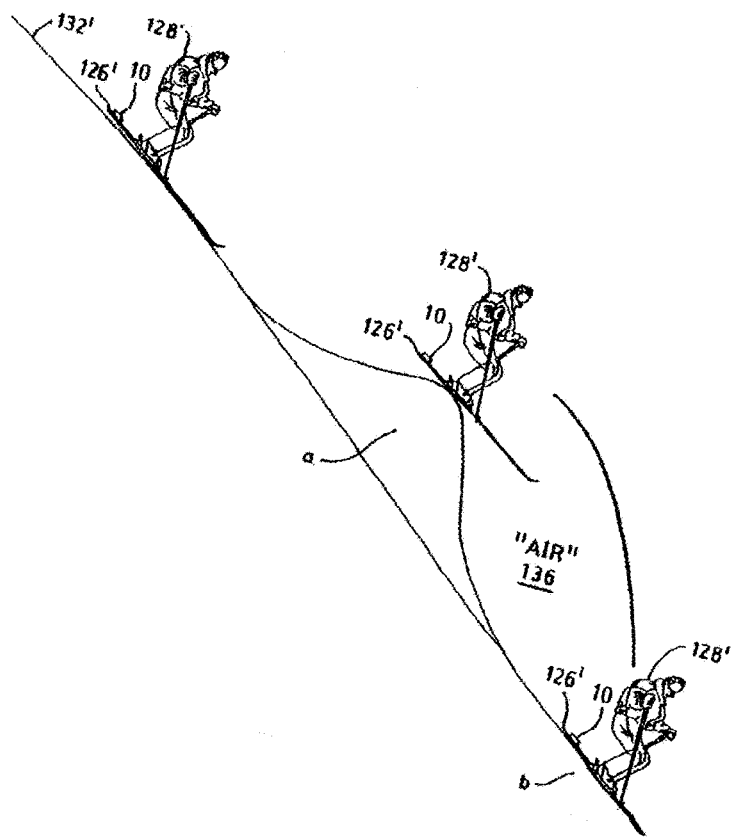

FIG. 16A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

Figure 16B:
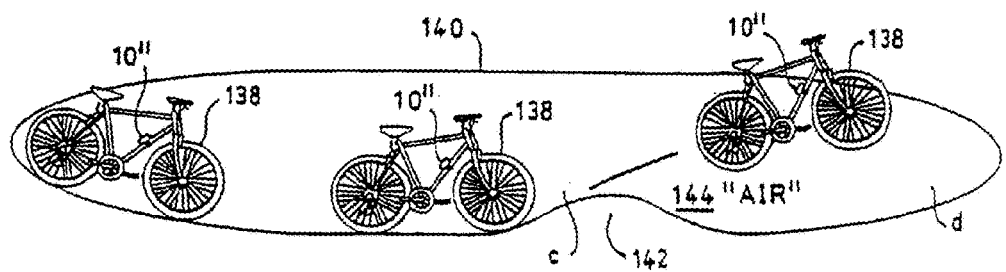
Figure 16C:
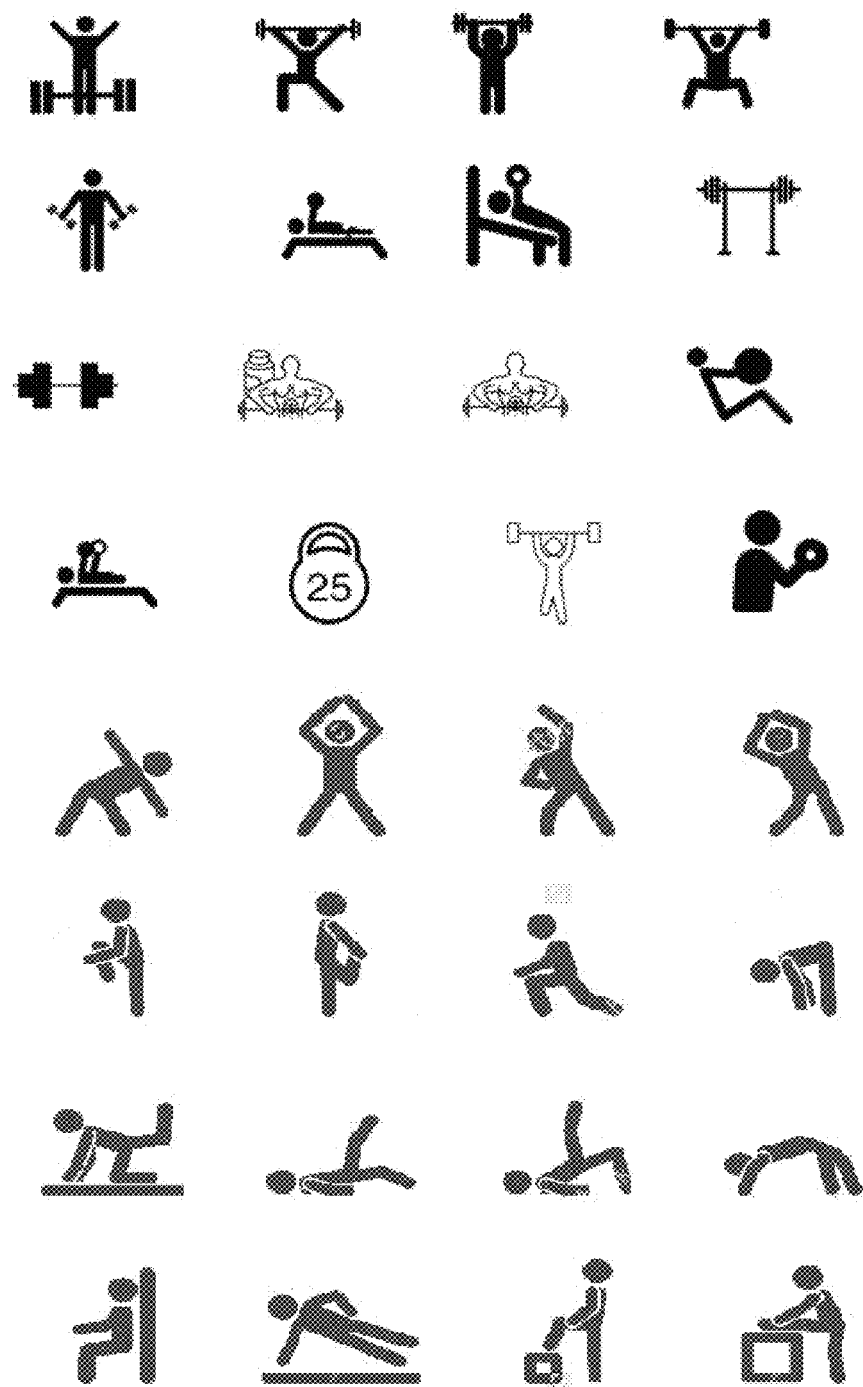

FIG. 16B illustrates a sensing unit 10" mounted onto a mountain bike 138. FIG. 16B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot. The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Figure 16D:
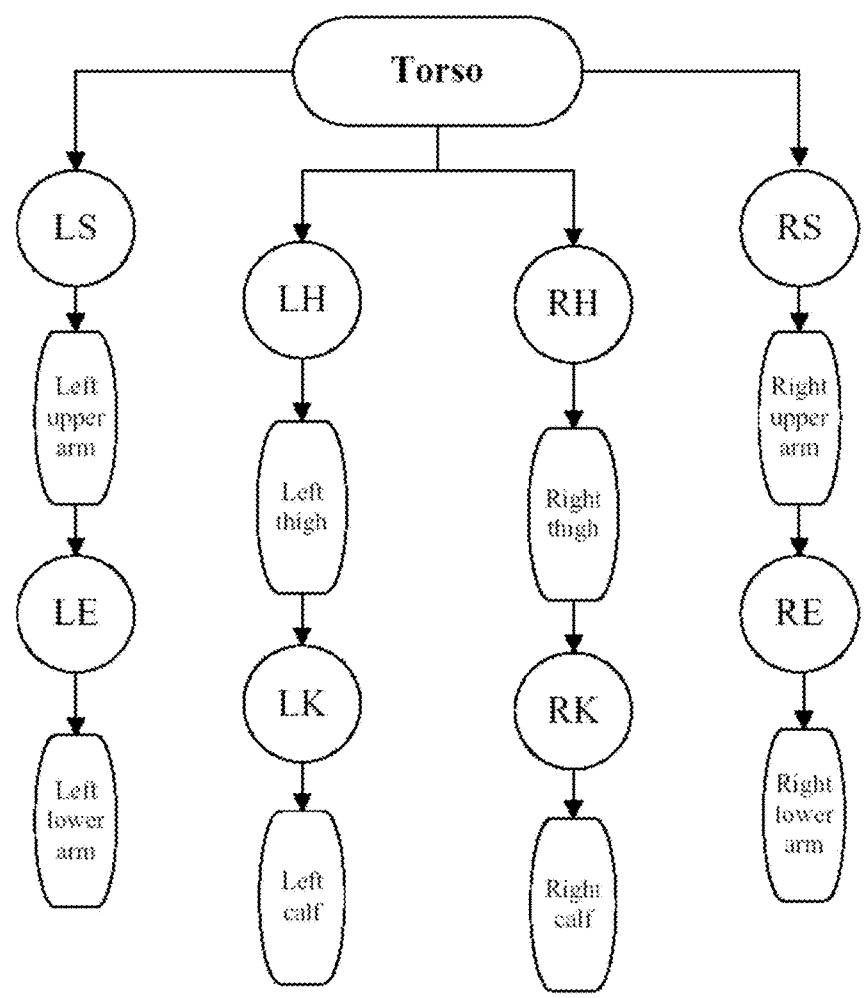
FIG. 16D shows a kinematic modeling for detecting exercise motion which in turn allows precision coaching suggestions.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment shown in FIG. 15C, with motion patterns captured by glove and sock sensors, the system can automatically detect the following exemplary exercise:

Upper Body:
Chest: Barbell Bench Presses, Barbell Incline Presses, Dumbbell Bench Presses, Dumbbell Incline Presses, Dumbbell Flyes, Cable Crossovers
Back: Pull-Ups, Wide-Grip Lat Pulldowns, One-Arm Dumbbell Rows, Seated Cable Rows, Back Extensions, Straight Arm Pulldowns
Shoulders: Seated Dumbbell Presses, Front Raises, Lateral Raises, Reverse Flyes, Upright Cable Rows, Upright Barbell Rows
Biceps: Alternate Dumbbell Curls, Barbell Curls, Preacher Curls, Concentration Curls, Cable Curls, Hammer Curls
Triceps: Seated Triceps Presses, Lying Triceps Presses, Triceps Kickbacks, Triceps Pushdowns, Cable Extensions, Bench Dips
Lower Body
Quadriceps: Barbell Squats, Leg Presses, Leg Extensions
Hamstrings: Dumbbell Lunges, Straight-Leg Deadlifts, Lying Leg Curls
Calves: Seated Calf Raises, Standing Heel Raises
Abs: Floor Crunches, Oblique Floor Crunches, Decline Crunches, Decline Oblique, Hanging Knee Raises, Reverse Crunches, Cable Crunches, Cable Oblique Crunches In one implementation in FIG. 16D, an HMM is used to track weightlifting motor skills or sport enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the sport enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the sport enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the sport enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first xmin and considered to be the start of the first brushstroke. The first maximumxvalue following the first minimumxvalue is located and construed to be the middle of the first exercise stroke (where exercise motion changes from one direction to the other). The next xmin value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (xmax and xmin) are determined. The Y-direction lengths, Ly1 and Ly2, between the data points just before and just after each of xmax and xmin (xmax+1, xmax−1, and Xmin+1, xmin−1) are then determined. The length Lx along the x axis, between xmax and xmin, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, sport enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Sport enthusiasts with pure motor hemiparesis present with face, arm, and leg weakness. This condition usually affects the extremities equally, but in some cases it affects one extremity more than the other. The most common stroke location in affected sport enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Sport enthusiasts with clumsy-hand dysarthria syndrome experience unilateral hand weakness and dysarthria. The dysarthria is often severe, whereas the hand involvement is more subtle, and sport enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the sport enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the sport enthusiast to get to a resting place or a notification to a nurse or caregiver to render timely assistance. The amplitude of the EMG signal is stochastic (random) in nature and can be reasonably represented by a Gaussian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Features of the auto-detection of exercise include the following:

1. An exercise system, comprising:
   a processor running the motion analyzer and coupled to a wireless transceiver;
   an accelerometer coupled to the processor; and
   a kinematic motion analysis module executed by the processor to detect exercise type.
2. The system of claim 1, comprising a plurality of smart modules mounted on an exerciser forming a mesh network.
3. The system of claim 1 where the electronic components, sensors, and interconnects of the system monitor, record, process and/or transmit events of interest (such as accelerometers and gyroscopes for impact events, temperature sensors for temperature and/or temperature gradients, pressure sensors, moisture sensors, chemical sensors).
4. The system of claim 1 comprised for sensing and/or monitoring impact events where the sensors are accelerometers, gyroscopes, and/or pressure sensors.
5. The system of claim 1 comprised for sensing and/or monitoring and/or controlling ongoing events where the sensors monitor temperature, temperature gradients, motion, position, environmental or chemical levels, or other such information.

6. The system of claim 1 comprised for sensing events or other information including mounting multiple distributed sensors for obtaining spatial and/or temporal distribution in the data and/or multiple sensors sensing different information and data.

7. The system of claim 1 comprising a camera and an image recognition module to determine kinematic movement.

8. The system of claim 1 including a statistical recognizer to determine kinematic movement.

9. The system of claim 8, comprising a model-state that contains the extracted features of body signatures and other associated characteristics of body signatures.

10. The system of claim 1 comprising links connecting a root node (torso) with connected joint, left shoulder (LS), right shoulder (RS), left hip (LH), and right hip (RH), and left elbow (LE), right elbow (RE), left knee (LK), and right knee (RK) connect upper and lower extremities.

11. The system of claim 1 comprising a posture detection module.

12. The system of claim 1, comprising a module to detect a lying down state and a standing state.

13. The system of claim 1, comprising a hidden markov model module to detect muscle movement and exercise pattern.

14. The system of claim 1 comprising optimizing tennis shots to improve serve, groundstroke, volley, half volley, smash, forehand, backhand, flat, side spin, block, slice, topspin shot, lob, passing shot, dropshot, crosscourt shot, down-the-line shot.

15. The system of claim 1, comprising an electromyography (EMG) sensor to detect muscle strength or weakness.

16. The system of claim 1, comprising an emotion detector wherein an exercise can be increased, decreased, or stopped based on detected emotion.

17. The system of claim 17, wherein the detector comprises video detection of faces or a GSR sensor.

18. The system of claim 1 comprising a cloud storage to receive sensor data.

19. The system of claim 1, comprising a golf training module that checks that a golfer has a low center of gravity to remain balanced throughout a swing path, that a swing starts with the arms moving back in a straight line, and when a club head reaches the level of the hip, a wrist cock acts as a hinge along with the left knee (for a right handed swing), building up torque by moving into the same line as the belly button before the start of the upswing. As the swing continues to the top of the backswing (again for right handed golf swing), the golfer's left arm is straight and a right arm is hinged at the elbow.

20. The system of claim 19, wherein the golf training module checks that a downswing begins with the hips and the lower body and as the golfer's hips turn into the shot, the right elbow drops down, hugging the right side of the golfer's torso and wrists begin to snap through from the wrist cock in the backswing.

21. The system of claim 1, comprising a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping.

22. The system of claim 1, comprising a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

23. The system of claim 1, comprising a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor 14 can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other sport vehicle. Collectively, the sport objects such as the ski boot and the variety of sport vehicles are denoted as "sport implements". Accordingly, when the sensing unit is not "stand alone", the housing which integrates the controller subsystem with one or more sensors and battery can be made from the material of the associated sport implement, in whole or in part, such that the sensing unit becomes integral with the sport implement. The universal interface is therefore not desired in this aspect.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The embodiments described herein may include the use of a special purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include tangible computer-readable storage media including RAM, ROM, EEPROM, CD-ROM or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media. Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. As used herein, the term "module" or "component" may refer to software objects or routines that execute on the computing system. The different components, modules, engines, and services described herein may be implemented as objects or processes that execute on the computing system (e.g., as separate threads). While the system and methods described herein may be preferably implemented in software, implementations in hardware or a combination of software and hardware are also possible and contemplated. In this description, a "computing entity" may be any computing system as previously defined herein, or any module or combination of modulates running on a computing system. All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A sports device, comprising:
    a device body;
    a processor in the device body and coupled to a wireless transceiver;
    a camera sensor coupled to the device body to provide a 3D model of an object and a distance of the object from the device to the processor to be displayed on a display;
    an accelerometer disposed within the device body to detect acceleration of the device; and
    a module to compare a professional motion with a user motion to improve a play.

2. The device of claim 1, wherein at least one sensor is selected from one of: a pressure sensor; a motion sensor; a digit motion sensor; a temperature sensor; and a contact sensor.

3. The device of claim 1, wherein the sensor comprises at least one of the same as the second sensor or different than the second sensor, the hand exercise event at least one of the same as the second-hand exercise event or different than the second hand exercise event.

4. The device of claim 1, comprising a hand exercise regimen selected from one of: a physical therapy hand exercise regimen; a physical training hand exercise regimen; or a physical performance hand exercise regimen.

5. The device of claim 1, comprising a gesture identifying component configured to identify at least one hand gesture detected by at least one sensor.

6. The device of claim 1, comprising a plurality of finger receptacles, each having a sensor.

7. The device of claim 1, comprising a sensor worn by an opponent in wireless communication with the processor to communicate the force of an impact from the device.

8. The device of claim 1, wherein the device body comprises a wearable device.

9. The device of claim 1, comprising a hidden markov model module to detect muscle movement and exercise pattern.

10. The device of claim 1, comprising an emotion detector.

11. A system for measuring a force of impact, comprising:
    an accelerometer disposed in a device body for measuring the force of impact on a player;
    a camera sensor coupled to the device body to capture a 3D model of an anatomical part and a distance;
    a radio frequency transmitter coupled to the accelerometer for transmitting impact measurements;
    a radio frequency receiver for receiving the impact measurements; and
    a display coupled to the radio frequency receiver for displaying measured impacts, an anatomical part being hit and the force on the anatomical part.

12. The system of claim 11, wherein at least one sensor is selected from one of: a pressure sensor configured to detect at least one pressure event at a device body external surface location; a device motion sensor configured to detect at least one motion event of the device; a digit motion sensor configured to detect at least one motion event of at least one digit of the user; a temperature sensor configured to detect a temperature at a device body external surface location; and a contact sensor configured to detect a contact event of the device with a contact object.

13. The system of claim 11, wherein at least one sensor is selected from one of: a pressure sensor; a motion sensor; a digit motion sensor; a temperature sensor; and a contact sensor.

14. The system of claim 11, comprising a hand exercise regimen selected from one of: a physical therapy hand exercise regimen; a physical training hand exercise regimen; or a physical performance hand exercise regimen.

15. The system of claim 11, wherein the device comprises a gesture identifying component.

16. The system of claim 11, wherein the device comprises a plurality of finger receptacles, each having a sensor.

17. The system of claim 11, comprising a sensor worn by an opponent in wireless communication with the processor to communicate the force of an impact from the device and a module to: receive views of a live event from the handle camera and from one or more external cameras; augment the views with a viewer action as detected by sensors coupled to a viewer; and compare a professional result with the viewer action.

18. The system of claim 11, wherein the device body comprises a wearable device.

19. The system of claim 11, comprising a hidden markov model module to detect muscle movement and exercise pattern.

20. The system of claim 11, comprising an emotion detector wherein an exercise can be increased, decreased, or stopped based on detected emotion.

* * * * *